US009562077B2

(12) United States Patent
Tan et al.

(10) Patent No.: US 9,562,077 B2
(45) Date of Patent: Feb. 7, 2017

(54) PROTEIN COMPLEX SYSTEM FOR INCREASED IMMUNOGENICITY AND FUNCTIONALITY, AND METHODS MAKING AND USE

(71) Applicant: Children's Hospital Medical Center, Cincinnati, OH (US)

(72) Inventors: Ming Tan, Cincinnati, OH (US); Xi Jiang, Cincinnati, OH (US); Leyi Wang, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 239 days.

(21) Appl. No.: 13/803,057

(22) Filed: Mar. 14, 2013

(65) Prior Publication Data

US 2014/0017269 A1    Jan. 16, 2014

Related U.S. Application Data

(60) Provisional application No. 61/670,288, filed on Jul. 11, 2012.

(51) Int. Cl.
*C07K 14/005* (2006.01)
*A61K 39/12* (2006.01)
(Continued)

(52) U.S. Cl.
CPC ............ *C07K 14/005* (2013.01); *A61K 39/12* (2013.01); *A61K 39/385* (2013.01);
(Continued)

(58) Field of Classification Search
None
See application file for complete search history.

(56) References Cited

U.S. PATENT DOCUMENTS

| 6,303,369 | B1 * | 10/2001 | Spana et al. ............... 435/320.1 |
| 8,486,421 | B2 * | 7/2013 | Jiang et al. ............... 424/216.1 |
| 2012/0009211 | A1 | 1/2012 | Tschopp et al. |

OTHER PUBLICATIONS

UNIPROT Q913Z3_9CALI (2001).*
(Continued)

*Primary Examiner* — Michelle S Horning
(74) *Attorney, Agent, or Firm* — Frost Brown Todd LLC

(57) ABSTRACT

Genes for proteins which spontaneously form dimers and/or oligomers can be recombinantly linked together, which upon expression in *E. coli* produces stable dimeric fusion proteins that spontaneously self-assemble into enormous, polyvalent complexes having increased immunogenicity and functionality. Linear, network and agglomerate complexes with enormous sizes and polyvalences are constructed using glutathione S-transferase, Norovirus P domains (NoV P⁻ and NoV⁺), the protruding (P) domain of hepatitis E virus (HEV P), the astrovirus P domain (AstV), a monomeric peptide epitope (M2e of influenza virus), and/or a protein antigen (VP8* of rotavirus) fused in different combinations. The resulting complexes can contain hundreds to thousands NoV P-protein, HEV, AstV, M2e and/or VP8* copies and exhibit higher immunogenicity than the individual proteins alone. The large size and multivalent nature of the complexes are candidates as a bivalent or multivalent vaccines against Norovirus and other pathogens, and for generation of antibodies for diagnosis and research purposes.

14 Claims, 16 Drawing Sheets

(51) Int. Cl.
*A61K 39/385* (2006.01)
*A61K 39/00* (2006.01)

(52) U.S. Cl.
CPC .. *A61K 2039/543* (2013.01); *A61K 2039/627* (2013.01); *A61K 2039/64* (2013.01); *A61K 2039/70* (2013.01); *C07K 2319/23* (2013.01); *C07K 2319/40* (2013.01); *C07K 2319/50* (2013.01); *C07K 2319/70* (2013.01); *C12N 2720/12322* (2013.01); *C12N 2720/12334* (2013.01); *C12N 2760/16022* (2013.01); *C12N 2760/16034* (2013.01); *C12N 2760/16134* (2013.01); *C12N 2770/16022* (2013.01); *C12N 2770/16034* (2013.01); *C12N 2770/28122* (2013.01)

(56) References Cited

OTHER PUBLICATIONS

De Filette et al. An influenza A vaccine based on tetrameric ectodomain of matrix protein 2. J Biol Chem. Apr. 25, 2008;283(17)11382-7.*
International Search Report and Written Opinion dated Oct. 16, 2013 for Application No. PCT/US2013/050004.
NCBI, GenBank accession No. ADF50093.1, Apr. 25, 2010.
Tan, M. Et al., "Norovirus P particle: a subviral nano article for vaccine development against norovirus, rotavirus and influenza virus", Nanomedicine, Jun. 2012, vol. 7, No. 6, pp. 889-897.
Wang, L. et al., "Polyvalent complexes for vaccine development", Biomaterials, Mar. 15, 2013, vol. 34, pp. 4480-4492.
Xia, M, et al., "A candidate dual vaccine against influenza and noroviruses", Vaccine, 2011, vol. 29, No. 44, pp. 7670-7677.

* cited by examiner

SEQUENCE LISTING

```
<160> NUMBER OF SEQ ID NOS: 57

<210> SEQ ID NO 1
<211> LENGTH: 398
<212> TYPE: PRT
<213> ORGANISM: Artificial Sequence
<220> FEATURE:
<223> OTHER INFORMATION: GST-HEV P fusion protein

<400> SEQUENCE: 1

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Asp Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Thr Pro Ser Pro Ala Pro Ser Arg Pro Phe Ser Val Leu Arg Ala Asn
225                 230                 235                 240

Asp Val Leu Trp Leu Ser Leu Thr Ala Ala Glu Tyr Asp Gln Thr Thr
                245                 250                 255

Tyr Gly Ser Ser Thr Asn Pro Met Tyr Val Ser Asp Thr Val Thr Phe
            260                 265                 270

Val Asn Val Ala Thr Gly Ala Gln Ala Val Ala Arg Ser Leu Asp Trp
        275                 280                 285

Ser Lys Val Thr Leu Asp Gly Arg Pro Leu Thr Thr Ile Gln Gln Tyr
    290                 295                 300
```

```
Ser Lys Thr Phe Tyr Val Leu Pro Leu Arg Gly Lys Leu Ser Phe Trp
305                 310                 315                 320

Glu Ala Ser Thr Thr Lys Ala Gly Tyr Pro Tyr Asn Tyr Asn Thr Thr
                325                 330                 335

Ala Ser Asp Gln Ile Leu Ile Glu Asn Ala Ala Gly His Arg Val Ala
            340                 345                 350

Ile Ser Thr Tyr Thr Thr Ser Leu Gly Ala Gly Pro Thr Ser Ile Ser
        355                 360                 365

Ala Val Gly Val Leu Ala Pro His Ser Ala Leu Ala Ala Leu Glu Asp
    370                 375                 380

Thr Val Asp Tyr Pro Cys Asp Cys Arg Gly Asp Cys Phe Cys
385                 390                 395
```

<210> SEQ ID NO 2
<211> LENGTH: 551
<212> TYPE: PRT
<213> ORGANISM: Artificial Sequence
<220> FEATURE:
<223> OTHER INFORMATION: GST-NoV P+

<400> SEQUENCE: 2

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Asp Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Ser Arg Thr Lys Pro Phe Thr Val Pro Ile Leu Thr Val Glu Glu Met
225                 230                 235                 240

Ser Asn Ser Arg Phe Pro Ile Pro Leu Glu Lys Leu Tyr Thr Gly Pro
                245                 250                 255

Ser Ser Ala Phe Val Val Gln Pro Gln Asn Gly Arg Cys Thr Thr Asp
            260                 265                 270
```

-continued

Gly Val Leu Leu Gly Thr Thr Gln Leu Ser Ala Val Asn Ile Cys Thr
                275                 280                 285

Phe Arg Gly Asp Val Thr His Ile Ala Gly Ser His Asp Tyr Ile Met
            290                 295                 300

Asn Leu Ala Ser Gln Asn Trp Asn Asn Tyr Asp Pro Thr Glu Glu Ile
305                 310                 315                 320

Pro Ala Pro Leu Gly Thr Pro Asp Phe Val Gly Lys Ile Gln Gly Met
                325                 330                 335

Leu Thr Gln Thr Thr Arg Glu Asp Gly Ser Thr Arg Ala His Lys Ala
            340                 345                 350

Thr Val Ser Thr Gly Ser Val His Phe Thr Pro Lys Leu Gly Ser Val
        355                 360                 365

Gln Tyr Thr Thr Asp Thr Asn Asn Asp Leu Gln Thr Gly Gln Asn Thr
    370                 375                 380

Lys Phe Thr Pro Val Gly Val Ile Gln Asp Gly Asn Asn His Gln Asn
385                 390                 395                 400

Glu Pro Gln Gln Trp Val Leu Pro Asn Tyr Ser Gly Arg Thr Gly His
                405                 410                 415

Asn Val His Leu Ala Pro Ala Val Ala Pro Thr Phe Pro Gly Glu Gln
            420                 425                 430

Leu Leu Phe Phe Arg Ser Thr Met Pro Gly Cys Ser Gly Tyr Pro Asn
        435                 440                 445

Met Asn Leu Asp Cys Leu Leu Pro Gln Glu Trp Val Gln His Phe Tyr
    450                 455                 460

Gln Glu Ala Ala Pro Ala Gln Ser Asp Val Ala Leu Leu Arg Phe Val
465                 470                 475                 480

Asn Pro Asp Thr Gly Arg Val Leu Phe Glu Cys Lys Leu His Lys Ser
                485                 490                 495

Gly Tyr Val Thr Val Ala His Thr Gly Pro His Asp Leu Val Ile Pro
            500                 505                 510

Pro Asn Gly Tyr Phe Arg Phe Asp Ser Trp Val Asn Gln Phe Tyr Thr
        515                 520                 525

Leu Ala Pro Met Gly Asn Gly Ala Gly Arg Arg Arg Ala Leu Cys Asp
    530                 535                 540

Cys Arg Gly Asp Cys Phe Cys
545                 550

<210> SEQ ID NO 3
<211> LENGTH: 538
<212> TYPE: PRT
<213> ORGANISM: Artificial Sequence
<220> FEATURE:
<223> OTHER INFORMATION: GST-NoV P-

<400> SEQUENCE: 3

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

```
Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Asp His Pro Pro Lys Ser Asp Leu Val Pro Arg
    210                 215                 220

Ser Arg Thr Lys Pro Phe Thr Val Pro Ile Leu Thr Val Glu Glu Met
225                 230                 235                 240

Ser Asn Ser Arg Phe Pro Ile Pro Leu Glu Lys Leu Tyr Thr Gly Pro
                245                 250                 255

Ser Ser Ala Phe Val Val Gln Pro Gln Asn Gly Arg Cys Thr Thr Asp
            260                 265                 270

Gly Val Leu Leu Gly Thr Thr Gln Leu Ser Ala Val Asn Ile Cys Thr
        275                 280                 285

Phe Arg Gly Asp Val Thr His Ile Ala Gly Ser His Asp Tyr Ile Met
    290                 295                 300

Asn Leu Ala Ser Gln Asn Trp Asn Asn Tyr Asp Pro Thr Glu Glu Ile
305                 310                 315                 320

Pro Ala Pro Leu Gly Thr Pro Asp Phe Val Gly Lys Ile Gln Gly Met
                325                 330                 335

Leu Thr Gln Thr Thr Arg Glu Asp Gly Ser Thr Arg Ala His Lys Ala
            340                 345                 350

Thr Val Ser Thr Gly Ser Val His Phe Thr Pro Lys Leu Gly Ser Val
        355                 360                 365

Gln Tyr Thr Thr Asp Thr Asn Asn Asp Leu Gln Thr Gly Gln Asn Thr
    370                 375                 380

Lys Phe Thr Pro Val Gly Val Ile Gln Asp Gly Asn Asn His Gln Asn
385                 390                 395                 400

Glu Pro Gln Gln Trp Val Leu Pro Asn Tyr Ser Gly Arg Thr Gly His
                405                 410                 415

Asn Val His Leu Ala Pro Ala Val Ala Pro Thr Phe Pro Gly Glu Gln
            420                 425                 430

Leu Leu Phe Phe Arg Ser Thr Met Pro Gly Cys Ser Gly Tyr Pro Asn
        435                 440                 445

Met Asn Leu Asp Cys Leu Leu Pro Gln Glu Trp Val Gln His Phe Tyr
    450                 455                 460

Gln Glu Ala Ala Pro Ala Gln Ser Asp Val Ala Leu Leu Arg Phe Val
465                 470                 475                 480

Asn Pro Asp Thr Gly Arg Val Leu Phe Glu Cys Lys Leu His Lys Ser
                485                 490                 495
```

Gly Tyr Val Thr Val Ala His Thr Gly Pro His Asp Leu Val Ile Pro
            500                 505                 510

Pro Asn Gly Tyr Phe Arg Phe Asp Ser Trp Val Asn Gln Phe Tyr Thr
            515                 520                 525

Leu Ala Pro Met Gly Asn Gly Ala Gly Arg
        530                 535

<210> SEQ ID NO 4
<211> LENGTH: 856
<212> TYPE: PRT
<213> ORGANISM: Artificial Sequence
<220> FEATURE:
<223> OTHER INFORMATION: GST-NoV P-(387)-NoV P-(207) fusion protein

<400> SEQUENCE: 4

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Ser Arg Thr Lys Pro Phe Thr Val Pro Ile Leu Thr Val Glu Glu Met
225                 230                 235                 240

Ser Asn Ser Arg Phe Pro Ile Pro Leu Glu Lys Leu Tyr Thr Gly Pro
                245                 250                 255

Ser Ser Ala Phe Val Val Gln Pro Gln Asn Gly Arg Cys Thr Thr Asp
            260                 265                 270

Gly Val Leu Leu Gly Thr Thr Gln Leu Ser Ala Val Asn Ile Cys Thr
        275                 280                 285

Phe Arg Gly Asp Val Thr His Ile Ala Gly Ser His Asp Tyr Ile Met
    290                 295                 300

Asn Leu Ala Ser Gln Asn Trp Asn Asn Tyr Asp Pro Thr Glu Glu Ile
305                 310                 315                 320

```
Pro Ala Pro Leu Gly Thr Pro Asp Phe Val Gly Lys Ile Gln Gly Met
            325                 330                 335

Leu Thr Gln Thr Thr Arg Glu Asp Gly Ser Thr Arg Ala His Lys Ala
        340                 345                 350

Thr Val Ser Thr Gly Ser Val His Phe Thr Pro Lys Leu Gly Ser Val
            355                 360                 365

Gln Tyr Thr Thr Asp Thr Asn Asn Asp Leu Gln Thr Gly Gln Asn Thr
        370                 375                 380

Lys Phe Thr Pro Val Gly Val Ile Gln Asp Gly Asn Asn His Gln Asn
385                 390                 395                 400

Glu Pro Gln Gln Trp Val Leu Pro Asn Tyr Ser Gly Arg Thr Gly His
            405                 410                 415

Asn Val His Leu Ala Pro Ala Val Ala Pro Thr Phe Pro Gly Glu Gln
                420                 425                 430

Leu Leu Phe Phe Arg Ser Thr Met Pro Gly Cys Ser Gly Tyr Pro Asn
            435                 440                 445

Met Asn Leu Asp Cys Leu Leu Pro Gln Glu Trp Val Gln His Phe Tyr
        450                 455                 460

Gln Glu Ala Ala Pro Ala Gln Ser Asp Val Ala Leu Leu Arg Phe Val
465                 470                 475                 480

Asn Pro Asp Thr Gly Arg Val Leu Phe Glu Cys Lys Leu His Lys Ser
            485                 490                 495

Gly Tyr Val Thr Val Ala His Thr Gly Pro His Asp Leu Val Ile Pro
                500                 505                 510

Pro Asn Gly Tyr Phe Arg Phe Asp Ser Trp Val Asn Gln Phe Tyr Thr
            515                 520                 525

Leu Ala Pro Met Gly Asn Gly Ala Gly Arg Gly Gly Gly Gly Gly Gly
        530                 535                 540

Ser Lys Thr Lys Ala Phe Thr Ile Pro Val Leu Lys Ile Ser Glu Met
545                 550                 555                 560

Thr Asn Ser Arg Phe Pro Val Pro Val Asp Gln Met Tyr Thr Ser Arg
            565                 570                 575

Ser Glu Gly Ile Val Val Gln Pro Gln Asn Gly Arg Ala Thr Ile Asp
                580                 585                 590

Gly Glu Leu Leu Gly Thr Thr Leu Val Ser Pro Val Ser Val Cys Asn
            595                 600                 605

Phe Lys Gly Asn Leu Gln Ala Glu Val Pro Gly Gln His Gln Leu Tyr
        610                 615                 620

Gln Leu Gln Leu Thr Asn Leu Asp Gly Ser Pro Ile Asp Pro Thr Asp
625                 630                 635                 640

Asp Thr Pro Gly Pro Leu Gly Cys Pro Asp Phe Thr Gly Leu Leu Tyr
            645                 650                 655

Gly Val Ala Ser Gln Arg Gly Pro Gly Asp Ala Thr Arg Ala His Glu
                660                 665                 670

Ala Arg Ile Asp Thr Gly Ser Asp Thr Phe Ala Pro Lys Ile Gly Gln
            675                 680                 685

Val Arg Phe Tyr Ser Thr Ser Ser Asp Phe Glu Thr Asn Gln Pro Thr
        690                 695                 700

His Phe Thr Pro Ile Gly Ile Tyr Ile Glu Gly Asn Ser Ser Asp Phe
705                 710                 715                 720

Asn Gln Trp Gln Leu Pro Arg Tyr Gly Gly His Leu Ala Asn Asn Asn
            725                 730                 735

His Leu Ala Pro Ala Val Ser Pro Leu Phe Pro Gly Glu Gln Ile Leu
```

```
                740                 745                 750
Phe Phe Arg Ser Phe Ile Pro Gly Ala Ser Gly His Thr Asn Gly Glu
            755                 760                 765

Met Asp Cys Leu Leu Pro Gln Glu Phe Val Gln His Phe Tyr Gln Glu
        770                 775                 780

Ala Ala Thr Ala Arg Ser Glu Val Ala Leu Leu Arg Phe Val Asn Pro
785                 790                 795                 800

Asp Thr Gly Arg Ala Leu Phe Glu Ser Lys Leu His Lys Gln Gly Phe
                805                 810                 815

Met Thr Ile Ala Ser Ser Gly Asp His Pro Ile Ile Met Pro Thr Asn
            820                 825                 830

Gly Tyr Phe Arg Phe Glu Ala Trp Val Asn Gln Phe Tyr Ser Leu Ala
        835                 840                 845

Pro Val Gly Thr Gly Ser Gly Arg
    850                 855

<210> SEQ ID NO 5
<211> LENGTH: 866
<212> TYPE: PRT
<213> ORGANISM: Artificial Sequence
<220> FEATURE:
<223> OTHER INFORMATION: GST-NoV P-(387)-NoV P-(115) fusion protein

<400> SEQUENCE: 5

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Ser Arg Thr Lys Pro Phe Thr Val Pro Ile Leu Thr Val Glu Glu Met
225                 230                 235                 240

Ser Asn Ser Arg Phe Pro Ile Pro Leu Glu Lys Leu Tyr Thr Gly Pro
```

-continued

```
                245                 250                 255
Ser Ser Ala Phe Val Gln Pro Gln Asn Gly Arg Cys Thr Thr Asp
            260                 265                 270
Gly Val Leu Leu Gly Thr Thr Gln Leu Ser Ala Val Asn Ile Cys Thr
        275                 280                 285
Phe Arg Gly Asp Val Thr His Ile Ala Gly Ser His Asp Tyr Ile Met
        290                 295                 300
Asn Leu Ala Ser Gln Asn Trp Asn Asn Tyr Asp Pro Thr Glu Glu Ile
305                 310                 315                 320
Pro Ala Pro Leu Gly Thr Pro Asp Phe Val Gly Lys Ile Gln Gly Met
                325                 330                 335
Leu Thr Gln Thr Thr Arg Glu Asp Gly Ser Thr Arg Ala His Lys Ala
            340                 345                 350
Thr Val Ser Thr Gly Ser Val His Phe Thr Pro Lys Leu Gly Ser Val
        355                 360                 365
Gln Tyr Thr Thr Asp Thr Asn Asn Asp Leu Gln Thr Gly Gln Asn Thr
        370                 375                 380
Lys Phe Thr Pro Val Gly Val Ile Gln Asp Gly Asn Asn His Gln Asn
385                 390                 395                 400
Glu Pro Gln Gln Trp Val Leu Pro Asn Tyr Ser Gly Arg Thr Gly His
                405                 410                 415
Asn Val His Leu Ala Pro Ala Val Ala Pro Thr Phe Pro Gly Glu Gln
            420                 425                 430
Leu Leu Phe Phe Arg Ser Thr Met Pro Gly Cys Ser Gly Tyr Pro Asn
        435                 440                 445
Met Asn Leu Asp Cys Leu Leu Pro Gln Glu Trp Val Gln His Phe Tyr
        450                 455                 460
Gln Glu Ala Ala Pro Ala Gln Ser Asp Val Ala Leu Leu Arg Phe Val
465                 470                 475                 480
Asn Pro Asp Thr Gly Arg Val Leu Phe Glu Cys Lys Leu His Lys Ser
                485                 490                 495
Gly Tyr Val Thr Val Ala His Thr Gly Pro His Asp Leu Val Ile Pro
            500                 505                 510
Pro Asn Gly Tyr Phe Arg Phe Asp Ser Trp Val Asn Gln Phe Tyr Thr
        515                 520                 525
Leu Ala Pro Met Gly Asn Gly Ala Gly Arg Gly Gly Gly Gly Gly
        530                 535                 540
Gly Gly Gly Gly Gly Gly Gln Lys Thr Lys Pro Phe Ser Val Pro Asn
545                 550                 555                 560
Leu Pro Leu Asn Thr Leu Ser Asn Ser Arg Val Pro Ser Leu Ile Arg
                565                 570                 575
Ser Met Met Val Ser Arg Asp His Gly Gln Met Val Gln Phe Gln Asn
            580                 585                 590
Gly Arg Val Thr Leu Asp Gly Gln Leu Gln Gly Thr Thr Pro Thr Ser
        595                 600                 605
Ala Ser Gln Leu Cys Lys Ile Arg Gly Ser Val Phe His Ala Asn Gly
        610                 615                 620
Gly Asn Gly Tyr Thr Leu Thr Glu Leu Asp Gly Ser Pro Tyr His Ala
625                 630                 635                 640
Phe Glu Ser Pro Ala Pro Ile Gly Phe Pro Asp Leu Gly Glu Cys Asp
                645                 650                 655
Trp His Met Glu Ala Ser Pro Thr Gln Phe Asp Thr Gly Asp Val
            660                 665                 670
```

```
Ile Lys Gln Ile Asn Val Lys Gln Glu Ala Ala Phe Ala Pro His Leu
            675                 680                 685

Gly Thr Ile Gln Ala Asp Gly Leu Ser Asp Val Ser Val Asn Thr Asn
        690                 695                 700

Met Ile Ala Lys Leu Gly Trp Val Ser Pro Ala Ser Asp Gly His Arg
705                 710                 715                 720

Gly Asn Val Asp Pro Trp Val Ile Pro Arg Tyr Gly Ser Thr Leu Thr
                725                 730                 735

Glu Ala Ala Gln Leu Ala Pro Pro Ile Tyr Pro Pro Gly Phe Gly Glu
            740                 745                 750

Ala Ile Val Phe Phe Met Ser Asp Phe Pro Ile Ala His Gly Ala Asn
            755                 760                 765

Gly Leu Ser Val Pro Cys Thr Ile Pro Gln Glu Phe Val Thr His Phe
        770                 775                 780

Val Asn Glu Gln Ala Pro Thr Arg Gly Glu Ala Ala Leu Leu His Tyr
785                 790                 795                 800

Leu Asp Pro Asp Thr His Arg Asn Leu Gly Glu Phe Lys Leu Tyr Pro
                805                 810                 815

Glu Gly Phe Met Thr Cys Val Pro Asn Ser Ser Gly Thr Gly Pro Gln
            820                 825                 830

Thr Leu Pro Ile Asn Gly Val Phe Val Phe Val Ser Trp Val Ser Arg
        835                 840                 845

Phe Tyr Gln Leu Lys Pro Val Gly Thr Ala Gly Pro Ala Arg Ser Leu
850                 855                 860

Gly Ile
865

<210> SEQ ID NO 6
<211> LENGTH: 638
<212> TYPE: PRT
<213> ORGANISM: Artificial Sequence
<220> FEATURE:
<223> OTHER INFORMATION: NoV P- (387)-NoV P- (207)  fusion protein

<400> SEQUENCE: 6

Ser Arg Thr Lys Pro Phe Thr Val Pro Ile Leu Thr Val Glu Glu Met
1               5                   10                  15

Ser Asn Ser Arg Phe Pro Ile Pro Leu Glu Lys Leu Tyr Thr Gly Pro
            20                  25                  30

Ser Ser Ala Phe Val Val Gln Pro Gln Asn Gly Arg Cys Thr Thr Asp
        35                  40                  45

Gly Val Leu Leu Gly Thr Thr Gln Leu Ser Ala Val Asn Ile Cys Thr
    50                  55                  60

Phe Arg Gly Asp Val Thr His Ile Ala Gly Ser His Asp Tyr Ile Met
65                  70                  75                  80

Asn Leu Ala Ser Gln Asn Trp Asn Asn Tyr Asp Pro Thr Glu Glu Ile
                85                  90                  95

Pro Ala Pro Leu Gly Thr Pro Asp Phe Val Gly Lys Ile Gln Gly Met
            100                 105                 110

Leu Thr Gln Thr Thr Arg Glu Asp Gly Ser Thr Arg Ala His Lys Ala
        115                 120                 125

Thr Val Ser Thr Gly Ser Val His Phe Thr Pro Lys Leu Gly Ser Val
    130                 135                 140

Gln Tyr Thr Thr Asp Thr Asn Asn Asp Leu Gln Thr Gly Gln Asn Thr
145                 150                 155                 160
```

-continued

Lys Phe Thr Pro Val Gly Val Ile Gln Asp Gly Asn His Gln Asn
                165                 170                 175

Glu Pro Gln Gln Trp Val Leu Pro Asn Tyr Ser Gly Arg Thr Gly His
            180                 185                 190

Asn Val His Leu Ala Pro Ala Val Ala Pro Thr Phe Pro Gly Glu Gln
        195                 200                 205

Leu Leu Phe Phe Arg Ser Thr Met Pro Gly Cys Ser Gly Tyr Pro Asn
    210                 215                 220

Met Asn Leu Asp Cys Leu Leu Pro Gln Glu Trp Val Gln His Phe Tyr
225                 230                 235                 240

Gln Glu Ala Ala Pro Ala Gln Ser Asp Val Ala Leu Leu Arg Phe Val
                245                 250                 255

Asn Pro Asp Thr Gly Arg Val Leu Phe Glu Cys Lys Leu His Lys Ser
            260                 265                 270

Gly Tyr Val Thr Val Ala His Thr Gly Pro His Asp Leu Val Ile Pro
        275                 280                 285

Pro Asn Gly Tyr Phe Arg Phe Asp Ser Trp Val Asn Gln Phe Tyr Thr
    290                 295                 300

Leu Ala Pro Met Gly Asn Gly Ala Gly Arg Gly Gly Gly Gly Gly Gly
305                 310                 315                 320

Gly Gly Gly Gly Gly Ser Lys Thr Lys Ala Phe Thr Ile Pro Val
                325                 330                 335

Leu Lys Ile Ser Glu Met Thr Asn Ser Arg Phe Pro Val Pro Val Asp
            340                 345                 350

Gln Met Tyr Thr Ser Arg Ser Glu Gly Ile Val Val Gln Pro Gln Asn
        355                 360                 365

Gly Arg Ala Thr Ile Asp Gly Glu Leu Leu Gly Thr Thr Leu Val Ser
    370                 375                 380

Pro Val Ser Val Cys Asn Phe Lys Gly Asn Leu Gln Ala Glu Val Pro
385                 390                 395                 400

Gly Gln His Gln Leu Tyr Gln Leu Gln Leu Thr Asn Leu Asp Gly Ser
                405                 410                 415

Pro Ile Asp Pro Thr Asp Thr Pro Gly Pro Leu Gly Cys Pro Asp
            420                 425                 430

Phe Thr Gly Leu Leu Tyr Gly Val Ala Ser Gln Arg Gly Pro Gly Asp
    435                 440                 445

Ala Thr Arg Ala His Glu Ala Arg Ile Asp Thr Gly Ser Asp Thr Phe
450                 455                 460

Ala Pro Lys Ile Gly Gln Val Arg Phe Tyr Ser Thr Ser Ser Asp Phe
465                 470                 475                 480

Glu Thr Asn Gln Pro Thr His Phe Thr Pro Ile Gly Ile Tyr Ile Glu
                485                 490                 495

Gly Asn Ser Ser Asp Phe Asn Gln Trp Gln Leu Pro Arg Tyr Gly Gly
            500                 505                 510

His Leu Ala Asn Asn His Leu Ala Pro Ala Val Ser Pro Leu Phe
        515                 520                 525

Pro Gly Glu Gln Ile Leu Phe Phe Arg Ser Phe Ile Pro Gly Ala Ser
    530                 535                 540

Gly His Thr Asn Gly Glu Met Asp Cys Leu Leu Pro Gln Glu Phe Val
545                 550                 555                 560

Gln His Phe Tyr Gln Glu Ala Ala Thr Ala Arg Ser Glu Val Ala Leu
                565                 570                 575

```
Leu Arg Phe Val Asn Pro Asp Thr Gly Arg Ala Leu Phe Glu Ser Lys
                580                 585                 590

Leu His Lys Gln Gly Phe Met Thr Ile Ala Ser Ser Gly Asp His Pro
        595                 600                 605

Ile Ile Met Pro Thr Asn Gly Tyr Phe Arg Phe Glu Ala Trp Val Asn
    610                 615                 620

Gln Phe Tyr Ser Leu Ala Pro Val Gly Thr Gly Ser Gly Arg
625                 630                 635

<210> SEQ ID NO 7
<211> LENGTH: 642
<212> TYPE: PRT
<213> ORGANISM: Artificial Sequence
<220> FEATURE:
<223> OTHER INFORMATION: NoV P- (387)-NoV P- (115) fusion protein

<400> SEQUENCE: 7

Ser Arg Thr Lys Pro Phe Thr Val Pro Ile Leu Thr Val Glu Glu Met
1               5                   10                  15

Ser Asn Ser Arg Phe Pro Ile Pro Leu Glu Lys Leu Tyr Thr Gly Pro
            20                  25                  30

Ser Ser Ala Phe Val Val Gln Pro Gln Asn Gly Arg Cys Thr Thr Asp
        35                  40                  45

Gly Val Leu Leu Gly Thr Thr Gln Leu Ser Ala Val Asn Ile Cys Thr
    50                  55                  60

Phe Arg Gly Asp Val Thr His Ile Ala Gly Ser His Asp Tyr Ile Met
65                  70                  75                  80

Asn Leu Ala Ser Gln Asn Trp Asn Asn Tyr Asp Pro Thr Glu Glu Ile
                85                  90                  95

Pro Ala Pro Leu Gly Thr Pro Asp Phe Val Gly Lys Ile Gln Gly Met
            100                 105                 110

Leu Thr Gln Thr Thr Arg Glu Asp Gly Ser Thr Arg Ala His Lys Ala
        115                 120                 125

Thr Val Ser Thr Gly Ser Val His Phe Thr Pro Lys Leu Gly Ser Val
    130                 135                 140

Gln Tyr Thr Thr Asp Thr Asn Asn Asp Leu Gln Thr Gly Gln Asn Thr
145                 150                 155                 160

Lys Phe Thr Pro Val Gly Val Ile Gln Asp Gly Asn Asn His Gln Asn
                165                 170                 175

Glu Pro Gln Gln Trp Val Leu Pro Asn Tyr Ser Gly Arg Thr Gly His
            180                 185                 190

Asn Val His Leu Ala Pro Ala Val Ala Pro Thr Phe Pro Gly Glu Gln
        195                 200                 205

Leu Leu Phe Phe Arg Ser Thr Met Pro Gly Cys Ser Gly Tyr Pro Asn
    210                 215                 220

Met Asn Leu Asp Cys Leu Leu Pro Gln Glu Trp Val Gln His Phe Tyr
225                 230                 235                 240

Gln Glu Ala Ala Pro Ala Gln Ser Asp Val Ala Leu Leu Arg Phe Val
                245                 250                 255

Asn Pro Asp Thr Gly Arg Val Leu Phe Glu Cys Lys Leu His Lys Ser
            260                 265                 270

Gly Tyr Val Thr Val Ala His Thr Gly Pro His Asp Leu Val Ile Pro
        275                 280                 285

Pro Asn Gly Tyr Phe Arg Phe Asp Ser Trp Val Asn Gln Phe Tyr Thr
    290                 295                 300
```

```
Leu Ala Pro Met Gly Asn Gly Ala Gly Arg Gly Gly Gly Gly Gly
305                 310                 315                 320

Gly Gly Gly Gly Gly

```
                    20                  25                  30
Tyr Glu Arg Asp Glu Gly Asp Lys Trp Arg Asn Lys Lys Phe Glu Leu
                35                  40                  45
Gly Leu Glu Phe Pro Asn Leu Pro Tyr Tyr Ile Asp Gly Asp Val Lys
            50                  55                  60
Leu Thr Gln Ser Met Ala Ile Ile Arg Tyr Ile Ala Asp Lys His Asn
65                  70                  75                  80
Met Leu Gly Gly Cys Pro Lys Glu Arg Ala Glu Ile Ser Met Leu Glu
                85                  90                  95
Gly Ala Val Leu Asp Ile Arg Tyr Gly Val Ser Arg Ile Ala Tyr Ser
                100                 105                 110
Lys Asp Phe Glu Thr Leu Lys Val Asp Phe Leu Ser Lys Leu Pro Glu
            115                 120                 125
Met Leu Lys Met Phe Glu Asp Arg Leu Cys His Lys Thr Tyr Leu Asn
            130                 135                 140
Gly Asp His Val Thr His Pro Asp Phe Met Leu Tyr Asp Ala Leu Asp
145                 150                 155                 160
Val Val Leu Tyr Met Asp Pro Met Cys Leu Asp Ala Phe Pro Lys Leu
                165                 170                 175
Val Cys Phe Lys Lys Arg Ile Glu Ala Ile Pro Gln Ile Asp Lys Tyr
                180                 185                 190
Leu Lys Ser Ser Lys Tyr Ile Ala Trp Pro Leu Gln Gly Trp Gln Ala
            195                 200                 205
Thr Phe Gly Gly Gly Asp His Pro Pro Lys Ser Asp Leu Val Pro Arg
            210                 215                 220
Ser Arg Thr Lys Pro Phe Thr Val Pro Ile Leu Thr Val Glu Glu Met
225                 230                 235                 240
Ser Asn Ser Arg Phe Pro Ile Pro Leu Glu Lys Leu Tyr Thr Gly Pro
                245                 250                 255
Ser Ser Ala Phe Val Val Gln Pro Gln Asn Gly Arg Cys Thr Thr Asp
                260                 265                 270
Gly Val Leu Leu Gly Thr Thr Gln Leu Ser Ala Val Asn Ile Cys Thr
            275                 280                 285
Phe Arg Gly Asp Val Thr His Ile Ala Gly Ser His Asp Tyr Ile Met
            290                 295                 300
Asn Leu Ala Ser Gln Asn Trp Asn Asn Tyr Asp Pro Thr Glu Glu Ile
305                 310                 315                 320
Pro Ala Pro Leu Gly Thr Pro Asp Phe Val Gly Lys Ile Gln Gly Met
                325                 330                 335
Leu Thr Gln Thr Thr Arg Glu Asp Gly Ser Thr Arg Ala His Lys Ala
            340                 345                 350
Thr Val Ser Thr Gly Thr Val His Phe Thr Pro Lys Leu Gly Ser Val
            355                 360                 365
Gln Tyr Thr Thr Ser Leu Asp Gly Pro Tyr Gln Pro Thr Thr Phe Thr
            370                 375                 380
Pro Pro Thr Asp Tyr Trp Ile Leu Ile Asn Ser Asn Thr Asn Gly Val
385                 390                 395                 400
Val Tyr Glu Ser Thr Asn Asn Ser Asp Phe Trp Thr Ala Val Ile Ala
                405                 410                 415
Val Glu Pro His Val Asn Pro Val Asp Arg Gln Tyr Asn Val Phe Gly
                420                 425                 430
Glu Asn Lys Gln Phe Asn Val Arg Asn Asp Ser Asp Lys Trp Lys Phe
            435                 440                 445
```

```
Leu Glu Met Phe Arg Gly Ser Ser Gln Asn Asp Phe Tyr Asn Arg Arg
    450                 455                 460

Thr Leu Thr Ser Asp Thr Arg Leu Val Gly Ile Leu Lys Tyr Gly Gly
465                 470                 475                 480

Arg Ile Trp Thr Phe His Gly Glu Thr Pro Arg Ala Thr Thr Asp Ser
                485                 490                 495

Ser Asn Thr Ala Asn Leu Asn Gly Ile Ser Ile Thr Ile His Ser Glu
                500                 505                 510

Phe Tyr Ile Ile Pro Arg Ser Gln Glu Ser Lys Cys Asn Glu Tyr Ile
            515                 520                 525

Asn Asn Gly Leu Ile Asp Ile Leu Gln Thr Gly Gln Asn Thr Lys Phe
530                 535                 540

Thr Pro Val Gly Val Ile Gln Asp Gly Asn Asn His Gln Asn Glu Pro
545                 550                 555                 560

Gln Gln Trp Val Leu Pro Asn Tyr Ser Gly Arg Thr Gly His Asn Val
                565                 570                 575

His Leu Ala Pro Ala Val Ala Pro Thr Phe Pro Gly Glu Gln Leu Leu
                580                 585                 590

Phe Phe Arg Ser Thr Met Pro Gly Cys Ser Gly Tyr Pro Asn Met Asn
            595                 600                 605

Leu Asp Cys Leu Leu Pro Gln Glu Trp Val Gln His Phe Tyr Gln Glu
610                 615                 620

Ala Ala Pro Ala Gln Ser Asp Val Ala Leu Leu Arg Phe Val Asn Pro
625                 630                 635                 640

Asp Thr Gly Arg Val Leu Phe Glu Cys Lys Leu His Lys Ser Gly Tyr
                645                 650                 655

Val Thr Val Ala His Thr Gly Pro His Asp Leu Val Ile Pro Pro Asn
                660                 665                 670

Gly Tyr Phe Arg Phe Asp Ser Trp Val Asn Gln Phe Tyr Thr Leu Ala
            675                 680                 685

Pro Met Gly Asn Gly Ala Gly Arg
    690                 695

<210> SEQ ID NO 9
<211> LENGTH: 709
<212> TYPE: PRT
<213> ORGANISM: Artificial Sequence
<220> FEATURE:
<223> OTHER INFORMATION: GST-NoV P--VP8* (C-end)

<400> SEQUENCE: 9

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
                20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
        50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
                100                 105                 110
```

```
Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Leu Val Pro Arg
210                 215                 220

Ser Arg Thr Lys Pro Phe Thr Val Pro Ile Leu Thr Val Glu Glu Met
225                 230                 235                 240

Ser Asn Ser Arg Phe Pro Ile Pro Leu Glu Lys Leu Tyr Thr Gly Pro
                245                 250                 255

Ser Ser Ala Phe Val Val Gln Pro Gln Asn Gly Arg Cys Thr Thr Asp
                260                 265                 270

Gly Val Leu Leu Gly Thr Thr Gln Leu Ser Ala Val Asn Ile Cys Thr
            275                 280                 285

Phe Arg Gly Asp Val Thr His Ile Ala Gly Ser His Asp Tyr Ile Met
290                 295                 300

Asn Leu Ala Ser Gln Asn Trp Asn Asn Tyr Asp Pro Thr Glu Glu Ile
305                 310                 315                 320

Pro Ala Pro Leu Gly Thr Pro Asp Phe Val Gly Lys Ile Gln Gly Met
                325                 330                 335

Leu Thr Gln Thr Thr Arg Glu Asp Gly Ser Thr Arg Ala His Lys Ala
            340                 345                 350

Thr Val Ser Thr Gly Ser Val His Phe Thr Pro Lys Leu Gly Ser Val
            355                 360                 365

Gln Tyr Thr Thr Asp Thr Asn Asn Asp Leu Gln Thr Gly Gln Asn Thr
370                 375                 380

Lys Phe Thr Pro Val Gly Val Ile Gln Asp Gly Asn Asn His Gln Asn
385                 390                 395                 400

Glu Pro Gln Gln Trp Val Leu Pro Asn Tyr Ser Gly Arg Thr Gly His
                405                 410                 415

Asn Val His Leu Ala Pro Ala Val Ala Pro Thr Phe Pro Gly Glu Gln
                420                 425                 430

Leu Leu Phe Phe Arg Ser Thr Met Pro Gly Cys Ser Gly Tyr Pro Asn
            435                 440                 445

Met Asn Leu Asp Cys Leu Leu Pro Gln Glu Trp Val Gln His Phe Tyr
450                 455                 460

Gln Glu Ala Ala Pro Ala Gln Ser Asp Val Ala Leu Leu Arg Phe Val
465                 470                 475                 480

Asn Pro Asp Thr Gly Arg Val Leu Phe Glu Cys Lys Leu His Lys Ser
                485                 490                 495

Gly Tyr Val Thr Val Ala His Thr Gly Pro His Asp Leu Val Ile Pro
                500                 505                 510

Pro Asn Gly Tyr Phe Arg Phe Asp Ser Trp Val Asn Gln Phe Tyr Thr
            515                 520                 525
```

```
Leu Ala Pro Met Gly Asn Gly Ala Gly Arg Gly Gly Gly Gly
530                 535                 540
Gly Gly Gly Gly Gly Gly Leu Asp Gly Pro Tyr Gln Pro Thr Thr Phe
545                 550                 555                 560
Thr Pro Pro Thr Asp Tyr Trp Ile Leu Ile Asn Ser Asn Thr Asn Gly
                565                 570                 575
Val Val Tyr Glu Ser Thr Asn Asn Ser Asp Phe Trp Thr Ala Val Ile
            580                 585                 590
Ala Val Glu Pro His Val Asn Pro Val Asp Arg Gln Tyr Asn Val Phe
            595                 600                 605
Gly Glu Asn Lys Gln Phe Asn Val Arg Asn Asp Ser Asp Lys Trp Lys
610                 615                 620
Phe Leu Glu Met Phe Arg Gly Ser Ser Gln Asn Asp Phe Tyr Asn Arg
625                 630                 635                 640
Arg Thr Leu Thr Ser Asp Thr Arg Leu Val Gly Ile Leu Lys Tyr Gly
                645                 650                 655
Gly Arg Ile Trp Thr Phe His Gly Glu Thr Pro Arg Ala Thr Thr Asp
                660                 665                 670
Ser Ser Asn Thr Ala Asn Leu Asn Gly Ile Ser Ile Thr Ile His Ser
            675                 680                 685
Glu Phe Tyr Ile Ile Pro Arg Ser Gln Glu Ser Lys Cys Asn Glu Tyr
690                 695                 700
Ile Asn Asn Gly Leu
705

<210> SEQ ID NO 10
<211> LENGTH: 560
<212> TYPE: PRT
<213> ORGANISM: Artificial Sequence
<220> FEATURE:
<223> OTHER INFORMATION: GST-NoV P--M2e (loop 2)

<400> SEQUENCE: 10

Met Ser Pro Ile Leu Gly Tyr Trp Lys Ile Lys Gly Leu Val Gln Pro
1               5                   10                  15
Thr Arg Leu Leu Leu Glu Tyr Leu Glu Glu Lys Tyr Glu Glu His Leu
            20                  25                  30
Tyr Glu Arg Asp Glu Gly Asp Lys Trp Arg Asn L

```
Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Ser Arg Thr Lys Pro Phe Thr Val Pro Ile Leu Thr Val Glu Glu Met
225                 230                 235                 240

Ser Asn Ser Arg Phe Pro Ile Pro Leu Glu Lys Leu Tyr Thr Gly Pro
                245                 250                 255

Ser Ser Ala Phe Val Val Gln Pro Gln Asn Gly Arg Cys Thr Thr Asp
            260                 265                 270

Gly Val Leu Leu Gly Thr Thr Gln Leu Ser Ala Val Asn Ile Cys Thr
        275                 280                 285

Phe Arg Gly Asp Val Thr His Ile Ala Gly Ser His Asp Tyr Ile Met
    290                 295                 300

Asn Leu Ala Ser Gln Asn Trp Asn Asn Tyr Asp Pro Thr Glu Glu Ile
305                 310                 315                 320

Pro Ala Pro Leu Gly Thr Pro Asp Phe Val Gly Lys Ile Gln Gly Met
                325                 330                 335

Leu Thr Gln Thr Thr Arg Glu Asp Gly Ser Thr Arg Ala His Lys Ala
            340                 345                 350

Thr Val Ser Thr Gly Thr Val His Phe Thr Pro Lys Leu Gly Ser Val
        355                 360                 365

Gln Tyr Thr Thr Ser Ser Leu Leu Thr Glu Val Glu Thr Pro Ile Arg
    370                 375                 380

Asn Glu Trp Gly Cys Arg Cys Asn Asp Ser Ser Asp Ile Asp Ile Leu
385                 390                 395                 400

Gln Thr Gly Gln Asn Thr Lys Phe Thr Pro Val Gly Val Ile Gln Asp
                405                 410                 415

Gly Asn Asn His Gln Asn Glu Pro Gln Gln Trp Val Leu Pro Asn Tyr
            420                 425                 430

Ser Gly Arg Thr Gly His Asn Val His Leu Ala Pro Ala Val Ala Pro
        435                 440                 445

Thr Phe Pro Gly Glu Gln Leu Leu Phe Phe Arg Ser Thr Met Pro Gly
    450                 455                 460

Cys Ser Gly Tyr Pro Asn Met Asn Leu Asp Cys Leu Leu Pro Gln Glu
465                 470                 475                 480

Trp Val Gln His Phe Tyr Gln Glu Ala Ala Pro Ala Gln Ser Asp Val
                485                 490                 495

Ala Leu Leu Arg Phe Val Asn Pro Asp Thr Gly Arg Val Leu Phe Glu
            500                 505                 510

Cys Lys Leu His Lys Ser Gly Tyr Val Thr Val Ala His Thr Gly Pro
        515                 520                 525

His Asp Leu Val Ile Pro Pro Asn Gly Tyr Phe Arg Phe Asp Ser Trp
    530                 535                 540

Val Asn Gln Phe Tyr Thr Leu Ala Pro Met Gly Asn Gly Ala Gly Arg
545                 550                 555                 560

<210> SEQ ID NO 11
<211> LENGTH: 485
<212> TYPE: PRT
<213> ORGANISM: Artificial Sequence
<220> FEATURE:
<223> OTHER INFORMATION: NoV P- -VP8* (C-end)
```

<400> SEQUENCE: 11

```
Ser Arg Thr Lys Pro Phe Thr Val Pro Ile Leu Thr Val Glu Met
1               5                   10                  15

Ser Asn Ser Arg Phe Pro Ile Pro Leu Glu Lys Leu Tyr Thr Gly Pro
            20                  25                  30

Ser Ser Ala Phe Val Val Gln Pro Gln Asn Gly Arg Cys Thr Thr Asp
        35                  40                  45

Gly Val Leu Leu Gly Thr Thr Gln Leu Ser Ala Val Asn Ile Cys Thr
    50                  55                  60

Phe Arg Gly Asp Val Thr His Ile Ala Gly Ser His Asp Tyr Ile Met
65                  70                  75                  80

Asn Leu Ala Ser Gln Asn Trp Asn Asn Tyr Asp Pro Thr Glu Glu Ile
                85                  90                  95

Pro Ala Pro Leu Gly Thr Pro Asp Phe Val Gly Lys Ile Gln Gly Met
            100                 105                 110

Leu Thr Gln Thr Thr Arg Glu Asp Gly Ser Thr Arg Ala His Lys Ala
        115                 120                 125

Thr Val Ser Thr Gly Ser Val His Phe Thr Pro Lys Leu Gly Ser Val
130                 135                 140

Gln Tyr Thr Thr Asp Thr Asn Asn Asp Leu Gln Thr Gly Gln Asn Thr
145                 150                 155                 160

Lys Phe Thr Pro Val Gly Val Ile Gln Asp Gly Asn Asn His Gln Asn
                165                 170                 175

Glu Pro Gln Gln Trp Val Leu Pro Asn Tyr Ser Gly Arg Thr Gly His
            180                 185                 190

Asn Val His Leu Ala Pro Ala Val Ala Pro Thr Phe Pro Gly Glu Gln
        195                 200                 205

Leu Leu Phe Phe Arg Ser Thr Met Pro Gly Cys Ser Gly Tyr Pro Asn
    210                 215                 220

Met Asn Leu Asp Cys Leu Leu Pro Gln Glu Trp Val Gln His Phe Tyr
225                 230                 235                 240

Gln Glu Ala Ala Pro Ala Gln Ser Asp Val Ala Leu Leu Arg Phe Val
                245                 250                 255

Asn Pro Asp Thr Gly Arg Val Leu Phe Glu Cys Lys Leu His Lys Ser
            260                 265                 270

Gly Tyr Val Thr Val Ala His Thr Gly Pro His Asp Leu Val Ile Pro
        275                 280                 285

Pro Asn Gly Tyr Phe Arg Phe Asp Ser Trp Val Asn Gln Phe Tyr Thr
    290                 295                 300

Leu Ala Pro Met Gly Asn Gly Ala Gly Arg Gly Gly Gly Gly Gly Gly
305                 310                 315                 320

Gly Gly Gly Gly Gly Leu Asp Gly Pro Tyr Gln Pro Thr Thr Phe
                325                 330                 335

Thr Pro Pro Thr Asp Tyr Trp Ile Leu Ile Asn Ser Thr Asn Gly
            340                 345                 350

Val Val Tyr Glu Ser Thr Asn Asn Ser Asp Phe Trp Thr Ala Val Ile
        355                 360                 365

Ala Val Glu Pro His Val Asn Pro Val Asp Arg Gln Tyr Asn Val Phe
    370                 375                 380

Gly Glu Asn Lys Gln Phe Asn Val Arg Asn Asp Ser Asp Lys Trp Lys
385                 390                 395                 400

Phe Leu Glu Met Phe Arg Gly Ser Ser Gln Asn Asp Phe Tyr Asn Arg
```

```
                405                 410                 415
Arg Thr Leu Thr Ser Asp Thr Arg Leu Val Gly Ile Leu Lys Tyr Gly
            420                 425                 430

Gly Arg Ile Trp Thr Phe His Gly Glu Thr Pro Arg Ala Thr Thr Asp
        435                 440                 445

Ser Ser Asn Thr Ala Asn Leu Asn Gly Ile Ser Ile Thr Ile His Ser
    450                 455                 460

Glu Phe Tyr Ile Ile Pro Arg Ser Gln Glu Ser Lys Cys Asn Glu Tyr
465                 470                 475                 480

Ile Asn Asn Gly Leu
                485

<210> SEQ ID NO 12
<211> LENGTH: 336
<212> TYPE: PRT
<213> ORGANISM: Artificial Sequence
<220> FEATURE:
<223> OTHER INFORMATION: NoV P--M2e

<400> SEQUENCE: 12

Ser Arg Thr Lys Pro Phe Thr Val Pro Ile Leu Thr Val Gl

```
                275                 280                 285
Cys Lys Leu His Lys Ser Gly Tyr Val Thr Val Ala His Thr Gly Pro
            290                 295                 300
His Asp Leu Val Ile Pro Pro Asn Gly Tyr Phe Arg Phe Asp Ser Trp
305                 310                 315                 320
Val Asn Gln Phe Tyr Thr Leu Ala Pro Met Gly Asn Gly Ala Gly Arg
                325                 330                 335

<210> SEQ ID NO 13
<211> LENGTH: 778
<212> TYPE: PRT
<213> ORGANISM: Artificial Sequence
<220> FEATURE:
<223> OTHER INFORMATION: GST-NoV P-GST

<400> SEQUENCE: 13

Met Ser Pro Ile Leu Gly Tyr Trp Lys Ile Lys Gly Leu Val Gln Pro
1               5                   10                  15
Thr Arg Leu Leu Leu Glu Tyr Leu Glu Glu Lys Tyr Glu Glu His Leu
            20                  25                  30
Tyr Glu Arg Asp Glu Gly Asp Lys Trp Arg Asn Lys Lys Phe Glu Leu
        35                  40                  45
Gly Leu Glu Phe Pro Asn Leu Pro Tyr Tyr Ile Asp Gly Asp Val Lys
    50                  55                  60
Leu Thr Gln Ser Met Ala Ile Ile Arg Tyr Ile Ala Asp Lys His Asn
65                  70                  75                  80
Met Leu Gly Gly Cys Pro Lys Glu Arg Ala Glu Ile Ser Met Leu Glu
                85                  90                  95
Gly Ala Val Leu Asp Ile Arg Tyr Gly Val Ser Arg Ile Ala Tyr Ser
            100                 105                 110
Lys Asp Phe Glu Thr Leu Lys Val Asp Phe Leu Ser Lys Leu Pro Glu
        115                 120                 125
Met Leu Lys Met Phe Glu Asp Arg Leu Cys His Lys Thr Tyr Leu Asn
    130                 135                 140
Gly Asp His Val Thr His Pro Asp Phe Met Leu Tyr Asp Ala Leu Asp
145                 150                 155                 160
Val Val Leu Tyr Met Asp Pro Met Cys Leu Asp Ala Phe Pro Lys Leu
                165                 170                 175
Val Cys Phe Lys Lys Arg Ile Glu Ala Ile Pro Gln Ile Asp Lys Tyr
            180                 185                 190
Leu Lys Ser Ser Lys Tyr Ile Ala Trp Pro Leu Gln Gly Trp Gln Ala
        195                 200                 205
Thr Phe Gly Gly Gly Asp His Pro Pro Lys Ser Asp Leu Val Pro Arg
    210                 215                 220
Ser Arg Thr Lys Pro Phe Thr Val Pro Ile Leu Thr Val Glu Glu Met
225                 230                 235                 240
Ser Asn Ser Arg Phe Pro Ile Pro Leu Glu Lys Leu Tyr Thr Gly Pro
                245                 250                 255
Ser Ser Ala Phe Val Val Gln Pro Gln Asn Gly Arg Cys Thr Thr Asp
            260                 265                 270
Gly Val Leu Leu Gly Thr Thr Gln Leu Ser Ala Val Asn Ile Cys Thr
        275                 280                 285
Phe Arg Gly Asp Val Thr His Ile Ala Gly Ser His Asp Tyr Ile Met
    290                 295                 300
Asn Leu Ala Ser Gln Asn Trp Asn Asn Tyr Asp Pro Thr Glu Glu Ile
```

```
                305                 310                 315                 320
            Pro Ala Pro Leu Gly Thr Pro Asp Phe Val Gly Lys Ile Gln Gly Met
                            325                 330                 335
            Leu Thr Gln Thr Thr Arg Glu Asp Gly Ser Thr Arg Ala His Lys Ala
                            340                 345                 350
            Thr Val Ser Thr Gly Ser Val His Phe Thr Pro Lys Leu Gly Ser Val
                            355                 360                 365
            Gln Tyr Thr Thr Asp Thr Asn Asn Asp Leu Gln Thr Gly Gln Asn Thr
                        370                 375                 380
            Lys Phe Thr Pro Val Gly Val Ile Gln Asp Gly Asn Asn His Gln Asn
            385                 390                 395                 400
            Glu Pro Gln Gln Trp Val Leu Pro Asn Tyr Ser Gly Arg Thr Gly His
                            405                 410                 415
            Asn Val His Leu Ala Pro Ala Val Ala Pro Thr Phe Pro Gly Glu Gln
                            420                 425                 430
            Leu Leu Phe Phe Arg Ser Thr Met Pro Gly Cys Ser Gly Tyr Pro Asn
                            435                 440                 445
            Met Asn Leu Asp Cys Leu Leu Pro Gln Glu Trp Val Gln His Phe Tyr
                        450                 455                 460
            Gln Glu Ala Ala Pro Ala Gln Ser Asp Val Ala Leu Leu Arg Phe Val
            465                 470                 475                 480
            Asn Pro Asp Thr Gly Arg Val Leu Phe Glu Cys Lys Leu His Lys Ser
                            485                 490                 495
            Gly Tyr Val Thr Val Ala His Thr Gly Pro His Asp Leu Val Ile Pro
                            500                 505                 510
            Pro Asn Gly Tyr Phe Arg Phe Asp Ser Trp Val Asn Gln Phe Tyr Thr
                            515                 520                 525
            Leu Ala Pro Met Gly Asn Gly Ala Gly Arg Arg Ala Leu Gly Gly
                        530                 535                 540
            Gly Gly Gly Gly Gly Gly Gly Gly Met Ser Pro Ile Leu Gly
            545                 550                 555                 560
            Tyr Trp Lys Ile Lys Gly Leu Val Gln Pro Thr Arg Leu Leu Leu Glu
                            565                 570                 575
            Tyr Leu Glu Glu Lys Tyr Glu Glu His Leu Tyr Glu Arg Asp Glu Gly
                            580                 585                 590
            Asp Lys Trp Arg Asn Lys Lys Phe Glu Leu Gly Leu Glu Phe Pro Asn
                        595                 600                 605
            Leu Pro Tyr Tyr Ile Asp Gly Asp Val Lys Leu Thr Gln Ser Met Ala
                        610                 615                 620
            Ile Ile Arg Tyr Ile Ala Asp Lys His Asn Met Leu Gly Gly Cys Pro
            625                 630                 635                 640
            Lys Glu Arg Ala Glu Ile Ser Met Leu Glu Gly Ala Val Leu Asp Ile
                            645                 650                 655
            Arg Tyr Gly Val Ser Arg Ile Ala Tyr Ser Lys Asp Phe Glu Thr Leu
                            660                 665                 670
            Lys Val Asp Phe Leu Ser Lys Leu Pro Glu Met Leu Lys Met Phe Glu
                            675                 680                 685
            Asp Arg Leu Cys His Lys Thr Tyr Leu Asn Gly Asp His Val Thr His
                        690                 695                 700
            Pro Asp Phe Met Leu Tyr Asp Ala Leu Asp Val Val Leu Tyr Met Asp
            705                 710                 715                 720
            Pro Met Cys Leu Asp Ala Phe Pro Lys Leu Val Cys Phe Lys Lys Arg
                            725                 730                 735
```

-continued

Ile Glu Ala Ile Pro Gln Ile Asp Lys Tyr Leu Lys Ser Ser Lys Tyr
            740                 745                 750

Ile Ala Trp Pro Leu Gln Gly Trp Gln Ala Thr Phe Gly Gly Gly Asp
            755                 760                 765

His Pro Pro Lys Ser Asp Leu Val Pro Arg
            770                 775

<210> SEQ ID NO 14
<211> LENGTH: 709
<212> TYPE: PRT
<213> ORGANISM: Artificial Sequence
<220> FEATURE:
<223> OTHER INFORMATION: GST-NoV P- - HEV P

<400> SEQUENCE: 14

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Ser Arg Thr Lys Pro Phe Thr Val Pro Ile Leu Thr Val Glu Glu Met
225                 230                 235                 240

Ser Asn Ser Arg Phe Pro Ile Pro Leu Glu Lys Leu Tyr Thr Gly Pro
                245                 250                 255

Ser Ser Ala Phe Val Val Gln Pro Gln Asn Gly Arg Cys Thr Thr Asp
            260                 265                 270

Gly Val Leu Leu Gly Thr Thr Gln Leu Ser Ala Val Asn Ile Cys Thr
        275                 280                 285

Phe Arg Gly Asp Val Thr His Ile Ala Gly Ser His Asp Tyr Ile Met
    290                 295                 300

Asn Leu Ala Ser Gln Asn Trp Asn Asn Tyr Asp Pro Thr Glu Glu Ile
305                 310                 315                 320

```
Pro Ala Pro Leu Gly Thr Pro Asp Phe Val Gly Lys Ile Gln Gly Met
            325                 330                 335

Leu Thr Gln Thr Thr Arg Glu Asp Gly Ser Thr Arg Ala His Lys Ala
            340                 345                 350

Thr Val Ser Thr Gly Ser Val His Phe Thr Pro Lys Leu Gly Ser Val
            355                 360                 365

Gln Tyr Thr Thr Asp Thr Asn Asn Asp Leu Gln Thr Gly Gln Asn Thr
        370                 375                 380

Lys Phe Thr Pro Val Gly Val Ile Gln Asp Gly Asn Asn His Gln Asn
385                 390                 395                 400

Glu Pro Gln Gln Trp Val Leu Pro Asn Tyr Ser Gly Arg Thr Gly His
            405                 410                 415

Asn Val His Leu Ala Pro Ala Val Ala Pro Thr Phe Pro Gly Glu Gln
            420                 425                 430

Leu Leu Phe Phe Arg Ser Thr Met Pro Gly Cys Ser Gly Tyr Pro Asn
            435                 440                 445

Met Asn Leu Asp Cys Leu Leu Pro Gln Glu Trp Val Gln His Phe Tyr
        450                 455                 460

Gln Glu Ala Ala Pro Ala Gln Ser Asp Val Ala Leu Leu Arg Phe Val
465                 470                 475                 480

Asn Pro Asp Thr Gly Arg Val Leu Phe Glu Cys Lys Leu His Lys Ser
            485                 490                 495

Gly Tyr Val Thr Val Ala His Thr Gly Pro His Asp Leu Val Ile Pro
            500                 505                 510

Pro Asn Gly Tyr Phe Arg Phe Asp Ser Trp Val Asn Gln Phe Tyr Thr
            515                 520                 525

Leu Ala Pro Met Gly Asn Gly Ala Gly Arg Gly Gly Gly Gly Gly Gly
            530                 535                 540

Thr Pro Ser Pro Ala Pro Ser Arg Pro Phe Ser Val Leu Arg Ala Asn
545                 550                 555                 560

Asp Val Leu Trp Leu Ser Leu Thr Ala Ala Glu Tyr Asp Gln Thr Thr
            565                 570                 575

Tyr Gly Ser Ser Thr Asn Pro Met Tyr Val Ser Asp Thr Val Thr Phe
            580                 585                 590

Val Asn Val Ala Thr Gly Ala Gln Ala Val Ala Arg Ser Leu Asp Trp
            595                 600                 605

Ser Lys Val Thr Leu Asp Gly Arg Pro Leu Thr Thr Ile Gln Gln Tyr
610                 615                 620

Ser Lys Thr Phe Tyr Val Leu Pro Leu Arg Gly Lys Leu Ser Phe Trp
625                 630                 635                 640

Glu Ala Ser Thr Thr Lys Ala Gly Tyr Pro Tyr Asn Tyr Asn Thr Thr
            645                 650                 655

Ala Ser Asp Gln Ile Leu Ile Glu Asn Ala Ala Gly His Arg Val Ala
            660                 665                 670

Ile Ser Thr Tyr Thr Thr Ser Leu Gly Ala Gly Pro Thr Ser Ile Ser
            675                 680                 685

Ala Val Gly Val Leu Ala Pro His Ser Ala Leu Ala Ala Leu Glu Asp
            690                 695                 700

Thr Val Asp Tyr Pro
705

<210> SEQ ID NO 15
<211> LENGTH: 485
```

<212> TYPE: PRT
<213> ORGANISM: Artificial Sequence
<220> FEATURE:
<223> OTHER INFORMATION: NoV P- -HEV P

<400> SEQUENCE: 15

```
Ser Arg Thr Lys Pro Phe Thr Val Pro Ile Leu Thr Val Glu Met
1               5                   10                  15

Ser Asn Ser Arg Phe Pro Ile Pro Leu Glu Lys Leu Tyr Thr Gly Pro
            20                  25                  30

Ser Ser Ala Phe Val Val Gln Pro Gln Asn Gly Arg Cys Thr Thr Asp
            35                  40                  45

Gly Val Leu Leu Gly Thr Thr Gln Leu Ser Ala Val Asn Ile Cys Thr
    50                  55                  60

Phe Arg Gly Asp Val Thr His Ile Ala Gly Ser His Asp Tyr Ile Met
65                  70                  75                  80

Asn Leu Ala Ser Gln Asn Trp Asn Asn Tyr Asp Pro Thr Glu Glu Ile
                85                  90                  95

Pro Ala Pro Leu Gly Thr Pro Asp Phe Val Gly Lys Ile Gln Gly Met
            100                 105                 110

Leu Thr Gln Thr Thr Arg Glu Asp Gly Ser Thr Arg Ala His Lys Ala
            115                 120                 125

Thr Val Ser Thr Gly Ser Val His Phe Thr Pro Lys Leu Gly Ser Val
130                 135                 140

Gln Tyr Thr Thr Asp Thr Asn Asn Asp Leu Gln Thr Gly Gln Asn Thr
145                 150                 155                 160

Lys Phe Thr Pro Val Gly Val Ile Gln Asp Gly Asn Asn His Gln Asn
                165                 170                 175

Glu Pro Gln Gln Trp Val Leu Pro Asn Tyr Ser Gly Arg Thr Gly His
            180                 185                 190

Asn Val His Leu Ala Pro Ala Val Ala Pro Thr Phe Pro Gly Glu Gln
            195                 200                 205

Leu Leu Phe Phe Arg Ser Thr Met Pro Gly Cys Ser Gly Tyr Pro Asn
210                 215                 220

Met Asn Leu Asp Cys Leu Leu Pro Gln Glu Trp Val Gln His Phe Tyr
225                 230                 235                 240

Gln Glu Ala Ala Pro Ala Gln Ser Asp Val Ala Leu Leu Arg Phe Val
                245                 250                 255

Asn Pro Asp Thr Gly Arg Val Leu Phe Glu Cys Lys Leu His Lys Ser
            260                 265                 270

Gly Tyr Val Thr Val Ala His Thr Gly Pro His Asp Leu Val Ile Pro
            275                 280                 285

Pro Asn Gly Tyr Phe Arg Phe Asp Ser Trp Val Asn Gln Phe Tyr Thr
290                 295                 300

Leu Ala Pro Met Gly Asn Gly Ala Gly Arg Gly Gly Gly Gly Gly Gly
305                 310                 315                 320

Thr Pro Ser Pro Ala Pro Ser Arg Pro Phe Ser Val Leu Arg Ala Asn
                325                 330                 335

Asp Val Leu Trp Leu Ser Leu Thr Ala Ala Glu Tyr Asp Gln Thr Thr
            340                 345                 350

Tyr Gly Ser Ser Thr Asn Pro Met Tyr Val Ser Asp Thr Val Thr Phe
            355                 360                 365

Val Asn Val Ala Thr Gly Ala Gln Ala Val Ala Arg Ser Leu Asp Trp
    370                 375                 380
```

Ser Lys Val Thr Leu Asp Gly Arg Pro Leu Thr Thr Ile Gln Gln Tyr
385                 390                 395                 400

Ser Lys Thr Phe Tyr Val Leu Pro Leu Arg Gly Lys Leu Ser Phe Trp
                405                 410                 415

Glu Ala Ser Thr Thr Lys Ala Gly Tyr Pro Tyr Asn Tyr Asn Thr Thr
            420                 425                 430

Ala Ser Asp Gln Ile Leu Ile Glu Asn Ala Ala Gly His Arg Val Ala
        435                 440                 445

Ile Ser Thr Tyr Thr Thr Ser Leu Gly Ala Gly Pro Thr Ser Ile Ser
    450                 455                 460

Ala Val Gly Val Leu Ala Pro His Ser Ala Leu Ala Ala Leu Glu Asp
465                 470                 475                 480

Thr Val Asp Tyr Pro
            485

<210> SEQ ID NO 16
<211> LENGTH: 174
<212> TYPE: PRT
<213> ORGANISM: Artificial Sequence
<220> FEATURE:
<223> OTHER INFORMATION: HEV P protein

<400> SEQUENCE: 16

Thr Pro Ser Pro Ala Pro Ser Arg Pro Phe Ser Val Leu Arg Ala Asn
1               5                   10                  15

Asp Val Leu Trp Leu Ser Leu Thr Ala Ala Glu Tyr Asp Gln Thr Thr
            20                  25                  30

Tyr Gly Ser Ser Thr Asn Pro Met Tyr Val Ser Asp Thr Val Thr Phe
        35                  40                  45

Val Asn Val Ala Thr Gly Ala Gln Ala Val Ala Arg Ser Leu Asp Trp
    50                  55                  60

Ser Lys Val Thr Leu Asp Gly Arg Pro Leu Thr Thr Ile Gln Gln Tyr
65                  70                  75                  80

Ser Lys Thr Phe Tyr Val Leu Pro Leu Arg Gly Lys Leu Ser Phe Trp
                85                  90                  95

Glu Ala Ser Thr Thr Lys Ala Gly Tyr Pro Tyr Asn Tyr Asn Thr Thr
            100                 105                 110

Ala Ser Asp Gln Ile Leu Ile Glu Asn Ala Ala Gly His Arg Val Ala
        115                 120                 125

Ile Ser Thr Tyr Thr Thr Ser Leu Gly Ala Gly Pro Thr Ser Ile Ser
    130                 135                 140

Ala Val Gly Val Leu Ala Pro His Ser Ala Leu Ala Ala Leu Glu Asp
145                 150                 155                 160

Thr Val Asp Tyr Pro Cys Asp Cys Arg Gly Asp Cys Phe Cys
                165                 170

<210> SEQ ID NO 17
<211> LENGTH: 318
<212> TYPE: PRT
<213> ORGANISM: Artificial Sequence
<220> FEATURE:
<223> OTHER INFORMATION: Norovirus P domain (NoV P) of VA387

<400> SEQUENCE: 17

Ser Arg Thr Lys Pro Phe Thr Val Pro Ile Leu Thr Val Glu Glu Met
1               5                   10                  15

Ser Asn Ser Arg Phe Pro Ile Pro Leu Glu Lys Leu Tyr Thr Gly Pro
            20                  25                  30

Ser Ser Ala Phe Val Gln Pro Gln Asn Gly Arg Cys Thr Thr Asp
            35                  40                  45

Gly Val Leu Leu Gly Thr Thr Gln Leu Ser Ala Val Asn Ile Cys Thr
     50                  55                  60

Phe Arg Gly Asp Val Thr His Ile Ala Gly Ser His Asp Tyr Ile Met
 65                  70                  75                  80

Asn Leu Ala Ser Gln Asn Trp Asn Asn Tyr Asp Pro Thr Glu Glu Ile
                85                  90                  95

Pro Ala Pro Leu Gly Thr Pro Asp Phe Val Gly Lys Ile Gln Gly Met
            100                 105                 110

Leu Thr Gln Thr Thr Arg Glu Asp Gly Ser Thr Arg Ala His Lys Ala
        115                 120                 125

Thr Val Ser Thr Gly Ser Val His Phe Thr Pro Lys Leu Gly Ser Val
    130                 135                 140

Gln Tyr Thr Thr Asp Thr Asn Asn Asp Leu Gln Thr Gly Gln Asn Thr
145                 150                 155                 160

Lys Phe Thr Pro Val Gly Val Ile Gln Asp Gly Asn Asn His Gln Asn
                165                 170                 175

Glu Pro Gln Gln Trp Val Leu Pro Asn Tyr Ser Gly Arg Thr Gly His
            180                 185                 190

Asn Val His Leu Ala Pro Ala Val Ala Pro Thr Phe Pro Gly Glu Gln
        195                 200                 205

Leu Leu Phe Phe Arg Ser Thr Met Pro Gly Cys Ser Gly Tyr Pro Asn
    210                 215                 220

Met Asn Leu Asp Cys Leu Leu Pro Gln Glu Trp Val Gln His Phe Tyr
225                 230                 235                 240

Gln Glu Ala Ala Pro Ala Gln Ser Asp Val Ala Leu Leu Arg Phe Val
                245                 250                 255

Asn Pro Asp Thr Gly Arg Val Leu Phe Glu Cys Lys Leu His Lys Ser
            260                 265                 270

Gly Tyr Val Thr Val Ala His Thr Gly Pro His Asp Leu Val Ile Pro
        275                 280                 285

Pro Asn Gly Tyr Phe Arg Phe Asp Ser Trp Val Asn Gln Phe Tyr Thr
    290                 295                 300

Leu Ala Pro Met Gly Asn Gly Ala Gly Arg Arg Arg Ala Leu
305                 310                 315

<210> SEQ ID NO 18
<211> LENGTH: 327
<212> TYPE: PRT
<213> ORGANISM: Artificial Sequence
<220> FEATURE:
<223> OTHER INFORMATION: NoV P+ (VA387)

<400> SEQUENCE: 18

Ser Arg Thr Lys Pro Phe Thr Val Pro Ile Leu Thr Val Glu Glu Met
 1               5                  10                  15

Ser Asn Ser Arg Phe Pro Ile Pro Leu Glu Lys Leu Tyr Thr Gly Pro
            20                  25                  30

Ser Ser Ala Phe Val Val Gln Pro Gln Asn Gly Arg Cys Thr Thr Asp
        35                  40                  45

Gly Val Leu Leu Gly Thr Thr Gln Leu Ser Ala Val Asn Ile Cys Thr
    50                  55                  60

Phe Arg Gly Asp Val Thr His Ile Ala Gly Ser His Asp Tyr Ile Met
65                  70                  75                  80

Asn Leu Ala Ser Gln Asn Trp Asn Asn Tyr Asp Pro Thr Glu Glu Ile
                85                  90                  95

Pro Ala Pro Leu Gly Thr Pro Asp Phe Val Gly Lys Ile Gln Gly Met
            100                 105                 110

Leu Thr Gln Thr Thr Arg Glu Asp Gly Ser Thr Arg Ala His Lys Ala
        115                 120                 125

Thr Val Ser Thr Gly Ser Val His Phe Thr Pro Lys Leu Gly Ser Val
130                 135                 140

Gln Tyr Thr Thr Asp Thr Asn Asn Asp Leu Gln Thr Gly Gln Asn Thr
145                 150                 155                 160

Lys Phe Thr Pro Val Gly Val Ile Gln Asp Gly Asn Asn His Gln Asn
                165                 170                 175

Glu Pro Gln Gln Trp Val Leu Pro Asn Tyr Ser Gly Arg Thr Gly His
            180                 185                 190

Asn Val His Leu Ala Pro Ala Val Ala Pro Thr Phe Pro Gly Glu Gln
        195                 200                 205

Leu Leu Phe Phe Arg Ser Thr Met Pro Gly Cys Ser Gly Tyr Pro Asn
210                 215                 220

Met Asn Leu Asp Cys Leu Leu Pro Gln Glu Trp Val Gln His Phe Tyr
225                 230                 235                 240

Gln Glu Ala Ala Pro Ala Gln Ser Asp Val Ala Leu Leu Arg Phe Val
                245                 250                 255

Asn Pro Asp Thr Gly Arg Val Leu Phe Glu Cys Lys Leu His Lys Ser
            260                 265                 270

Gly Tyr Val Thr Val Ala His Thr Gly Pro His Asp Leu Val Ile Pro
        275                 280                 285

Pro Asn Gly Tyr Phe Arg Phe Asp Ser Trp Val Asn Gln Phe Tyr Thr
290                 295                 300

Leu Ala Pro Met Gly Asn Gly Ala Gly Arg Arg Arg Ala Leu Cys Asp
305                 310                 315                 320

Cys Arg Gly Asp Cys Phe Cys
                325

<210> SEQ ID NO 19
<211> LENGTH: 314
<212> TYPE: PRT
<213> ORGANISM: Artificial Sequence
<220> FEATURE:
<223> OTHER INFORMATION: NoV P- (VA387)

<400> SEQUENCE: 19

Ser Arg Thr Lys Pro Phe Thr Val Pro Ile Leu Thr Val Glu Glu Met
1               5                   10                  15

Ser Asn Ser Arg Phe Pro Ile Pro Leu Glu Lys Leu Tyr Thr Gly Pro
            20                  25                  30

Ser Ser Ala Phe Val Val Gln Pro Gln Asn Gly Arg Cys Thr Thr Asp
        35                  40                  45

Gly Val Leu Leu Gly Thr Thr Gln Leu Ser Ala Val Asn Ile Cys Thr
50                  55                  60

Phe Arg Gly Asp Val Thr His Ile Ala Gly Ser His Asp Tyr Ile Met
65                  70                  75                  80

Asn Leu Ala Ser Gln Asn Trp Asn Asn Tyr Asp Pro Thr Glu Glu Ile
                85                  90                  95

Pro Ala Pro Leu Gly Thr Pro Asp Phe Val Gly Lys Ile Gln Gly Met
            100                 105                 110

-continued

```
Leu Thr Gln Thr Thr Arg Glu Asp Gly Ser Thr Arg Ala His Lys Ala
            115                 120                 125

Thr Val Ser Thr Gly Ser Val His Phe Thr Pro Lys Leu Gly Ser Val
130                 135                 140

Gln Tyr Thr Thr Asp Thr Asn Asn Asp Leu Gln Thr Gly Gln Asn Thr
145                 150                 155                 160

Lys Phe Thr Pro Val Gly Val Ile Gln Asp Gly Asn Asn His Gln Asn
                165                 170                 175

Glu Pro Gln Gln Trp Val Leu Pro Asn Tyr Ser Gly Arg Thr Gly His
            180                 185                 190

Asn Val His Leu Ala Pro Ala Val Ala Pro Thr Phe Pro Gly Glu Gln
        195                 200                 205

Leu Leu Phe Phe Arg Ser Thr Met Pro Gly Cys Ser Gly Tyr Pro Asn
    210                 215                 220

Met Asn Leu Asp Cys Leu Leu Pro Gln Glu Trp Val Gln His Phe Tyr
225                 230                 235                 240

Gln Glu Ala Ala Pro Ala Gln Ser Asp Val Ala Leu Leu Arg Phe Val
                245                 250                 255

Asn Pro Asp Thr Gly Arg Val Leu Phe Glu Cys Lys Leu His Lys Ser
            260                 265                 270

Gly Tyr Val Thr Val Ala His Thr Gly Pro His Asp Leu Val Ile Pro
        275                 280                 285

Pro Asn Gly Tyr Phe Arg Phe Asp Ser Trp Val Asn Gln Phe Tyr Thr
    290                 295                 300

Leu Ala Pro Met Gly Asn Gly Ala Gly Arg
305                 310

<210> SEQ ID NO 20
<211> LENGTH: 224
<212> TYPE: PRT
<213> ORGANISM: Artificial Sequence
<220> FEATURE:
<223> OTHER INFORMATION: GST from Schistosoma Japonicum

<400> SEQUENCE: 20

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160
```

```
Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

<210> SEQ ID NO 21
<211> LENGTH: 159
<212> TYPE: PRT
<213> ORGANISM: Artificial Sequence
<220> FEATURE:
<223> OTHER INFORMATION: VP8* (rotavirus)

<400> SEQUENCE: 21

Leu Asp Gly Pro Tyr Gln Pro Thr Thr Phe Thr Pro Pro Thr Asp Tyr
1               5                   10                  15

Trp Ile Leu Ile Asn Ser Asn Thr Asn Gly Val Val Tyr Glu Ser Thr
            20                  25                  30

Asn Asn Ser Asp Phe Trp Thr Ala Val Ile Ala Val Glu Pro His Val
        35                  40                  45

Asn Pro Val Asp Arg Gln Tyr Asn Val Phe Gly Glu Asn Lys Gln Phe
    50                  55                  60

Asn Val Arg Asn Asp Ser Asp Lys Trp Lys Phe Leu Glu Met Phe Arg
65                  70                  75                  80

Gly Ser Ser Gln Asn Asp Phe Tyr Asn Arg Arg Thr Leu Thr Ser Asp
                85                  90                  95

Thr Arg Leu Val Gly Ile Leu Lys Tyr Gly Gly Arg Ile Trp Thr Phe
            100                 105                 110

His Gly Glu Thr Pro Arg Ala Thr Thr Asp Ser Ser Asn Thr Ala Asn
        115                 120                 125

Leu Asn Gly Ile Ser Ile Thr Ile His Ser Glu Phe Tyr Ile Ile Pro
    130                 135                 140

Arg Ser Gln Glu Ser Lys Cys Asn Glu Tyr Ile Asn Asn Gly Leu
145                 150                 155

<210> SEQ ID NO 22
<211> LENGTH: 15
<212> TYPE: PRT
<213> ORGANISM: Artificial Sequence
<220> FEATURE:
<223> OTHER INFORMATION: T cell epitope of NoV P of VA387:

<400> SEQUENCE: 22

His Phe Tyr Gln Glu Ala Ala Pro Ala Gln Ser Asp Val Ala Leu
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: T Cell epitope of NoV P of VA207

<400> SEQUENCE: 23

Ala Thr Ala Arg Ser Glu Val Ala Leu Leu Arg Phe Val Asn Pro
1               5                   10                  15
```

<210> SEQ ID NO 24
<211> LENGTH: 15
<212> TYPE: PRT
<213> ORGANISM: Artificial Sequence
<220> FEATURE:
<223> OTHER INFORMATION: T Cell epitope of NoV P of VA115

<400> SEQUENCE: 24

Thr Leu Thr Glu Ala Ala Gln Leu Ala Pro Pro Ile Tyr Pro Pro
1               5                   10                  15

<210> SEQ ID NO 25
<211> LENGTH: 312
<212> TYPE: PRT
<213> ORGANISM: Artificial Sequence
<220> FEATURE:
<223> OTHER INFORMATION: NoV P- (VA207)

<400> SEQUENCE: 25

Ser Lys Thr Lys Ala Phe Thr Ile Pro Val Leu Lys Ile Ser Glu Met
1               5                   10                  15

Thr Asn Ser Arg Phe Pro Val Pro Val Asp Gln Met Tyr Thr Ser Arg
                20                  25                  30

Ser Glu Gly Ile Val Val Gln Pro Gln Asn Gly Arg Ala Thr Ile Asp
            35                  40                  45

Gly Glu Leu Leu Gly Thr Thr Leu Val Ser Pro Val Ser Val Cys Asn
    50                  55                  60

Phe Lys Gly Asn Leu Gln Ala Glu Val Pro Gly Gln His Gln Leu Tyr
65                  70                  75                  80

Gln Leu Gln Leu Thr Asn Leu Asp Gly Ser Pro Ile Asp Pro Thr Asp
                85                  90                  95

Asp Thr Pro Gly Pro Leu Gly Cys Pro Asp Phe Thr Gly Leu Leu Tyr
            100                 105                 110

Gly Val Ala Ser Gln Arg Gly Pro Gly Asp Ala Thr Arg Ala His Glu
    115                 120                 125

Ala Arg Ile Asp Thr Gly Ser Asp Thr Phe Ala Pro Lys Ile Gly Gln
130                 135                 140

Val Arg Phe Tyr Ser Thr Ser Ser Asp Phe Glu Thr Asn Gln Pro Thr
145                 150                 155                 160

His Phe Thr Pro Ile Gly Ile Tyr Ile Glu Gly Asn Ser Ser Asp Phe
                165                 170                 175

Asn Gln Trp Gln Leu Pro Arg Tyr Gly Gly His Leu Ala Asn Asn Asn
            180                 185                 190

His Leu Ala Pro Ala Val Ser Pro Leu Phe Pro Gly Glu Gln Ile Leu
    195                 200                 205

Phe Phe Arg Ser Phe Ile Pro Gly Ala Ser Gly His Thr Asn Gly Glu
    210                 215                 220

Met Asp Cys Leu Leu Pro Gln Glu Phe Val Gln His Phe Tyr Gln Glu
225                 230                 235                 240

Ala Ala Thr Ala Arg Ser Glu Val Ala Leu Leu Arg Phe Val Asn Pro
                245                 250                 255

Asp Thr Gly Arg Ala Leu Phe Glu Ser Lys Leu His Lys Gln Gly Phe
            260                 265                 270

Met Thr Ile Ala Ser Ser Gly Asp His Pro Ile Ile Met Pro Thr Asn
    275                 280                 285

Gly Tyr Phe Arg Phe Glu Ala Trp Val Asn Gln Phe Tyr Ser Leu Ala
    290                 295                 300

Pro Val Gly Thr Gly Ser Gly Arg
305                 310

<210> SEQ ID NO 26
<211> LENGTH: 316
<212> TYPE: PRT
<213> ORGANISM: Artificial Sequence
<220> FEATURE:
<223> OTHER INFORMATION: NoV P- (VA115)

<400> SEQUENCE: 26

Gln Lys Thr Lys Pro Phe Ser Val Pro Asn Leu Pro Leu Asn Thr Leu
1               5                   10                  15

Ser Asn Ser Arg Val Pro Ser Leu Ile Arg Ser Met Met Val Ser Arg
            20                  25                  30

Asp His Gly Gln Met Val Gln Phe Gln Asn Gly Arg Val Thr Leu Asp
        35                  40                  45

Gly Gln Leu Gln Gly Thr Thr Pro Thr Ser Ala Ser Gln Leu Cys Lys
    50                  55                  60

Ile Arg Gly Ser Val Phe His Ala Asn Gly Asn Gly Tyr Thr Leu
65                  70                  75                  80

Thr Glu Leu Asp Gly Ser Pro Tyr His Ala Phe Glu Ser Pro Ala Pro
                85                  90                  95

Ile Gly Phe Pro Asp Leu Gly Glu Cys Asp Trp His Met Glu Ala Ser
            100                 105                 110

Pro Thr Thr Gln Phe Asp Thr Gly Asp Val Ile Lys Gln Ile Asn Val
        115                 120                 125

Lys Gln Glu Ala Ala Phe Ala Pro His Leu Gly Thr Ile Gln Ala Asp
    130                 135                 140

Gly Leu Ser Asp Val Ser Val Asn Thr Asn Met Ile Ala Lys Leu Gly
145                 150                 155                 160

Trp Val Ser Pro Ala Ser Asp Gly His Arg Gly Asn Val Asp Pro Trp
                165                 170                 175

Val Ile Pro Arg Tyr Gly Ser Thr Leu Thr Glu Ala Ala Gln Leu Ala
            180                 185                 190

Pro Pro Ile Tyr Pro Pro Gly Phe Gly Glu Ala Ile Val Phe Phe Met
        195                 200                 205

Ser Asp Phe Pro Ile Ala His Gly Ala Asn Gly Leu Ser Val Pro Cys
    210                 215                 220

Thr Ile Pro Gln Glu Phe Val Thr His Phe Val Asn Glu Gln Ala Pro
225                 230                 235                 240

Thr Arg Gly Glu Ala Ala Leu Leu His Tyr Leu Asp Pro Asp Thr His
                245                 250                 255

Arg Asn Leu Gly Glu Phe Lys Leu Tyr Pro Glu Gly Phe Met Thr Cys
            260                 265                 270

Val Pro Asn Ser Ser Gly Thr Gly Pro Gln Thr Leu Pro Ile Asn Gly
        275                 280                 285

Val Phe Val Phe Val Ser Trp Val Ser Arg Phe Tyr Gln Leu Lys Pro
    290                 295                 300

Val Gly Thr Ala Gly Pro Ala Arg Ser Leu Gly Ile
305                 310                 315

<210> SEQ ID NO 27
<211> LENGTH: 31
<212> TYPE: DNA
<213> ORGANISM: Artificial Sequence

```
<220> FEATURE:
<223> OTHER INFORMATION: Primer P524

<400> SEQUENCE: 27
gcacggatcc tcaagaacta aaccattcac c                              31

<210> SEQ ID NO 28
<211> LENGTH: 36
<212> TYPE: DNA
<213> ORGANISM: Artificial Sequence
<220> FEATURE:
<223> OTHER INFORMATION: Primer P561

<400> SEQUENCE: 28
gcgtgcggcc gcttaccccg ctccatttcc catggg                         36

<210> SEQ ID NO 29
<211> LENGTH: 63
<212> TYPE: DNA
<213> ORGANISM: Artificial Sequence
<220> FEATURE:
<223> OTHER INFORMATION: Primer P590

<400> SEQUENCE: 29
gcatgcggcc gcttagcaaa agcaatcgcc acggcaatcg cataatgcac gtctgcgccc    60
cgc                                                                  63

<210> SEQ ID NO 30
<211> LENGTH: 30
<212> TYPE: DNA
<213> ORGANISM: Artificial Sequence
<220> FEATURE:
<223> OTHER INFORMATION: Primer P821

<400> SEQUENCE: 30
gcacggatcc tcaaagacta aggcattcac                                30

<210> SEQ ID NO 31
<211> LENGTH: 36
<212> TYPE: DNA
<213> ORGANISM: Artificial Sequence
<220> FEATURE:
<223> OTHER INFORMATION: Primer P834

<400> SEQUENCE: 31
agtcgcggcc gcttagcgcc cacttccagt tcccac                         36

<210> SEQ ID NO 32
<211> LENGTH: 30
<212> TYPE: DNA
<213> ORGANISM: Artificial Sequence
<220> FEATURE:
<223> OTHER INFORMATION: Primer P843

<400> SEQUENCE: 32
gcacggatcc caaaagacta aaccatttag                                30

<210> SEQ ID NO 33
<211> LENGTH: 35
<212> TYPE: DNA
<213> ORGANISM: Artificial Sequence
<220> FEATURE:
<223> OTHER INFORMATION: Primer P846

<400> SEQUENCE: 33
```
gcatgcggcc gcttaacgag ccgggccggc tgttc          35

<210> SEQ ID NO 34
<211> LENGTH: 30
<212> TYPE: DNA
<213> ORGANISM: Artificial Sequence
<220> FEATURE:
<223> OTHER INFORMATION: Primer P1572

<400> SEQUENCE: 34
atatcgtctc ccccgctcc atttcccatg                30

<210> SEQ ID NO 35
<211> LENGTH: 29
<212> TYPE: DNA
<213> ORGANISM: Artificial Sequence
<220> FEATURE:
<223> OTHER INFORMATION: Primer P1573

<400> SEQUENCE: 35
tattcgtctc cggggtgag caagggcga                 29

<210> SEQ ID NO 36
<211> LENGTH: 31
<212> TYPE: DNA
<213> ORGANISM: Artificial Sequence
<220> FEATURE:
<223> OTHER INFORMATION: Primer P1574

<400> SEQUENCE: 36
gcatgcggcc gcttacttgt acagctcgtc c              31

<210> SEQ ID NO 37
<211> LENGTH: 46
<212> TYPE: DNA
<213> ORGANISM: Artificial Sequence
<220> FEATURE:
<223> OTHER INFORMATION: Primer P1617

<400> SEQUENCE: 37
atatcgtctc ccctccgcct ccgcctccgc ccccgctcc atttcc     46

<210> SEQ ID NO 38
<211> LENGTH: 45
<212> TYPE: DNA
<213> ORGANISM: Artificial Sequence
<220> FEATURE:
<223> OTHER INFORMATION: Primer P1618

<400> SEQUENCE: 38
tattcgtctc cgaggcggag gcggaggcgg atcaagaact aaacc      45

<210> SEQ ID NO 39
<211> LENGTH: 48
<212> TYPE: DNA
<213> ORGANISM: Artificial Sequence
<220> FEATURE:
<223> OTHER INFORMATION: Primer P1656

<400> SEQUENCE: 39
tattcgtctc cggggatcga gggaaggatt tcaatgtcac cgatacta   48

<210> SEQ ID NO 40
<211> LENGTH: 37
<212> TYPE: DNA
<213> ORGANISM: Artificial Sequence
<220> FEATURE:
<223> OTHER INFORMATION: Primer P1657

<400> SEQUENCE: 40
gcatgcggcc gcttaatccg attttggagg atggtcg                    37

<210> SEQ ID NO 41
<211> LENGTH: 50
<212> TYPE: DNA
<213> ORGANISM: Artificial Sequence
<220> FEATURE:
<223> OTHER INFORMATION: Primer P1689

<400> SEQUENCE: 41
atacgcggat cctgcaacgg ccgttgctca agaactaaac cattcaccgt     50

<210> SEQ ID NO 42
<211> LENGTH: 32
<212> TYPE: DNA
<213> ORGANISM: Artificial Sequence
<220> FEATURE:
<223> OTHER INFORMATION: Primer P1734

<400> SEQUENCE: 42
atatcgtctc ctaatgcacg tctgcgcccc gc                        32

<210> SEQ ID NO 43
<211> LENGTH: 35
<212> TYPE: DNA
<213> ORGANISM: Artificial Sequence
<220> FEATURE:
<223> OTHER INFORMATION: Primer P1735

<400> SEQUENCE: 43
tattcgtctc cattattaga tggtccttat caacc                     35

<210> SEQ ID NO 44
<211> LENGTH: 36
<212> TYPE: DNA
<213> ORGANISM: Artificial Sequence
<220> FEATURE:
<223> OTHER INFORMATION: Primer P1736

<400> SEQUENCE: 44
gcatgcggcc gcttatagac cgttgttaat atattc                    36

<210> SEQ ID NO 45
<211> LENGTH: 51
<212> TYPE: DNA
<213> ORGANISM: Artificial Sequence
<220> FEATURE:
<223> OTHER INFORMATION: Primer P1955

<400> SEQUENCE: 45
tattcgtctc cgaggcggag gcggaggcgg acaaaagact aaaccattta g   51

<210> SEQ ID NO 46
<211> LENGTH: 51
<212> TYPE: DNA
<213> ORGANISM: Artificial Sequence
<220> FEATURE:
<223> OTHER INFORMATION: Primer P1957

<400> SEQUENCE: 46
tattcgtctc cgaggcggag gcggaggcgg atcaaagact aaggcattca c   51

```
<210> SEQ ID NO 47
<211> LENGTH: 35
<212> TYPE: DNA
<213> ORGANISM: Artificial Sequence
<220> FEATURE:
<223> OTHER INFORMATION: Primer P1958

<400> SEQUENCE: 47
gcatgcggcc gcttacccac ttccagttcc cacag                          35

<210> SEQ ID NO 48
<211> LENGTH: 37
<212> TYPE: DNA
<213> ORGANISM: Artificial Sequence
<220> FEATURE:
<223> OTHER INFORMATION: Primer P1985

<400> SEQUENCE: 48
atattattgc acggatcccc gaccccgtct ccggctc                        37

<210> SEQ ID NO 49
<211> LENGTH: 60
<212> TYPE: DNA
<213> ORGANISM: Artificial Sequence
<220> FEATURE:
<223> OTHER INFORMATION: Primer P1986

<400> SEQUENCE: 49
gcatgcggcc gcttagcaaa agcaatcgcc acggcaatcg cacgggtagt caacggtgtc    60

<210> SEQ ID NO 50
<211> LENGTH: 6
<212> TYPE: PRT
<213> ORGANISM: Artificial Sequence
<220> FEATURE:
<223> OTHER INFORMATION: 6 residue linker

<400> SEQUENCE: 50

Leu Val Pro Arg Gly Ser
1               5

<210> SEQ ID NO 51
<211> LENGTH: 12
<212> TYPE: PRT
<213> ORGANISM: Artificial Sequence
<220> FEATURE:
<223> OTHER INFORMATION: 12 glycine linker

<400> SEQUENCE: 51

Gly Gly Gly Gly Gly Gly Gly Gly Gly Gly Gly Gly
1               5                   10

<210> SEQ ID NO 52
<211> LENGTH: 6
<212> TYPE: PRT
<213> ORGANISM: Artificial Sequence
<220> FEATURE:
<223> OTHER INFORMATION: 6 glycine linker

<400> SEQUENCE: 52

Gly Gly Gly Gly Gly Gly
1               5

<210> SEQ ID NO 53
<211> LENGTH: 8
<212> TYPE: PRT
```

```
<213> ORGANISM: Artificial Sequence
<220> FEATURE:
<223> OTHER INFORMATION: 8 residue NoV hinge of NoV VP1

<400> SEQUENCE: 53

Phe Leu Val Pro Pro Thr Val Glu
1               5

<210> SEQ ID NO 54
<211> LENGTH: 208
<212> TYPE: PRT
<213> ORGANISM: Artificial Sequence
<220> FEATURE:
<223> OTHER INFORMATION: AstV P

<400> SEQUENCE: 54
```

Ser Ile Tyr Leu Pro Leu Pro Gln Ala Asp Asp Gln Tyr Thr Pro Tyr
1               5                   10                  15

Phe Val Tyr Asn Phe Gln Gly Glu Arg Val Ser Thr Thr Glu Thr Gly
                20                  25                  30

Val Phe Cys Leu Ala Ala Ile Pro Ala Ala Thr Thr Ser Ser Arg Tyr
            35                  40                  45

Asn Asn Gln Ile Thr Thr Pro Ser Ile Gly Tyr Arg Asn Ala Ser Gly
    50                  55                  60

Thr Gly Thr Ser Phe Leu Leu Asp Ala Ala Ser Trp Trp Asn Ile Leu
65                  70                  75                  80

Asp Val Thr Gln Thr Gly Val Leu Phe Gly Gln Pro Arg Leu Gly Val
                85                  90                  95

Gly Val Met Gln Thr Met Lys Thr Leu Lys Gln His Ile Lys Asp Tyr
            100                 105                 110

Thr Glu Pro Ala Ile Gln Lys Tyr Tyr Pro Gly Thr Thr Asn Leu Asp
        115                 120                 125

Glu Gln Leu Lys Gln Arg Leu Asn Leu Ala Glu Gly Asp Pro Val Ile
    130                 135                 140

Ser Met Gly Asp Thr Asn Gly Arg Arg Ala Ala Leu Phe Tyr Arg Thr
145                 150                 155                 160

Ser Asp Glu Lys Tyr Ile Leu Phe Phe Ser Thr Thr Glu Asp Pro Gly
                165                 170                 175

Ala Gln Tyr Gln Asn Leu Lys Met Leu Tyr Phe Trp Asn Trp Ser Tyr
            180                 185                 190

Ser Asp Thr Lys Gln Gln Phe Leu Asp His Leu Arg Thr Val Gln Phe
        195                 200                 205

```
<210> SEQ ID NO 55
<211> LENGTH: 720
<212> TYPE: PRT
<213> ORGANISM: Artificial Sequence
<220> FEATURE:
<223> OTHER INFORMATION: NoV P- -HEV P -AstV P

<400> SEQUENCE: 55
```

Ser Arg Thr Lys Pro Phe Thr Val Pro Ile Leu Thr Val Glu Glu Met
1               5                   10                  15

Ser Asn Ser Arg Phe Pro Ile Pro Leu Glu Lys Leu Tyr Thr Gly Pro
                20                  25                  30

Ser Ser Ala Phe Val Val Gln Pro Gln Asn Gly Arg Cys Thr Thr Asp
            35                  40                  45

Gly Val Leu Leu Gly Thr Thr Gln Leu Ser Ala Val Asn Ile Cys Thr
        50                  55                  60

```
Phe Arg Gly Asp Val Thr His Ile Ala Gly Ser His Asp Tyr Ile Met
 65                  70                  75                  80

Asn Leu Ala Ser Gln Asn Trp Asn Asn Tyr Asp Pro Thr Glu Glu Ile
             85                  90                  95

Pro Ala Pro Leu Gly Thr Pro Asp Phe Val Gly Lys Ile Gln Gly Met
        100                 105                 110

Leu Thr Gln Thr Thr Arg Glu Asp Gly Ser Thr Arg Ala His Lys Ala
        115                 120                 125

Thr Val Ser Thr Gly Ser Val His Phe Thr Pro Lys Leu Gly Ser Val
130                 135                 140

Gln Tyr Thr Thr Asp Thr Asn Asn Asp Leu Gln Thr Gly Gln Asn Thr
145                 150                 155                 160

Lys Phe Thr Pro Val Gly Val Ile Gln Asp Gly Asn Asn His Gln Asn
                165                 170                 175

Glu Pro Gln Gln Trp Val Leu Pro Asn Tyr Ser Gly Arg Thr Gly His
            180                 185                 190

Asn Val His Leu Ala Pro Ala Val Ala Pro Thr Phe Pro Gly Glu Gln
        195                 200                 205

Leu Leu Phe Phe Arg Ser Thr Met Pro Gly Cys Ser Gly Tyr Pro Asn
210                 215                 220

Met Asn Leu Asp Cys Leu Leu Pro Gln Glu Trp Val Gln His Phe Tyr
225                 230                 235                 240

Gln Glu Ala Ala Pro Ala Gln Ser Asp Val Ala Leu Leu Arg Phe Val
                245                 250                 255

Asn Pro Asp Thr Gly Arg Val Leu Phe Glu Cys Lys Leu His Lys Ser
            260                 265                 270

Gly Tyr Val Thr Val Ala His Thr Gly Pro His Asp Leu Val Ile Pro
        275                 280                 285

Pro Asn Gly Tyr Phe Arg Phe Asp Ser Trp Val Asn Gln Phe Tyr Thr
290                 295                 300

Leu Ala Pro Met Gly Asn Gly Ala Gly Arg Gly Gly Gly Gly Gly Gly
305                 310                 315                 320

Gly Gly Gly Gly Gly Thr Pro Ser Pro Ala Pro Ser Arg Pro Phe
                325                 330                 335

Ser Val Leu Arg Ala Asn Asp Val Leu Trp Leu Ser Leu Thr Ala Ala
            340                 345                 350

Glu Tyr Asp Gln Thr Thr Tyr Gly Ser Ser Thr Asn Pro Met Tyr Val
        355                 360                 365

Ser Asp Thr Val Thr Phe Val Asn Val Ala Thr Gly Ala Gln Ala Val
370                 375                 380

Ala Arg Ser Leu Asp Trp Ser Lys Val Thr Leu Asp Gly Arg Pro Leu
385                 390                 395                 400

Thr Thr Ile Gln Gln Tyr Ser Lys Thr Phe Tyr Val Leu Pro Leu Arg
                405                 410                 415

Gly Lys Leu Ser Phe Trp Glu Ala Ser Thr Thr Lys Ala Gly Tyr Pro
            420                 425                 430

Tyr Asn Tyr Asn Thr Thr Ala Ser Asp Gln Ile Leu Ile Glu Asn Ala
        435                 440                 445

Ala Gly His Arg Val Ala Ile Ser Thr Tyr Thr Thr Ser Leu Gly Ala
        450                 455                 460

Gly Pro Thr Ser Ile Ser Ala Val Gly Val Leu Ala Pro His Ser Ala
465                 470                 475                 480
```

```
Leu Ala Ala Leu Glu Asp Thr Val Asp Tyr Pro Cys Asp Cys Arg Gly
                485                 490                 495

Asp Cys Phe Cys Gly Gly Gly Gly Gly Gly Gly Gly Gly Gly
            500                 505                 510

Ser Ile Tyr Leu Pro Leu Pro Gln Ala Asp Asp Gln Tyr Thr Pro Tyr
                515                 520                 525

Phe Val Tyr Asn Phe Gln Gly Glu Arg Val Ser Thr Glu Thr Gly
                530                 535                 540

Val Phe Cys Leu Ala Ala Ile Pro Ala Ala Thr Ser Ser Arg Tyr
545                 550                 555                 560

Asn Asn Gln Ile Thr Thr Pro Ser Ile Gly Tyr Arg Asn Ala Ser Gly
                565                 570                 575

Thr Gly Thr Ser Phe Leu Leu Asp Ala Ala Ser Trp Trp Asn Ile Leu
                580                 585                 590

Asp Val Thr Gln Thr Gly Val Leu Phe Gly Gln Pro Arg Leu Gly Val
                595                 600                 605

Gly Val Met Gln Thr Met Lys Thr Leu Lys Gln His Ile Lys Asp Tyr
                610                 615                 620

Thr Glu Pro Ala Ile Gln Lys Tyr Tyr Pro Gly Thr Thr Asn Leu Asp
625                 630                 635                 640

Glu Gln Leu Lys Gln Arg Leu Asn Leu Ala Glu Gly Asp Pro Val Ile
                645                 650                 655

Ser Met Gly Asp Thr Asn Gly Arg Arg Ala Ala Leu Phe Tyr Arg Thr
                660                 665                 670

Ser Asp Glu Lys Tyr Ile Leu Phe Phe Ser Thr Thr Glu Asp Pro Gly
                675                 680                 685

Ala Gln Tyr Gln Asn Leu Lys Met Leu Tyr Phe Trp Asn Trp Ser Tyr
                690                 695                 700

Ser Asp Thr Lys Gln Gln Phe Leu Asp His Leu Arg Thr Val Gln Phe
705                 710                 715                 720

<210> SEQ ID NO 56
<211> LENGTH: 565
<212> TYPE: PRT
<213> ORGANISM: Artificial Sequence
<220> FEATURE:
<223> OTHER INFORMATION: AstV P -HEV P -VP8*

<400> SEQUENCE: 56

Ser Ile Tyr Leu Pro Leu Pro Gln Ala Asp Asp Gln Tyr Thr Pro Tyr
1               5                   10                  15

Phe Val Tyr Asn Phe Gln Gly Glu Arg Val Ser Thr Glu Thr Gly
                20                  25                  30

Val Phe Cys Leu Ala Ala Ile Pro Ala Ala Thr Thr Ser Ser Arg Tyr
                35                  40                  45

Asn Asn Gln Ile Thr Thr Pro Ser Ile Gly Tyr Arg Asn Ala Ser Gly
                50                  55                  60

Thr Gly Thr Ser Phe Leu Leu Asp Ala Ala Ser Trp Trp Asn Ile Leu
65                  70                  75                  80

Asp Val Thr Gln Thr Gly Val Leu Phe Gly Gln Pro Arg Leu Gly Val
                85                  90                  95

Gly Val Met Gln Thr Met Lys Thr Leu Lys Gln His Ile Lys Asp Tyr
                100                 105                 110

Thr Glu Pro Ala Ile Gln Lys Tyr Tyr Pro Gly Thr Thr Asn Leu Asp
                115                 120                 125
```

```
Glu Gln Leu Lys Gln Arg Leu Asn Leu Ala Glu Gly Asp Pro Val Ile
            130                 135                 140

Ser Met Gly Asp Thr Asn Gly Arg Arg Ala Ala Leu Phe Tyr Arg Thr
145                 150                 155                 160

Ser Asp Glu Lys Tyr Ile Leu Phe Phe Ser Thr Thr Glu Asp Pro Gly
                165                 170                 175

Ala Gln Tyr Gln Asn Leu Lys Met Leu Tyr Phe Trp Asn Trp Ser Tyr
            180                 185                 190

Ser Asp Thr Lys Gln Gln Phe Leu Asp His Leu Arg Thr Val Gln Phe
                195                 200                 205

Gly Gly Gly Gly Gly Gly Gly Gly Gly Gly Thr Pro Ser Pro
210                 215                 220

Ala Pro Ser Arg Pro Phe Ser Val Leu Arg Ala Asn Asp Val Leu Trp
225                 230                 235                 240

Leu Ser Leu Thr Ala Ala Glu Tyr Asp Gln Thr Thr Tyr Gly Ser Ser
                245                 250                 255

Thr Asn Pro Met Tyr Val Ser Asp Thr Val Thr Phe Val Asn Val Ala
                260                 265                 270

Thr Gly Ala Gln Ala Val Ala Arg Ser Leu Asp Trp Ser Lys Val Thr
            275                 280                 285

Leu Asp Gly Arg Pro Leu Thr Thr Ile Gln Gln Tyr Ser Lys Thr Phe
290                 295                 300

Tyr Val Leu Pro Leu Arg Gly Lys Leu Ser Phe Trp Glu Ala Ser Thr
305                 310                 315                 320

Thr Lys Ala Gly Tyr Pro Tyr Asn Tyr Asn Thr Thr Ala Ser Asp Gln
                325                 330                 335

Ile Leu Ile Glu Asn Ala Ala Gly His Arg Val Ala Ile Ser Thr Tyr
            340                 345                 350

Thr Thr Ser Leu Gly Ala Gly Pro Thr Ser Ile Ser Ala Val Gly Val
                355                 360                 365

Leu Ala Pro His Ser Ala Leu Ala Ala Leu Glu Asp Thr Val Asp Tyr
370                 375                 380

Pro Cys Asp Cys Arg Gly Asp Cys Phe Cys Gly Gly Gly Gly Gly Gly
385                 390                 395                 400

Gly Gly Gly Gly Gly Gly Leu Asp Gly Pro Tyr Gln Pro Thr Thr Phe
                405                 410                 415

Thr Pro Pro Thr Asp Tyr Trp Ile Leu Ile Asn Ser Asn Thr Asn Gly
                420                 425                 430

Val Val Tyr Glu Ser Thr Asn Asn Ser Asp Phe Trp Thr Ala Val Ile
            435                 440                 445

Ala Val Glu Pro His Val Asn Pro Val Asp Arg Gln Tyr Asn Val Phe
450                 455                 460

Gly Glu Asn Lys Gln Phe Asn Val Arg Asn Asp Ser Asp Lys Trp Lys
465                 470                 475                 480

Phe Leu Glu Met Phe Arg Gly Ser Ser Gln Asn Asp Phe Tyr Asn Arg
                485                 490                 495

Arg Thr Leu Thr Ser Asp Thr Arg Leu Val Gly Ile Leu Lys Tyr Gly
            500                 505                 510

Gly Arg Ile Trp Thr Phe His Gly Glu Thr Pro Arg Ala Thr Thr Asp
                515                 520                 525

Ser Ser Asn Thr Ala Asn Leu Asn Gly Ile Ser Ile Thr Ile His Ser
530                 535                 540
```

-continued

```
Glu Phe Tyr Ile Ile Pro Arg Ser Gln Glu Ser Lys Cys Asn Glu Tyr
545                 550                 555                 560

Ile Asn Asn Gly Leu
                565

<210> SEQ ID NO 57
<211> LENGTH: 23
<212> TYPE: PRT
<213> ORGANISM: Artificial Sequence
<220> FEATURE:
<223> OTHER INFORMATION: M2e epitope

<400> SEQUENCE: 57

Ser Leu Leu Thr Glu Val Glu Thr Pro Ile Arg Asn Glu Trp Gly Cys
1               5                   10                  15

Arg Cys Asn Asp Ser Ser Asp
                20
```

PROTEIN COMPLEX SYSTEM FOR INCREASED IMMUNOGENICITY AND FUNCTIONALITY, AND METHODS MAKING AND USE

CROSS REFERENCE TO RELATED APPLICATIONS

This application claims the benefit of U.S. Provisional application 61/670,288, filed Jul. 7, 2012, the disclosure of which is incorporated by reference in its entirety.

INTEREST/GOVERNMENT SUPPORT

This invention was made with government support under AI092434, AI089634, AI055649 and RR026314 awarded by the National Institutes of Health. The government has certain rights in the invention.

FIELD OF THE INVENTION

The present invention relates in general to vaccines, antiviral drugs, drug delivery systems, and vaccine development, and in particular to methods of preparing very large protein complexes for use as a multivalent vaccine for infections caused by Norovirus, as well as virus types other than Norovirus.

BACKGROUND OF THE INVENTION

Norovirus (NoV), also known previously as "Norwalk-Like Virus" (NLV) or small round structured virus, is the most important viral pathogen of epidemic acute gastroenteritis that occurs in both developed and developing countries. These genetically diverse viruses comprise two major genogroups (GI and GII) and approximately 30 genotypes. NoVs belong to the genus Norovirus in the Caliciviridae family and are non-enveloped, icosahedral, single stranded, positive-sense RNA viruses whose outer protein capsids are composed of 180 copies of a single major structural protein, the VP1 protein.

The NoV genome is ~7.6 kb in length, and is composed of three open reading frames (ORFs), of which the latter two encode the major (VP1) and minor (VP2) structural proteins of NoV capsid, respectively. When expressed in vitro in eukaryotic cells, the NoV capsid protein self-assembles into virus-like particle (VLPs) that are structurally and antigenically indistinguishable from native NoV virions. The crystal structure of NoV capsid reveals a T=3 icosahedral symmetry, formed by 180 VP1s that organize into 90 dimers (17). Each VP1 can be divided into two major domains, the shell (S) and the protruding (P) domains that constitute the icosahedral shell and protruding arches of the capsid, respectively. The protruding arch, formed by a P dimer, represents the surface antigenic structure of NoV and is responsible for virus-host interactions and immune responses of NoVs. NoV VLPs serve as a useful tool for NoV research, owing to the lack of an effective cell culture and a small animal model for human NoVs. The S and P domains appear to be structurally and functionally independent. Expression of the S domain alone forms S particles with a smooth surface without binding function to histo-blood group antigens (HBGAs), the viral receptors or ligands of human NoVs. On the other hand, expression of the P domain (with or without end-modifications) can form three types of P domain complexes, each having binding function to HBGAs. They are the P dimer, and two larger oligomers of the P dimer: the 12-mer small P particle, and the 24-mer P particle. We have also recently identified 18-mer and 36-mer P complexes, demonstrating the interchangeable nature and dynamic relationship of all P domain complexes. Since the P dimer and the P particle can be easily produced in Escherichia coli (E. coli) and retain HBGA-binding function, they have been used as models for the study of NoV-HBGA interaction extensively. U.S. Pat. No. 8,277,819, the disclosure of which is incorporated by reference in its entirety, describes Norovirus capsid protein monomers having only the P domain that can assemble spontaneously into a P-particle having an icosahedral form. These stable P-particles are useful in methods for diagnosing and treating Norovirus-infected individuals, and in methods for making vaccines and for the treatment, amelioration and prevention of Norovirus infections.

Previously it has been demonstrated that the P particle can be applied as a vaccine platform for foreign antigen presentation. Each P domain has three surface loops on the distal end, corresponding to the outermost surface of the P particle. Previous studies demonstrated that these loops are excellent sites in presenting a foreign antigen for increased immune responses. U.S. Pat. Publication 2010-0322962, which is incorporated herein by reference in its entirety, discloses that a distal portion of the NoV P-domain monomer includes a peptide string into which a peptide unit of a foreign antigen, and in particular a foreign viral antigen, can be inserted. The resulting antigen-P-domain monomers can spontaneously assemble into a nanoparticle called an antigen-P-particle, typically of an octahedral form, that consists of 24 of the antigen-P-domain monomers arranged into 12 dimers. This P-particle is easily produced in E. coli, extremely stable, and highly immunogenic. We studied this particle using a His-tag as a model and obtained excellent results.

Bioengineering has become an important field that advances many technologies of modern medicine. Development of recombinant viral subunit vaccines for control and prevention of infectious diseases is a typical example. Unlike traditional vaccines, which are either live attenuated or inactivated viruses, the subunit vaccines are recombinant viral proteins. Therefore, the subunit vaccines do not have risk of infection while inducing protective antiviral immune responses and thus represent a new, safer generation of vaccines. Successful examples of such recombinant vaccines include the four commercially available virus-like particle (VLP) vaccines: Recombivax HB (Merck) and Energix-B (GlaxoSmithKline, GSK) against hepatitis B virus (HBV) and Gardasil (Merck) and Cervarix (GSK) against human papilloma virus (HPV). Additionally, numerous other subviral vaccines, including the Norovirus (NoV) VLP and P particle vaccines are under intensive development. Hence, recombinant subunit vaccine technology represents an innovative vaccine strategy complementary to conventional vaccine approaches.

An important factor for a recombinant viral antigen to become an effective vaccine is its immunogenicity. Most icosahedral VLPs are highly immunogenic because of their large sizes and polyvalent antigenic structures. However, many other monomeric, dimeric and oligomeric viral antigens possess a low immunogenicity due to their smaller sizes and low valences. Traditionally, these small antigens need to be presented by a large, multivalent vaccine platform for improved immunogenicity to become candidate vaccines. For example, rotavirus VP8* antigen (159 residues), the outermost portion of the spike protein VP4, has been conjugated to the surface loop of the 24-meric NoV P particle for increased immunogenicity and protective immunity. However, although a number of small viral or bacterial antigens have been successfully presented by different multivalent platforms, limitations clearly exist depending on the structural compatibility between the antigens and the platforms, which prevent a wider application of the current vaccine platforms.

Notwithstanding the advancements in the therapeutic treatment of and vaccine development against viral and bacterial infection, including NoV infections, there remains a need for improving and/or enhancing the immunogenicity of vaccines in general, and in particular providing a vaccine against NoV that has increased immunogenicity. It would also be beneficial to provide a large, multivalent immunogenic composition that can significantly increase the functionality of a functional group, such as a drug effective group, and/or enhance the immunogenicity of an antigen or epitope. There also remains a need to provide therapeutic treatment in the form of a multivalent vaccine for infections caused by NoV, as well as virus types other than NoV.

SUMMARY OF THE INVENTION

The present invention relates to a method for forming recombinant proteins that naturally form dimers and/or oligomers, into large, even enormous, polyvalent complexes. The complexes can be used for improving the immunogenicity and functionality of the proteins and its constituents. Three types of complexes, namely "linear", "network" and "agglomerate" complexes, each with potentially enormous molecular sizes and polyvalences, are provided. These complexes can be easily produced, and demonstrate enhanced immunogenicity and functionality compared with those of the recombinant protein dimers or monomers. Herein are disclosed models and protocols for the design, construction and manipulation of these complexes, and for the creation and use of such complexes for enhancing the immunogenicity and functionality of its constituent proteins and antigens.

An aspect of the invention provides a multivalent immunogenic composition in the form of a large complex comprising a plurality of any of the dimeric/oligomeric fusion proteins described herein, and a method for using the large complex. The large complex typically assembles spontaneously through intermolecular interactions among the homologous protein domains; for example, through homotypic intermolecular dimerization or oligomerization of the protein domains. In one embodiment, the composition can induce an immune response capable of treating, ameliorating, reducing and preventing the clinical symptoms associated with infection caused by a pathogen.

Another aspect of the invention is a protein structure comprising a plurality of recombinant dimeric fusion proteins, the recombinant dimeric fusion protein comprising at least two dimeric protein domains, wherein the protein structure is formed by intermolecular interactions among the dimeric protein domains of the plurality of dimeric fusion proteins. The at least two dimeric protein domains can be different or the same, and can be different or the same species. Typically at least one of the at least two dimeric protein domains is a P domain of a virus selected from the group consisting of Norovirus (NoV), Hepatitis E virus (HEV), Astrovirus (AstV), rotavirus, and influenza virus. Other dimeric proteins domains can include non-viral protein domains, including glutathione S-transferase (GST). The recombinant dimeric fusion protein typically includes a linker protein between the dimeric protein domains. A dimeric protein domain includes an oligomeric protein domain.

The recombinant dimeric fusion protein, and the protein structure made therewith, can also include a dimeric protein domain that includes a foreign antigen, including a foreign viral antigen.

The protein structure can be a linear protein complex, an agglomerate protein complex, or a network protein complex, or some combination thereof.

Another aspect of the invention is a method of forming a protein structure, comprising the steps of: a) forming a dimeric fusion gene that codes for a recombinant dimeric fusion protein by joining a first dimeric gene that codes for a first dimeric protein domain, to a second dimeric gene that codes for a second dimeric protein domain; b) expressing a plurality of the recombinant dimeric fusion proteins comprising the first dimeric protein domain and the second dimeric protein domain; and c) associating the plurality of recombinant dimeric fusion proteins under conditions that intermolecular homotypic interactions among the respective first and second dimeric protein domains of the plurality of dimeric fusion proteins forms a protein structure.

The method can employ dimeric protein domains that can include a P domain of a virus selected from the group consisting of Norovirus (NoV), Hepatitis E virus (HEV), Astrovirus (AstV), rotavirus, and influenza virus. The step of forming a dimeric fusion gene can include joining a linker sequence between the first dimeric protein domain and the second dimeric protein domain.

Another aspect of the invention is a method of providing immune protection to a mammal against a viral pathogen, comprising the step of administering to the mammal as a vaccine an immunogenic composition comprising any protein structure made according to the invention or described herein. The method can include dimeric protein domains that are different, and that a P domain of a virus that is selected from the group consisting of Norovirus (NoV), Hepatitis E virus (HEV), Astrovirus (AstV), rotavirus, and influenza virus.

Another aspect of the invention provides a multivalent vaccine for infections caused by NoV comprising a multivalent immunogenic composition in the form of a large complex comprising a plurality of dimeric fusion proteins, and methods for making and using the large complex. Typically at least one of the protein domains of each dimeric fusion protein is a NoV P protein domain.

Another aspect of the invention provides a method for improving and/or enhancing the immunogenicity of a vaccine against a pathogen, comprising the step of providing a large complex comprising dimeric fusion proteins for use as a platform in creating the vaccine.

Another aspect of the invention is a recombinant dimeric fusion protein comprising a first dimeric protein domain, a second dimeric protein domain, and a linker peptide between the first and second dimeric protein domain. In one embodiment, the second dimeric protein domain is different from the first dimeric protein domain.

Another aspect of the invention is a recombinant dimeric fusion protein comprising at least three dimeric protein domains, each of the at least three dimeric protein portions being the same or different from the other two of the three dimeric protein domains, and a linker peptide connecting the at least three dimeric protein domains.

Another aspect of the invention is a recombinant dimeric-oligomeric fusion protein comprising a first dimeric protein domain, a second oligomeric protein domain, and a linker peptide between the first dimeric protein domain and the second oligomeric protein domain, and a method for making the dimeric-oligomeric fusion protein.

Another aspect of the invention is a large complex comprising a plurality of recombinant dimeric fusion proteins comprising at least one dimeric protein domain and a plurality of monomeric caps comprising a monomer of the dimeric protein domain that is dimerized to the at least one dimeric protein domain of the dimeric fusion protein.

While the nature and advantages of the present invention will be more fully appreciated from the following drawings and detailed description, showing the contemplated novel construction, combinations and elements as herein described, and more particularly defined by the appended claims, it is understood that changes in the precise embodiments of the present invention are meant to be included within the scope of the claims, except insofar as they may be precluded by the prior art.

BRIEF DESCRIPTION OF THE DRAWINGS

FIG. 15-1: Panels A and B show NoV P domain-specific antibody responses post-immunization; Panels C and D show NoV P domain-specific CD4+ T cell responses post immunization.

FIG. 15-2: Panels E, F and G show blocking rates of the linear/network complex-induced antisera, which blocked binding of NoVs to histo-blood group antigens (HBGAs).

DETAILED DESCRIPTION OF THE INVENTION

Definitions

Figure 1:
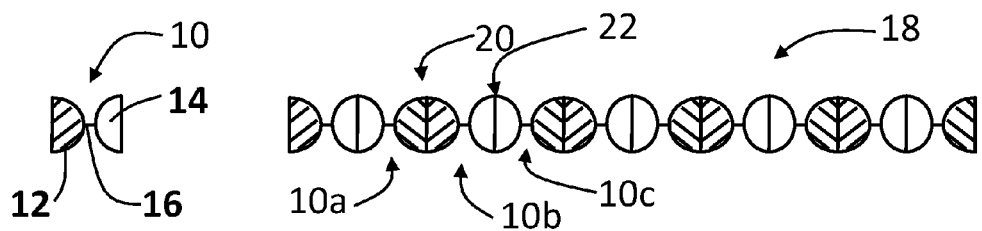
FIG. 1 illustrates a di-heterotypic dimeric fusion protein comprising two heterotypic protein portions, and a long linear complex formed through homotypic intermolecular dimerizations of the protein domains of the dimeric fusion proteins.

As used herein, the term "antigen" may be used interchangeably with the terms "immunogen" and "immunogenic antigen", as defined below. Technically speaking, an antigen is a substance that is able to combine with the products of an immune response once they are made, but is not necessarily able to induce an immune response (i.e. while all immunogens are antigens, the reverse is not true); however, the antigens that are discussed herein as the subject of the present invention are assumed to be immunogenic antigens, even when referred to as antigens.

The term "dimer" means a macromolecular complex formed by two, typically non-covalently bound macromolecules (with the exception of disulfide bridges), such as two proteins. Dimers typically form spontaneously via intermolecular interactions between regions of their protein structure. A dimer can be a quaternary structure of a protein. Further, a "homo-dimer" can be formed by two identical macromolecules (via a process called homodimerization), and a "hetero-dimer" can be formed by two different macromolecules (via a process called heterodimerization). Some proteins contain specialized domains to ensure dimerization (dimerization domains).

The term "dimeric protein" means a protein capable of dimerization.

The term "oligomeric protein" means a protein capable of oligomerization.

The term "oligomer" means a macromolecular complex usually formed by 4 to 25, typically non-covalently bound macromolecules (with the exception of disulfide bridges), such as proteins. Oligomers typically form spontaneously via intermolecular interactions among regions of their protein monomers. An oligomer can be a quaternary structure of a protein. Further, a "homo-oligomer" can be formed by identical macromolecules (via a process called homooligomerization), and a "hetero-oligomer" can be formed by different macromolecules (via a process called heterooligomerization). Some proteins contain specialized domains to ensure oligomerization (oligomerization domains).

The term "dimeric fusion protein" means a recombinant protein that functions as both a dimeric protein and a fusion protein (as defined herein); a single polypeptide with functional properties derived from the original proteins; a dimeric fusion protein can be made through recombinant DNA technology, either homotypically (i.e. with two identical dimeric proteins) or heterotypically (i.e. with two different dimeric proteins).

The terms "domain" and "protein domain" mean a part of a protein sequence and structure that can evolve, function, and exist independently of the rest of the protein chain. Each domain forms a compact three-dimensional structure and often can be independently stable and folded.

The term "fusion gene" means a gene created by the joining recombinantly of two or more genes which originally coded for separate proteins.

The term "fusion protein" means a protein created through translation of a fusion gene, resulting in a single polypeptide with functional properties derived from each of the original proteins.

The term "immunity" means the state of having sufficient biological defenses to avoid infection, disease, or other biological invasion by a disease-causing organism.

The term "immunogenicity" means the ability of an immunogen to elicit a humoral and/or cell-mediated immune response.

The terms "immunogen" and "immunogenic antigen" mean a specific type of antigen that is able to induce or provoke an adaptive immune response in the form of the production of one or more antibodies.

The terms "immunogenic response" and "immune response" mean an alteration in the reactivity of an organisms' immune system in response to an immunogen. This can involve antibody production, induction of cell-mediated immunity, complement activation or development of acquired immunity or immunological tolerance to a certain disease or pathogen.

The terms "immunization" and "vaccination" mean the deliberate induction of an immune response, and involve effective manipulation of the immune system's natural specificity, as well as its inducibility. The principle behind immunization is to introduce an antigen, derived from a disease-causing organism, which stimulates the immune system to develop protective immunity against that organism, but wherein the antigen itself does not cause the pathogenic effects of that organism.

The term "infection" means the invasion of an animal or plant host's body tissues by a pathogen, as well as the multiplication of the pathogen within the body and the body's reaction to the pathogen and any toxins that it may produce.

The terms "Norovirus," "NoV", "Norwalk-like virus," or "NLV" refer to any virus of the Norovirus genus in the Calicivirus family, and includes, without limitation, the following: Norwalk Virus ("NV"), MOH, Mexico, VA 207, VA 387, 02-1419, C59, VA 115, Hawaii, Snow Mountain, Hillington, Toronto, Leeds, Amsterdam, Idaho Falls, Lordsdale, Grimsby, Southampton, Desert Shield, Birmingham, and White Rivercap. NoVs cause acute gastroenteritis in humans.

The term "vaccine" means a biological preparation or composition that improves immunity to a particular disease. Vaccines are examples of immunogenic antigens intentionally administered to induce an immune response in the recipient.

The terms "monovalent vaccine" and "univalent vaccine" mean a vaccine designed to immunize against a single antigen or single microorganism.

The terms "multivalent vaccine" and "polyvalent vaccine" mean a vaccine designed to immunize against two or more strains of the same microorganism (such as NoV), or against two or more different microorganisms.

The term "pathogen" means an infectious agent which causes disease in its animal or plant host; for example, a pathogen can be a microorganism, such as a virus or bacterium.

Detailed Description of the Invention

The present invention provides a effective approach to turn small dimeric/oligomeric proteins into enormous polyvalent protein complexes, for significantly improved immunogenicity and functionality. This was achieved by creating fusion proteins from translation of fusion genes (i.e. genes created by the joining of two or more genes which originally coded for separate proteins), resulting in a single polypeptide with functional properties derived from each of the original dimeric/oligomeric protein domains. Each fusion protein typically includes two or more such protein domains in a single molecule, either homotypically or heterotypically, through recombinant DNA technology. Because each individual polypeptide or protein domain in the fusion protein can behave naturally and independently of the other domains(s) in the fusion protein, intermolecular interactions native to each domain are free to form a dimer or an oligomer with a respective protein domain in another fusion protein, such that the complexes assemble spontaneously. The dimer or oligomer fusion proteins can be produced in $E.$ $coli.$ The principles of the proposed variable complex system are elucidated in FIGS. 1-5. Homotypic interactions of the dimeric/oligomeric protein components of each fusion protein results in the formation of large linear or network complexes.

FIG. 1 shows a dimeric fusion protein 10 comprising a first dimeric protein domain 12, a second dimeric protein domain 14, and a polypeptide linker 16 fusing the first dimeric protein domain 12 and the second dimeric protein domain 14. The dimeric fusion protein can be homotypic, with the first and second protein domains being the same, or heterotypic, with the first and second protein domains being different. Thus, the dimeric fusion protein 10 can include a first dimeric domain 12, a second dimeric main 14 that is the same or different from the first dimeric domain 12, and a linker 16 between the first dimeric domain 12 and the second dimeric domain 14. The successive intermolecular dimerization of the heterotypic dimeric domains 12, 14 of a plurality of dimeric fusion proteins 10 can form a long linear complex 18, illustrated by homotypic dimer unit 20 of two first dimeric domains 12 of adjacent first and second dimeric fusion proteins 10a and 10b, and the homotypic dimer units 22 of two second dimeric domains 14 of adjacent second and third dimeric fusion proteins 10b and 10c. A dimeric protein that predominantly forms a dimer can also form trimers or other multi-mers in low portions. In such cases, the linear complex can include branching.

The linker 16 is typically a polypeptide of at least one, and more typically two or more amino acid units, and more typically 4 or more amino acid units, and even more typically 8 or more amino acid units, which is fused between both the first and second dimeric protein domains. Linker or spacer peptides are added between the protein domains of the original dimeric protein, which fuse the two dimeric protein domains together, and allow the protein domains to fold independently and function natively to form dimers, bind, and present epitope sites for antibody recognition. A longer linker is used as necessary to ensure that two adjacent dimeric protein domains do not sterically interfere with one another. The amino acid (aa) length of the linker should be sufficient to allow flexibility of the protein domains in the molecule to dimerize, but not so long, and not so flexible, that the dimeric fusion protein can self-dimerize; that is, where two molecules 10 having protein domains 12 and 14 separated by linker 16 can orient to allow the respective first protein domains 12 to dimerize and the respective second protein domains 14 to dimerize. Linkers can be engineered with cleavage sites (of 3-8 amino acids, or more) for digestion (cleavage) by proteases or chemical agents which enable the breakage of the linker and liberation of the two dimeric protein domains. This technique is often used for identification and purification of proteins, by fusing a GST protein or a hexa-his peptide (6×His-tag) which can be isolated using affinity chromatography. However, a few, some, most or all of the linkers can comprise a cleavage site or a plurality of cleavage sites, disposed within linkers inserted into and within the network. After formation of the complex, cleavage or digestion of such cleavage sites can result in separations within the linear or network complex. Linkers can be fused to either end (N-terminus or C-terminus) of the protein domain, or to a portion of the domain that does not interfere with the protein's formation of dimers, or binding to epitopes.

The linker between the fused proteins can also be a factor for a better yield, functionality, and stability of the fusion proteins. An example of a linker is a 6-amino acid residue linker (LVPRGS, SEQ. ID. NO:50) that pre-existed in GST-gene fusion system (GE Healthcare Life Sciences) which was used between GST and a protein of interest, which works well with dimeric protein domains of the present invention. In producing the GST-NoV $P^{-}$-NoV V complexes, a 12-glycine linker (SEQ. ID. NO:51) between the two NoV P-s works well, and better than, a linker of either 6-glycine (SEQ. ID. NO:52) or an 8-residue NoV hinge (FLVPPTVE, SEQ. ID. NO:53) of NoV VP1. A string of glycines can serve this purpose.

FIG. 2 shows a heterotypic dimeric fusion protein 30 comprising a first dimeric domain 32, a second dimeric domain 34, and a third dimeric domain, wherein at least one of the second dimeric domain 34 or the third dimeric domain 36 is different from the first dimeric domain 32, and linkers 37 and 38. The first linker 37 links the first dimeric domain 32 and the second dimeric domain 34, and the second linker 38 links the second dimeric domain 34 and the third dimeric domain 36. The successive homotypic intermolecular dimerization of the heterotypic dimeric protein portions 32, 34 and 36 of a plurality of dimeric fusion proteins 30 can form a large, networking complex 40, formed by the dimerization units 42 of the two first dimeric domains 32, the dimerization units 44 of the two second dimeric domain 34, and the dimerization units 46 of the two third dimeric domains 36, of adjacent dimeric fusion proteins 30. The three dimeric protein domains of a dimeric fusion protein 30 independently dimerize homotypically with protein domains of other dimeric fusion proteins 30. Consequently, a first dimeric fusion protein molecule 30 binds via dimerization to at least one, and typically two or three, other dimeric fusion proteins 30. These interactions go on and on, resulting in a large network complex 40. As the network complex grows, homotypic protein domain ends can dimerize to form a closed loop. Reaction conditions, including fusion protein concentration, can affect the regularity and uniformity of the network pattern, and it is within the scope and teaching of the invention that networks for an unlimited number of shapes and configurations can be made. It is also within the scope and teaching of the invention that the dimeric fusion protein can include a fourth protein domain linked with a third linkage portion to the third protein domain.

Figure 2:
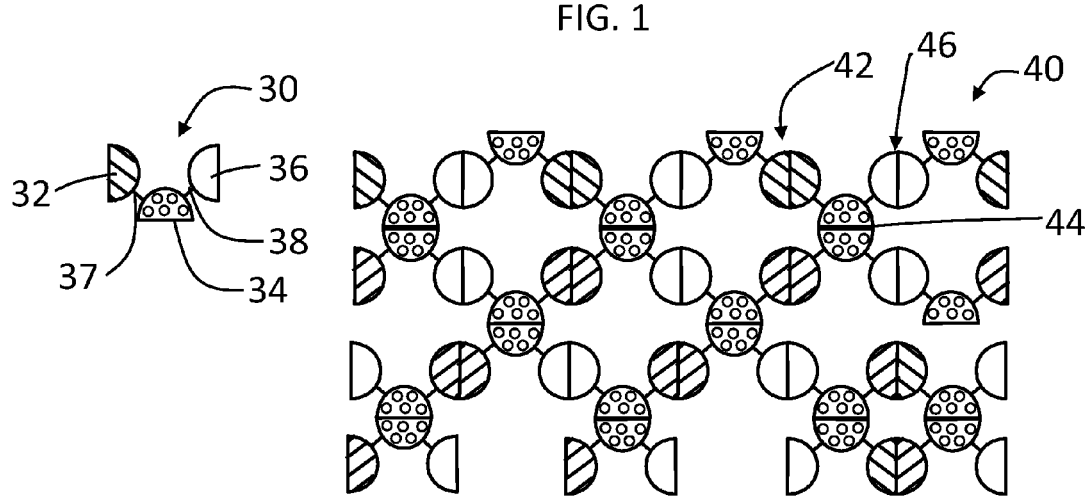
FIG. 2 illustrates a tri-heterotypic dimeric fusion protein comprising three heterotypic protein portions, and a network complex formed through homotypic intermolecular dimerizations of the protein domains of the dimeric fusion protein.
Figure 3:
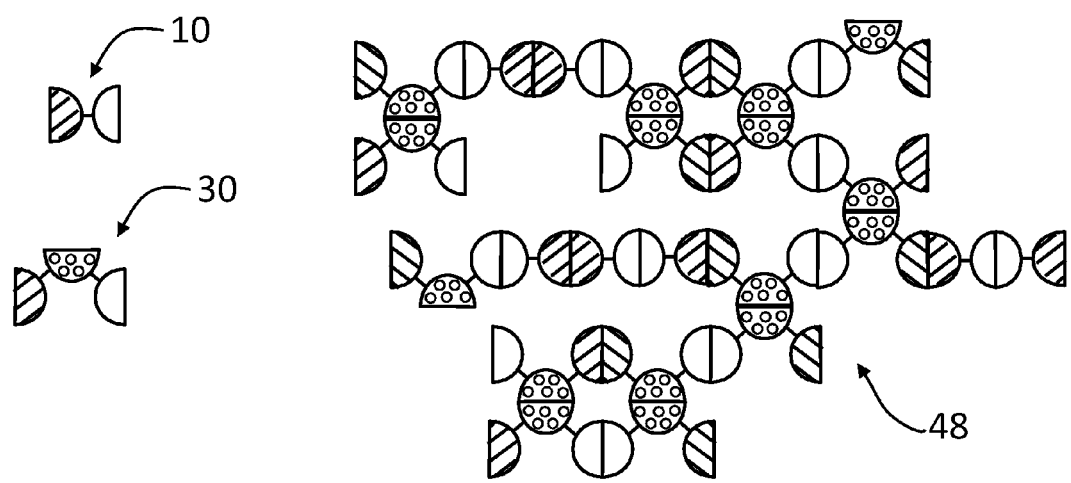
FIG. 3 illustrates a linear/network complex formed through homotypic intermolecular dimerizations of the protein domains of the di-heterotypic dimeric fusion proteins of FIG. 1 and the tri-heterotypic dimeric fusion proteins of FIG. 2.

A reaction composition of dimeric fusion protein molecules can comprise two distinct types of dimeric fusion proteins that include, as between them, at least one same dimeric protein domain. FIG. 3 shows a first heterotypic dimeric fusion protein 10, as shown in FIG. 1, and a second heterotypic dimeric fusion protein 30, as shown in FIG. 2, and a large, networking complex 48 formed by successive homotypic intermolecular dimerization, including: the dimerization of dimeric protein domains 12,32 between two first fusion proteins 10, or between two second proteins 30, or between a first protein 10 and a second protein 30; the dimerization of dimeric protein domains 14,36 between two first proteins 10, or between two second proteins 30, or between a first protein 10 and a second protein 30, and dimerization of the dimeric protein domains 14 and 36 between two first proteins 10 or two second proteins 30; and the dimerization of dimeric protein domains 34 between two second proteins 30. The arrangement and orientation of the dimeric fusion proteins 10 and 30 are influenced by a variety of conditions, including the relative concentration of the two types of dimeric fusion proteins 10 and 30, order and rate of addition, etc.

Figure 4:
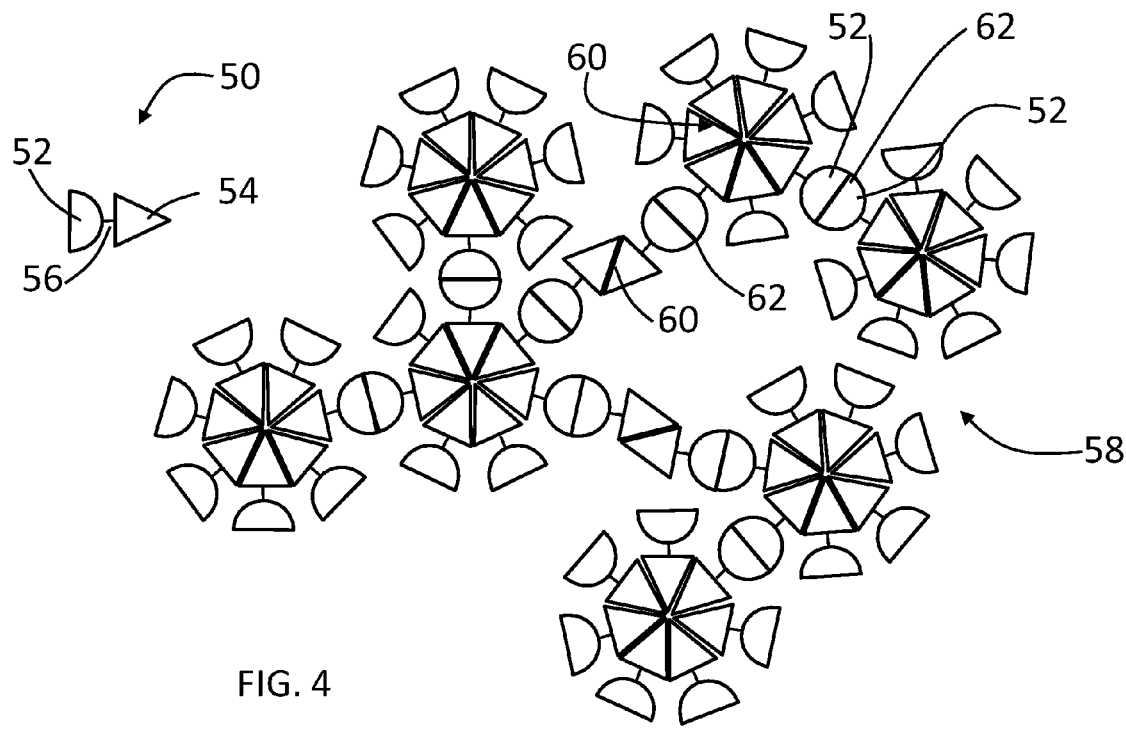
FIG. 4 illustrates a di-heterotypic dimeric fusion protein comprising a dimeric protein domain and an oligomeric protein domain, and an agglomerate complex formed through homotypic intermolecular oligomerization of the oligomeric protein domains and homotypic dimerization of the dimeric protein domains.

FIG. 4 shows a dimeric-oligomeric fusion protein 50 comprising a first dimeric protein domain 52, a second oligomeric protein domain 54, and a linker 56 that links the first dimeric protein domain 52 and the second oligomeric protein domain 54. Homotypic oligomerization of the oligomeric protein domains 54 result in agglomerated complex 58 that includes oligomerized units 60 consisting of a plurality of (typically, 3, 4, 5 or more) dimeric-oligomeric fusion proteins 50 oligomerized through the second oligomeric protein domains 54, and homotypic dimerization 62 of dimerized units 60 through the first dimeric domains 52.

It can be understood that any combination of the above dimeric fusion proteins and dimeric-oligomeric fusion proteins can be used, with the dimeric protein domain or oligomeric protein domain being any dimeric protein capable of dimerizing, or any oligomeric protein capable of forming an oligomeric complex, which resulting in a wide variety of different types of complexes dependent on the nature of the protein components of the dimeric fusion protein. Homotypic interactions of proteins forming dimeric and oligomeric complexes are commonly observed, particularly in viral structural proteins. Therefore, the proposed strategy for construction of enormous complexes can be applied to a wide range of proteins, including, but not limited to, viral protein.

Figure 5:
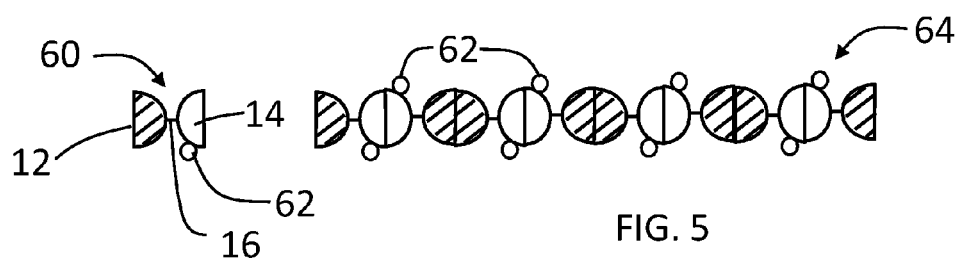
FIG. 5 illustrates a di-heterotypic dimeric fusion protein comprising a merged peptide or protein, and a resulting linear complex of the dimeric fusion proteins.
Figure 6:
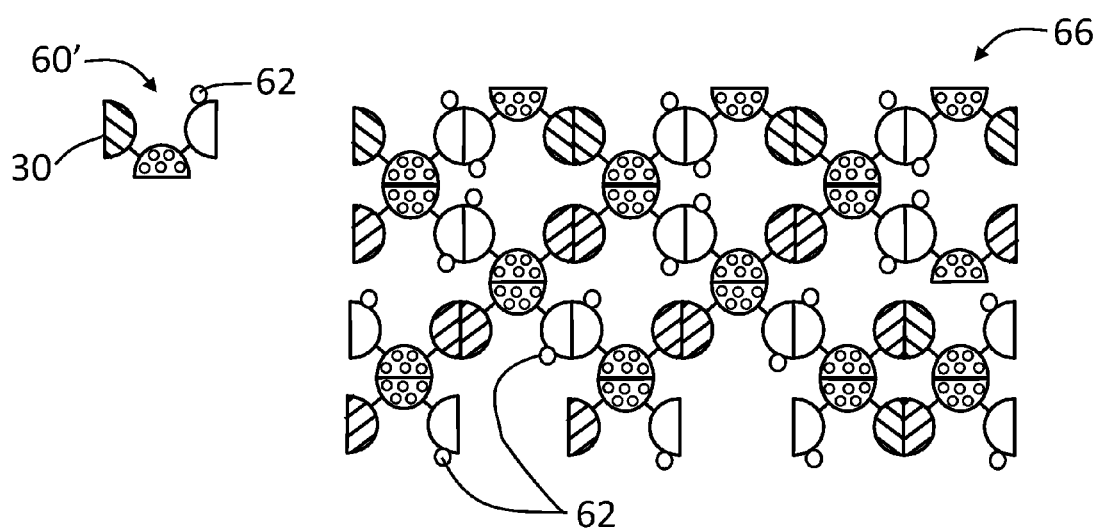
FIG. 6 illustrates a tri-heterotypic dimeric fusion protein comprising a merged peptide or protein, and a resulting network complex of the dimeric fusion proteins.

FIGS. 5 and 6 show a monomeric peptide or protein 62 that can be merged to a dimeric fusion protein 60 or 60'. The monomeric peptide or protein 62 can be merged by recombinant insertion in the sequence that encodes an exposed loop on a dimeric protein domain 12 or 14 of fusion protein 60, or dimeric protein domain 32, 34, or 36 of fusion protein 60', or by fusion to an end of one of the dimeric protein domains by insertion into the sequence that encodes the one of the dimeric domains. The long linear complex 64, the large, networking complex 66, and an agglomerated complex, similar to the structure shown in FIG. 4, of dimeric and/or oligomeric fusion proteins comprise one or more monomeric peptides or proteins 62, thus providing a polyvalent vaccine platform or drug-carrier. The monomeric peptides or proteins 62 can be the same or identical peptides or proteins, or different types. The variety of sizes and shapes of the resulting agglomerated complex are enormous and vast.

A distal portion of dimeric protein domain of a dimeric fusion protein can includes a peptide string, typically as a loop in an exposed surface of the dimeric protein domain, into which a peptide unit of a foreign antigen, including a foreign viral antigen, can be inserted recombinantly by inserting the sequence of the foreign antigen into the sequence that encodes the peptide string of the dimeric protein domain. The resulting dimeric fusion protein, and the protein structures formed therefrom, present the foreign antigen. Methods for engineering the foreign antigens into a dimeric fusion protein for use in the present invention to form dimeric fusion proteins, are described in U.S. Pat. Publication 2010-0322962, the disclosure of which is incorporated by reference in its entirety.

The protein domains can also be modified to add onto or delete portions off the N-terminus or the C-terminus of the protein, to add or modify the proteins function or properties. By way of example, native NoV P protein (SEQ. ID. NO:17) can be modified to delete four amino acids from the C-terminus end, resulting in modified P protein (designated NoV P$^-$, SEQ. ID. NO:19) that only forms dimers. Conversely, a nine-amino-acid cysteine-containing tag (RGDCFC) at the C-terminus end (designated NoV P$^+$, SEQ. ID. NO:18) forms 95% 24-mer.

Figure 7A:
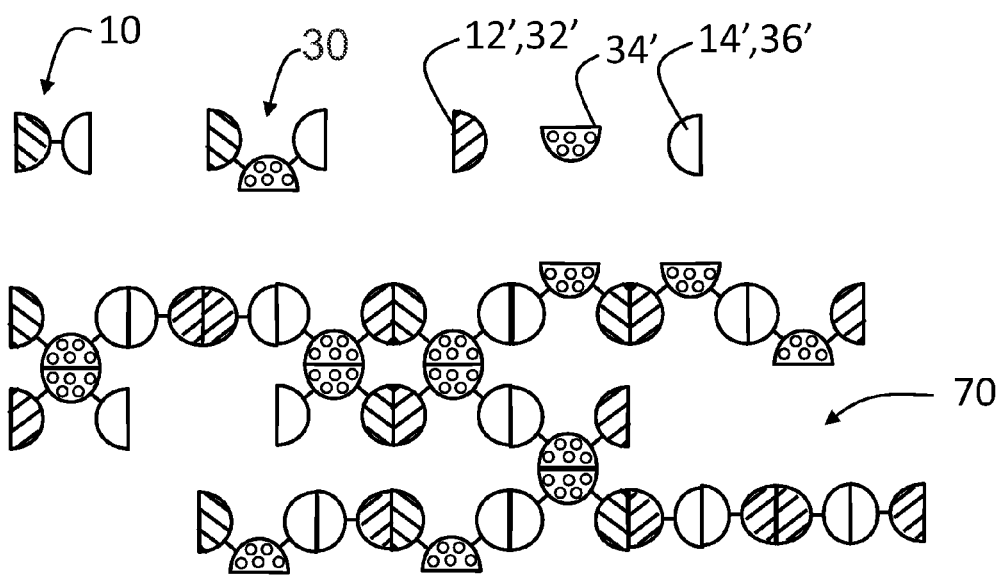
FIGS. 7A and 7B illustrate the capping of exposed dimeric protein domains of a linear/network complex of dimeric fusion proteins.
Figure 7B:
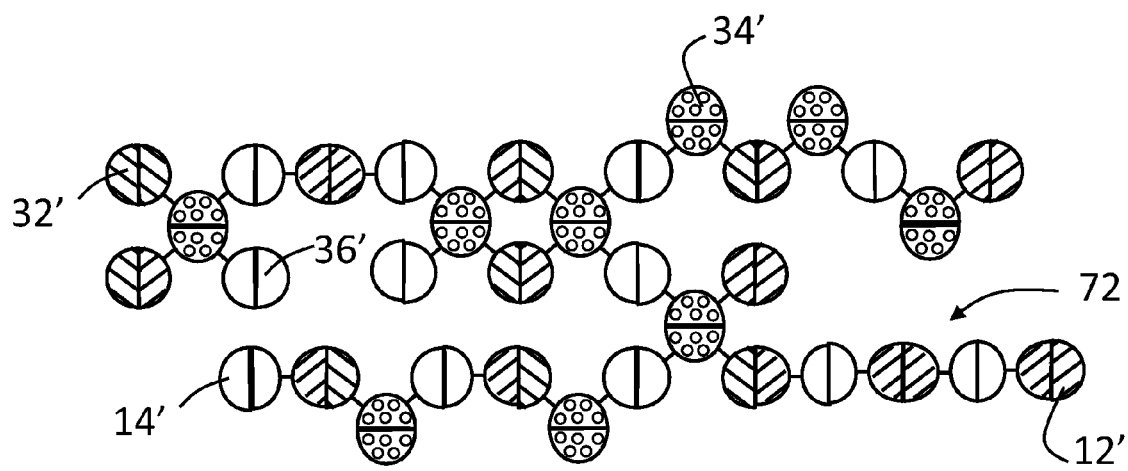

FIG. 7A shows a heterotypic large, network complex 70, similar to the complex 48 shown in FIG. 3, formed by the successive homotypic intermolecular dimerization of a first heterotypic dimeric fusion protein 10, and a second heterotypic dimeric fusion protein 30. FIG. 7A also shows dimer-forming monomer proteins, including a first protein 12'(or 32') that is the same protein as the first dimeric protein domain 12 of the dimeric fusion protein 10, or the first dimeric protein domain 32 of the dimeric fusion protein 30. Also shown are a second protein 14' (or 36') that is the same protein as the second dimeric protein domain 14 of the dimeric fusion protein 30, or the third dimeric protein domain 36 of the dimeric fusion protein 30; and a third protein 34', that is the same protein as the second dimeric protein domain 34 of the dimeric fusion protein 30. In accordance with an aspect of the present invention, the dimerization of dimer fusion proteins can be quenched, or terminated, by introducing a monomer of the dimer protein domain exposed on the dimer fusion protein, to form terminal dimer or "caps" at the exposed ends of the dimer fusion protein, as shown in FIG. 7B. It can be understood that the monomers of dimeric proteins 12' (or 32'), 14' (or 36') and 34', can be introduced individually, or in a combination of two, more or all. The amount of monomer of dimeric protein can be sufficient to cap only a portion of, any portion of, or all of, the exposed monomer ends of the dimer fusion proteins in the network. The monomers of dimeric proteins can be added simultaneously, or in any order or sequence. The capping of exposed ends by one type of monomer of dimeric protein can be followed by further dimerization by uncapped protein domains of dimer fusion proteins, which can in turn be followed by capping with another monomer of dimeric protein.

Polyvalence is also an important factor for the avidity outcome of a protein function. A typical example is the binding activity of different NoV P domain complexes (P dimer, 12mer small P particle and 24mer P particle) to their carbohydrate ligands are positively correlated with the valence of the complexes. Similar phenomena have been observed on histo-blood group antigens (HBGAs) in milk and saliva. The HBGAs that conjugate to the high molecular weight, polyvalent mucin-like backbones exhibit significantly higher interacting activity with NoV VLPs compared to the HBGAs conjugated to the smaller molecules. Thus, increasing the molecular size and multivalence can intensify the outcomes of a functional motif and help to improve the sensitivity of a functional assay.

Examples of dimeric proteins that can comprise the dimeric protein domain of the dimeric fusion protein, can include, but are not limited to, glutathione S-transferase (GST, SEQ. ID. NO:20), the protruding (P) domain of hepatitis E virus (HEV P, SEQ. ID. NO:16), the P domain of the Astrovirus (AstV P, SEQ. ID. NO:54), and the truncated P domain of NoV (NoV P⁻, SEQ. ID. NO:19). Other proteins that form dimers include, but are not limited to: Actin-binding protein p57/coronin-1; *Escherichia coli* galactose-1-phosphate uridylyltransferase (GALT); triose-phosphate isomerase; motor subunits of the kinesine; 14-3-3 proteins; G protein βγ-subunit; alcohol dehydrogenase; Factor XI (plasma thromboplastin antecedent); Factor XIII or fibrin stabilizing factor; fibrinogen; herpes simplex virus type 1 thymidine kinase (TK); T cell receptor delta chain; cell division protein FtsZ; carboxy terminus of Hsp70-interacting protein (CHIP); NSP3 protein; Heme activator protein; PAK1 autoregulatory domain; tubulin alpha subunit; tubulin beta subunit; adenovirus single-stranded DNA-binding protein; glutathione-S transferase; inositol monophosphatase; P protease of HIV (human immunodeficiency virus); Death-Associated Protein Kinase Catalytic Domain; F-box Proteins βTrCP1; *Bacillus subtilis* PyrR, a pyr RNA-binding attenuation protein and uracil phosphoribosyltransferase; Aldehyde dehydrogenase; I-CreI, a group I intron-encoded homing endonuclease; Peroxisomal 3-ketoacyl-CoA thiolase of *Saccharomyces cerevisiae*; Pig cytosolic aspartate aminotransferase; alkaline phosphatase; aldehyde oxidoreductase; yeast chorismate mutase; tet repressor; human interleukin-10; ferricytochrome c' of *Rhodospirillum molischianum*; copper amine oxidase of *Escherichia Coli*; NADH oxidase from *Thermus Thermophilus*; and the gene V protein from Ff phage, single-stranded DNA binding protein.

A non-limiting example of an oligomeric protein domain is the modified NoV P domain (NoV P⁺, SEQ. ID. NO:18).

Three types of complexes, the linear complex, the agglomerate complex, and the network complex, are obtained through fusion of these proteins in variable combinations. A monomeric peptide or protein can also be merged to dimeric proteins of the complexes. These enormous complexes can induced significantly higher immune responses than those induced by the free protein dimers, and can result in significantly increased antibody and T cell response, higher neutralizing activity, and enhanced protective immunity. Furthermore, the binding activity of dimeric fusion protein complexes, for example of the NoV P⁻ protein to its HBGA ligands, can be significantly increased through such complexes formation.

The intrinsic dimerization and multimerization natures of the certain proteins, including, but not limited to, the Norovirus (NoV) P protein (SEQ. ID. NO:17), are exploited. The P-domains of NoV P proteins and other P proteins that have a quaternary structure that causes them to spontaneously form dimers. In one embodiment of the present invention, a homo-dimeric fusion protein having two P-domain protein domains can be genetically engineered; each protein domain retaining its natural ability to assemble into a dimer. The resulting dimerization of the dimeric fusion proteins during expression in *E. Coli* provides a complex structure having large, even enormous molecular size and multivalence, and affords increased immunogenicity against NoV infection. The complex can be applied as a multivalent vaccine against multiple strains of human Norovirus (NoV), and also as a platform for foreign antigen presentation and vaccine development against other viral and bacterial pathogens.

In non-limiting examples, a GST-HEV P hetero-dimeric fusion protein (SEQ. ID. NO:1) is provided having a dimeric GST protein domain and a dimeric hepatitis E (HEV) protein domain fused by a linker polypeptide and a GST-NoV P⁺ hetero-dimeric fusion protein (SEQ. ID. NO:2) has a dimeric GST protein domain and a modified dimeric NoV P domain, fused by a linker polypeptide. See FIG. 8 and FIG. 9.

Figure 17A:
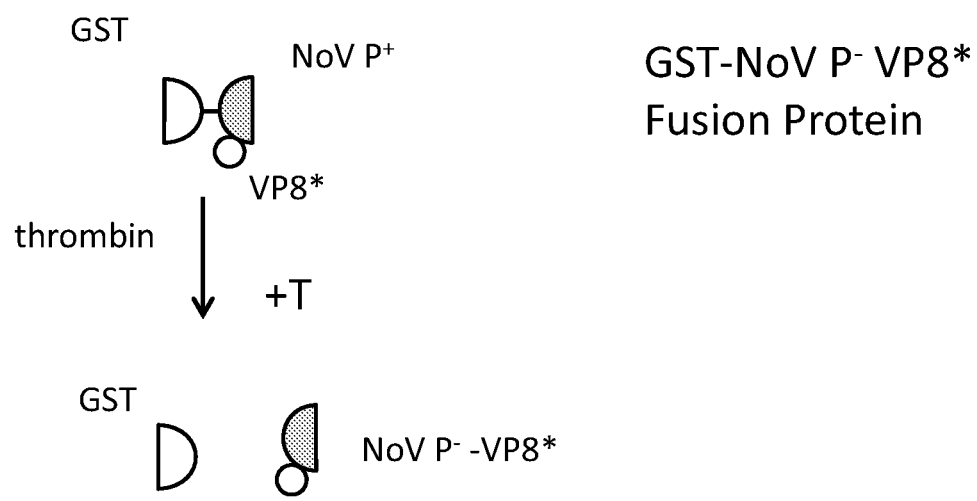
FIG. 17A is a schematic illustration of the GST-NoV P⁻-VP8* fusion protein (SEQ. ID. NOS:8), and its thrombin digestion (+T) into free GST (SEQ. ID. NO:20) and NoV P⁻-VP8* (SEQ. ID. NO:11) proteins.

In another aspect of the invention, a chimeric P particle vaccine is provided with a hetero-dimeric fusion protein. A non-limiting example is a hetero-dimeric fusion protein comprising the NoV P domain comprising either the M2e epitope of influenza virus antigen (SEQ. ID. NO:57, 23 aa) or the rotavirus VP8* antigen (SEQ. ID. NO:21, 159 aa) as shown in FIG. 17A. Each of the two chimeric vaccines can induce high titers of antigen-specific antibodies, specifically M2e- or VP8-specific antibodies in mice as well as humans, and protected mice and humans against challenges of influenza virus or rotavirus, respectively. In addition, the two chimeric vaccines can induce high titers of NoV P domain-specific antibody that block NoV-HBGA interaction. These two chimeric P particle vaccines provide a dual vaccine against NoV/influenza virus and NoV/rotavirus, respectively. See FIGS. 17B, 18 and 19. A hetero-dimeric fusion protein can also include a dimeric Astrovirus (AstV) protein domain fused to another dimeric protein domain.

The invention also includes a method for separating the linear, network, and/or agglomerated complex structures into one or more portions based on size or molecular weight. A size exclusion column is an apparatus and means for analyzing and identifying the molecular weight distribution of a sample. Other means for isolating portions by molecular weight can include filters and centrifugal devices.

The invention also includes compositions comprising a complex formed from dimer fusion proteins, and for inducing an immune response in an individual (human or mammal) against a pathogen, for example Norovirus. The method comprises the step of orally or parenterally administering to the individual at least one immunologically effective dose of the composition comprising any one of the complexes described herein, wherein the dose is effective in inducing the immune response in the individual. The resulting complexes made in accordance with the present invention using dimeric viral protein domains, are effective as models of multivalent vaccine development. Antisera raised after immunization with both linear/network complexes (by way of example, GST-NoV P- (387)-NoV P- (207) (SEQ. ID. NO:4) and NoV P- (387)-NoV P- (207) (SEQ. ID. NO:6)) can strongly block the attachment of two NoV surrogates, representing GII.4 VA387 and GII.9 VA207, to their HBGA carbohydrate receptors with binding significantly higher than corresponding antisera induced by the free NoV P- dimer.

The invention also includes compositions comprising a complex formed from dimer fusion proteins, for delivering therapeutic or diagnostic compounds, and a method comprising the step of orally, or intravascularly, or parenterally administering to the individual at least one therapeutically or diagnostically effective dose of the composition, wherein the dose is effective in treating, preventing, or ameliorating an injury, disease or condition, or diagnosing an injury, disease or condition in the individual.

The present invention provides a novel strategy to turn small proteins into enormous, polyvalent complexes for increased immunogenicity and functionality. The invention improves on the natures of dimerization and/or oligomerization of many proteins. Through recombinant DNA technology, two or more such proteins can be fused into one molecule, which can assemble into enormous complexes through intermolecular interactions among the homologous protein domains.

Although three types of complexes, namely linear, network and agglomerate complexes have been constructed, the present invention enables the formation of combinations of these and other complexes. The dimeric fusion proteins, and the complexes made therefrom, can be easily produced in *E. coli*, and most likely in other expression systems, allowing the invention's use in many fields of biomedicine.

An application of these novel polyvalent complexes is for improved immunogenicity of proteins. This has been shown by immunization of mice with the linear/network complexes in comparison with the same molar amount of the proteins in dimer form. The linear/network complexes induce significantly higher specific antibody and T cell responses than those induced by the dimer of the proteins. In an example, immunization of the NoV P- (387)-NoV P- (207) (SEQ. ID. NO:6) complexes to mice result in significantly higher titers of VA387 P domain- and VA207 P domain-specific antibody than those induced by a mixture of VA387 NoV P- and VA207 NoV P- dimers. Similar outcomes were also seen for CD4+ T cell responses. As a result, the mouse antisera after immunization with the NoV P-(387)-NoV P- (207) (SEQ. ID. NO:6) complex strongly blocked the attachment of both GII.4 VA387 and GII.9 VA207 NoVs to their HBGA receptors, an assay mimicking the inhibition of NoV infection that has been correlated with the serum antibody protection against NoV infection and illness. The increased immunogenicity of the linear/network complexes, compared with their dimers of the same protein, can be well explained by the polyvalence of the antigenic structure of the large complexes.

The increased immunogenic outcomes of the complexes demonstrates their broad use as multivalent vaccines, and demonstrate their use in the development of new multivalent vaccines. Both linear/network complexes, as formed from GST-NoV P- (387)-NoV P- (207) (SEQ. ID. NO:4) and NoV P- (387)-NoV P- (207) (SEQ. ID. NO:6), also provide effective bivalent vaccines against multiple pathogens, for example, both GII.4 and GI1.9 NoVs, which are two genetically and antigenically different NoVs. Notably, the two or three components of these complexes can be easily replaced with other antigens for novel bi- or tri-valent vaccines against other pathogens. For human NoVs, GII.4 and GII.3 are the two most predominant genotypes causing the vast majority of NoV epidemics. Thus, a complex containing the neutralizing antigens (NoV Ps) of both types has a broad protection against most, if not all, NoV infection. Construction of such complex vaccines include, but are not limited in any way to, complexes of GST-NoV Fr-HEV P (SEQ. ID. NO:14), NoV P$^-$-HEV P-AstV P (SEQ. ID. NO:55), AstV P-HEV P-VP8*(SEQ. ID. NO:56), and NoV P$^-$-HEV P (SEQ. ID. NO:15) complexes. The HEV P protein (SEQ. ID. NO:16) has been demonstrated as a potent antigen against human HIV infection and illness, and a NoV P$^-$-HEV P (SEQ. ID. NO:15) complex provides a bivalent vaccine against both NoV and HEV. This principle of multivalent vaccines can be extended to many other viral and bacterial pathogens for vaccine development, providing a new approach to combat infectious diseases.

The polyvalent feature of the large complexes also makes them potent platforms or carriers for a wide variety of proteins and antigens, and their properties and functions. Both a small peptide epitope and a large protein antigen can be successfully inserted into the protein domains of the linear/network complexes, resulting in significantly increased immunogenicity in humans and other mammals than those induced by the free epitope/antigen alone or by the dimer-presented epitope/antigen. The increased immunogenicity is indicated by the improved neutralizing activity and protective immunity of the chimeric complex vaccines against the corresponding pathogens compared with the free epitope/antigen, and establishes these chimeric complexes as a model and protocol for future improvement of immunogenicity of many other, and a wide range of, epitopes or antigens, and for multivalent vaccine development.

The enormous and polyvalent complexes can also increase the total outcomes of a protein function in a conventional function assay. For example, dramatically increased HBGA-binding signals in an ELISA-based binding assay of the NoV P$^-$-NoV P$^-$ complexes, and the associated increased accessibility of the polyvalent molecules, are provided compared with that of the NoV P$^-$ dimer.

The functional avidity through the polyvalence of the functional motifs of a molecule has been reported widely. For example, the binding activity of the NoV P dimer, the 12mer small P particle, the 24mer P particle and the 180mer-VLP increased along with the rise of their P domain valences. Similarly, human HBGAs in milk and saliva exist in two major populations. HBGAs that conjugate to the high molecular weight, polyvalent mucin-like backbones showed significantly higher binding activity to NoV VLPs compared to those HBGAs conjugated to the smaller molecules. The observed increase of the HBGA-binding activity is due to avidity effects of multiple interactions of the P proteins to HBGA receptors or an increased accessibility of the polyvalent NoV P$^-$ molecules by the detection antibody used in the EIA or both, and extends to other functional proteins as well to improve the sensitivity of functional assays.

Both protein production and the complex formation were highly efficient for the examined fusion proteins and similar properties are expected for many other proteins. However, both EM and gel filtration chromatography revealed heterogeneous sizes and shapes of the resulting complexes ranging from a few to thousands of subunits. Various techniques can be employed to control the size and shape of these complexes or, alternatively, how to separate the extremely large complexes from the small ones, such as by gel-filtration or other chromatography, because they are very different in immunogenicity, functionality and other properties.

The linker between the fused protein components can also be a factor that affects the yield and stability of the fusion proteins. A 6-residue linker (LVPRGS) pre-existed in GST Gene Fusion System (GE Healthcare Life Sciences) can be used between GST and the interested protein. In producing the GST-NoV P⁻-NoV P⁻ complexes, a 12-glycine linker between the two NoV Fs has better performance than a 6-glycine linker or an 8-residue (FLVPPTVE) hinge of NoV VP1. A linker should provide certain flexibility allowing the two neighboring protein components to fold into proper structures without interfering with each other, and a string of 12 glycines can serve this purpose.

EXAMPLES

1. Construction and Analysis of a Linear Complex

Figure 8:
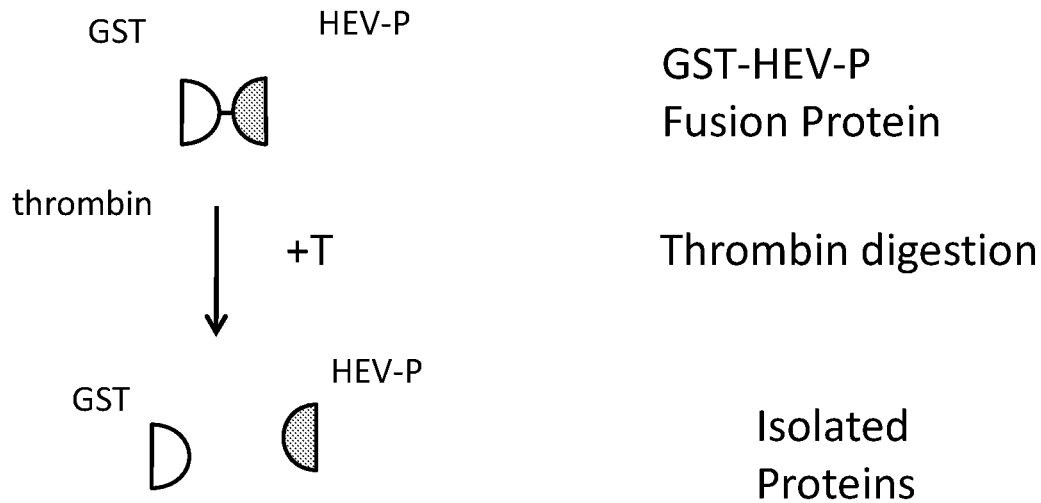
FIG. 8 is a schematic illustration of a GST-HEV P fusion protein (SEQ. ID. NO:1) and its thrombin digestion (+T) into free GST and HEV P (SEQ. ID. NO:16) proteins.
Figure 9:
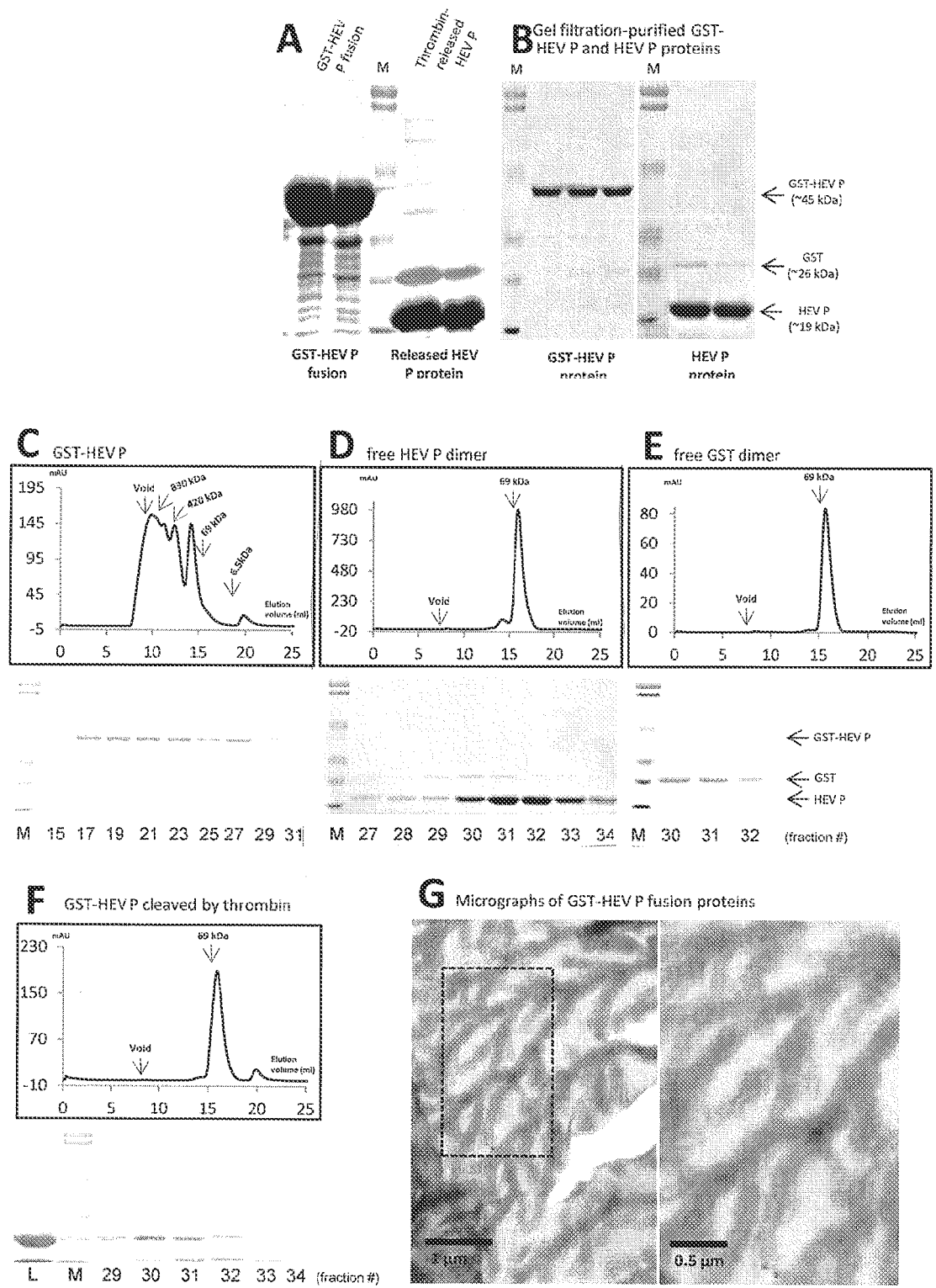
FIG. 9: Panel A shows the GST-HEV P fusion protein (left, SEQ. ID. NO:1) purified from a GST-affinity column and the HEV P protein (right, SEQ. ID. NO:16) eluted from the GST-affinity column after a thrombin digestion of the GST-HEV P fusion protein (SEQ. ID. NO:1) on the beads of the column; Panel B shows the GST-HEV P fusion protein (left) and the HEV P protein (right) after being further purified through a gel-filtration chromatography; Panel C shows the elution curve of gel filtration chromatography of GST-HEV P dimeric fusion prior to thrombin digestion; Panel D shows the gel filtration chromatography elution curve of free HEV P protein (SEQ. ID. NO:16) after thrombin digestion; Panel E shows the gel filtration chromatography elution curve of free GST after thrombin digestion; Panel F shows the elution curves of gel filtration chromatography of the GST-HEV P protein complex after thrombin digestion; Panel G shows electron micrographs of negatively stained GST-HEV P fusion protein complex, revealing large linear molecules, where the right panel is an enlargement of the rectangular labeled region on the left panel.

A linear complex is formed from GST-HEV P fusion protein (SEQ. ID. NO:1) having a linker 16 that is digestible by thrombin, which has a structure illustrated by FIG. 1, wherein the GST monomer protein is the dimeric unit 12 and the HEV-P monomer protein is the dimeric unit 14. FIG. 8 illustrates the digestion of the linker of the GST-HEV-P fusion protein (SEQ. ID. NO:1) at a cleavage site, such as with a thrombin (+T), to release the GST and HEV-P monomers. Glutathione S-transferase (GST) of *Schistosoma japonicum* (~26 kDa) was fused with the P domain of Hepatitis E virus (HEV-P, 19 kDa), designated as GST-HEV-P protein (~45 kDa, FIG. 9, Panel A, SEQ. ID. NO:1). Dimerization individually of both GST and HEV-P was known previously and confirmed by the gel filtration analysis. The GST-HEV P fusion protein (SEQ. ID. NO:1) was expressed well in *E. coli*, and assembled into the extremely large linear/network complexes. FIG. 9 Panel A shows the GST-HEV P fusion protein (left, SEQ. ID. NO:1) purified from a GST-affinity column and the HEV P protein (SEQ. ID. NO:16, right) eluted from the GST-affinity column after a thrombin digestion of the GST-HEV P fusion protein (SEQ. ID. NO:1) on the beads of the column. FIG. 9 Panel B shows the HEV P protein (SEQ. ID. NO:16) after being further purified through a gel-filtration chromatography. The position of the GST-HEV P fusion protein (~45 kDa, SEQ. ID. NO:1), GST (~26 kDa) and HEV P protein (~19 kDa, SEQ. ID. NO:16) are indicated. The letter "M" represents a pre-stained protein marker (Bio-Rad, low range), with bands from top to bottom representing 113, 92, 52, 34, 29, and 21 kDa.

FIG. 9 Panel C shows the elution curve of gel filtration chromatography of the GST-HEV P linear complex composition (prior to thrombin digestion). The gel filtration columns were calibrated by the Gel Filtration Calibration Kit (GE Healthcare Life Sciences) and the recombinant P particle, small P particle and P dimer of Norovirus (VA387). The elution positions of blue Dextran 2000 (void), the P particle (~830 kDa), the small P particle (420 kDa), P dimer (~69 kDa) and aprotinin (~6.5 kDa) were indicated. The major peaks of protein elution were analyzed by SDS-PAGE shown below the corresponding elution curves of gel filtration. The GST-HEV P fusion protein (SEQ. ID. NO:1) formed a collection of large complexes as shown by the major peaks at and near the void volume of the size-exclusion column Superdex 200 (10/300 GL, GE Healthcare Life Sciences, consisting of sizes greater, and much greater, than 400 kDa.

FIG. 9 Panel D shows the gel filtration chromatography elution curve of free HEV P (SEQ. ID. NO:16) after thrombin digestion, showing a major portion of HEV P dimer (38 kDa, to the right of the 69 kDa marker), and a smaller portion which is suspected to be a trimer or other multi-mer of HEV P. FIG. 9 Panel E shows the gel filtration chromatography elution curve of free GST after thrombin digestion, which formed defined single peaks at ~39 kDa and ~52 kDa representing the P dimers of the two proteins (HiLoad 16/60, GE Healthcare Life Sciences) FIG. 9 panel F shows the elution curves of gel filtration chromatography of GST-HEV P after thrombin digestion, and FIG. 9 Panel G shows electron micrographs of negatively stained GST-HEV P protein, revealing large linear molecules, and possibly some minor branching. The right panel of FIG. 9 Panel G is an enlargement of the rectangular labeled region on the left, which may illustrate branching in the complex associated with a portion of the HEV P domains forming a trimer or other multimer, inducing branching, as illustrated in FIG. 2. Electron microscopy (EM) observation demonstrated the GST-HEV P protein (SEQ. ID. NO:1) as linear complexes with length in micrometers and the GST-HEV P subunits can be clearly recognized as round balls (FIG. 9 Panel G, right side). As anticipated, thrombin cleavage of GST-HEV P protein into free GST and HEV P proteins (FIG. 8) completely destroyed the large complexes, resulting in free GST dimers (~52 kDa) and HEV P dimers (~38 kDa) (FIG. 9 Panels C, D, E). EM inspection of the GST and HEV P solutions did not reveal large complexes (data not shown), confirming the results of the gel filtration.

Figure 14A:
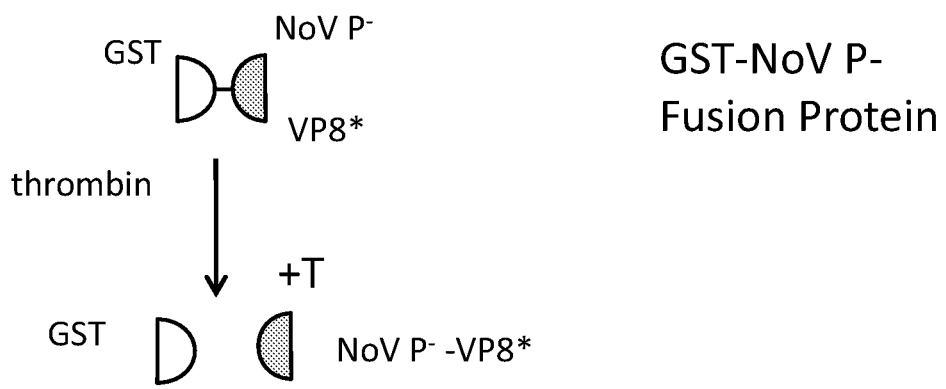
FIG. 14A is a schematic illustration of the GST-NoV P$^-$ fusion protein (SEQ. ID. NO:3) and its thrombin digestion (+T) into free NoV P$^-$ (SEQ. ID. NO:19) and GST (SEQ. ID. NO:20) proteins.
Figure 14B:
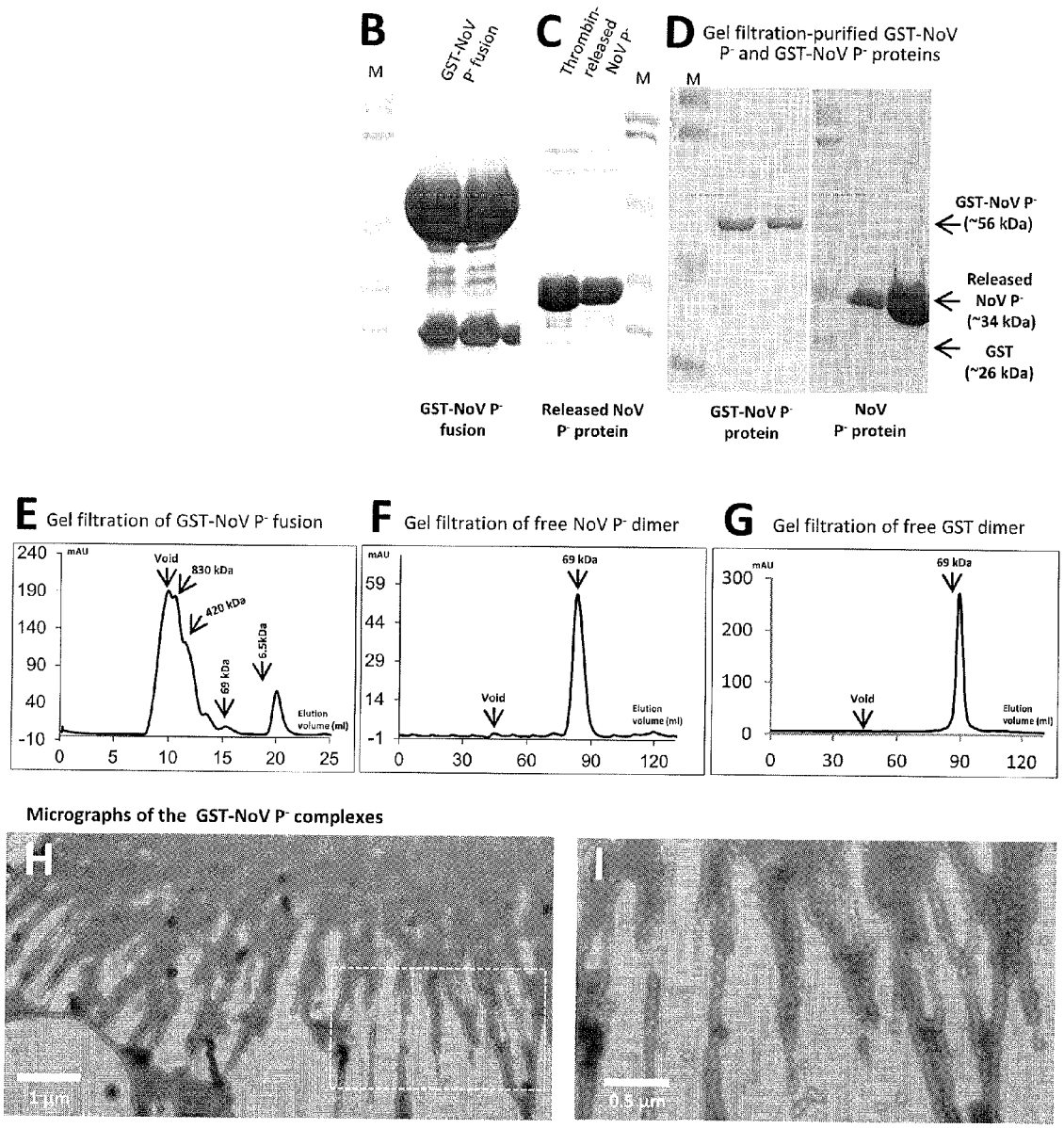
FIG. 14B: Panel B shows the GST-affinity column-purified GST-NoV P$^-$ protein; Panel C shows the NoV P$^-$ protein (SEQ. ID. NO:19) eluted from the GST-affinity column after a thrombin digestion of the GST-NoV P$^-$ fusion protein (SEQ. ID. NO:3) on the beads of the column; Panel D shows the P protein from Panel C after being further purified by a gel-filtration chromatography; Panel E shows the elution curve of gel filtration chromatography of the GST-NoV P$^-$; Panel F shows the elution curve of the free NoV P$^-$ dimer; Panel G shows the elution curve of the GST proteins; Panel H shows an electron micrograph of negatively stained GST NoV P$^-$ protein, revealing large linear molecules; Panel I shows an enlarged view of the rectangular-labeled region in Panel H.

Linear complexes can also be formed by another fusion protein, the GST-NoV P⁻ protein (SEQ. ID. NO:3). NoV P⁻ is a shortened P domain of Norovirus (NoV) that forms dimers. After being expressed in *E. coli*, the formation of GST-NoV P⁻ complexes (FIG. 14B Panels H,I) from the GST-NoV P⁻ fusion proteins (SEQ. ID. NO:3, illustrated in FIG. 14A) was confirmed by gel filtration (FIG. 14B Panels B-G) and EM (FIG. 14B Panels H,I). The large complexes disappeared completely after the GST-NoV P⁻ fusion proteins (SEQ. ID. NO:3) were cleaved by thrombin, resulting in free dimers of GST (~52 kDa) and NoV P⁻ (~69 kDa), respectively (FIG. 14B Panel F and G). These data supported our hypothesis that a fusion of the two dimeric proteins results in large linear complexes.

2. Formation and Analysis of an Agglomerate Complex

Figure 10:
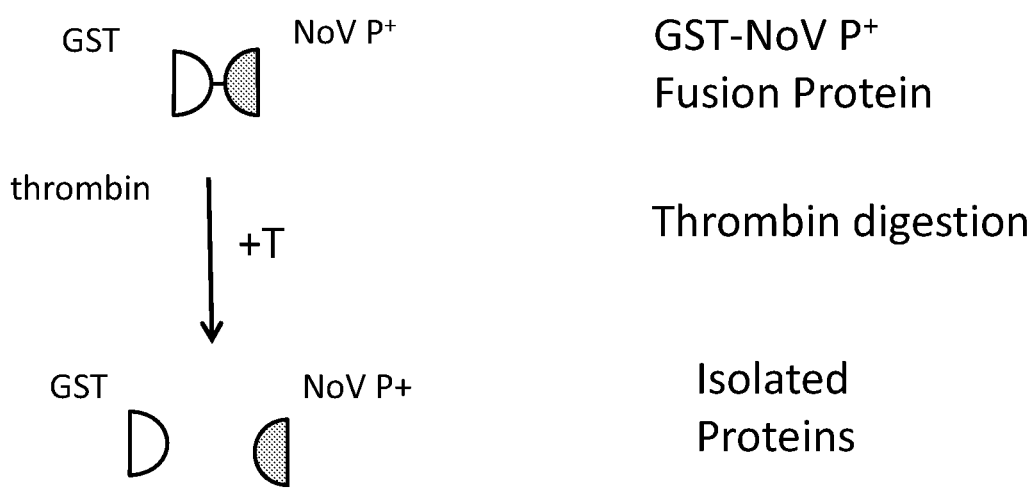
FIG. 10 is a schematic illustration of the GST-NoV P$^+$ fusion protein (SEQ. ID. NO:2) and the release of the NoV P$^+$ protein by a thrombin digestion (+T) of the GST-NoV P$^+$ fusion protein (SEQ. ID. NO:2).
Figure 11:
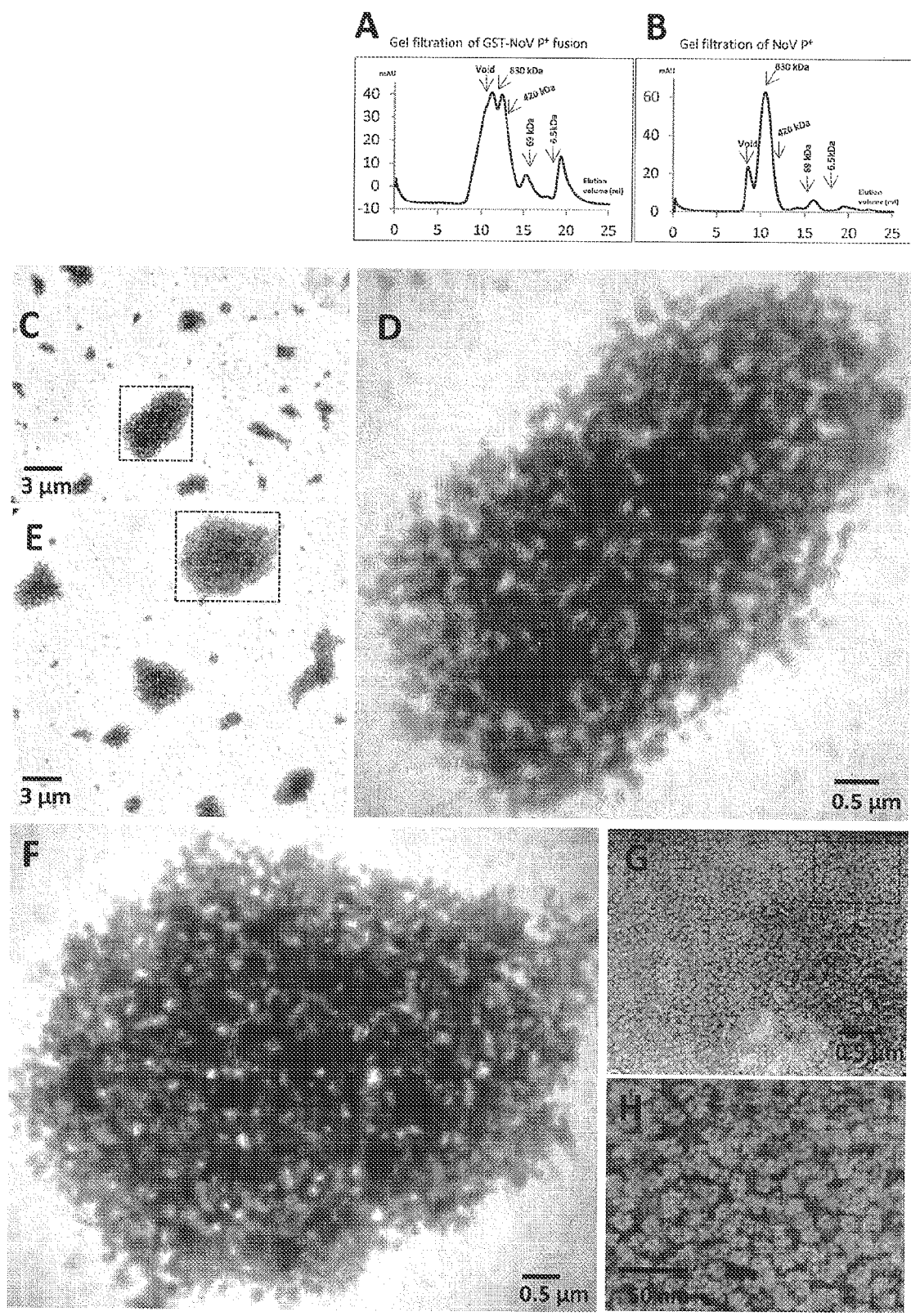
FIG. 11: Panel A shows the elution curve of the gel filtration chromatography of the GST-NoV P$^+$ protein complex; Panel B shows the elution curve of the gel filtration chromatography of the NoV P$^+$ proteins (SEQ. ID. NO:18) after thrombin digestion; Panels 11C to H show electron micrographs of negatively stained GST-NoV P$^+$ fusion proteins (SEQ. ID. NO:2, panels 11C to 11F) and of NoV P$^+$ proteins (SEQ. ID. NO:18, panels. 11G and 11H).
Figure 12:
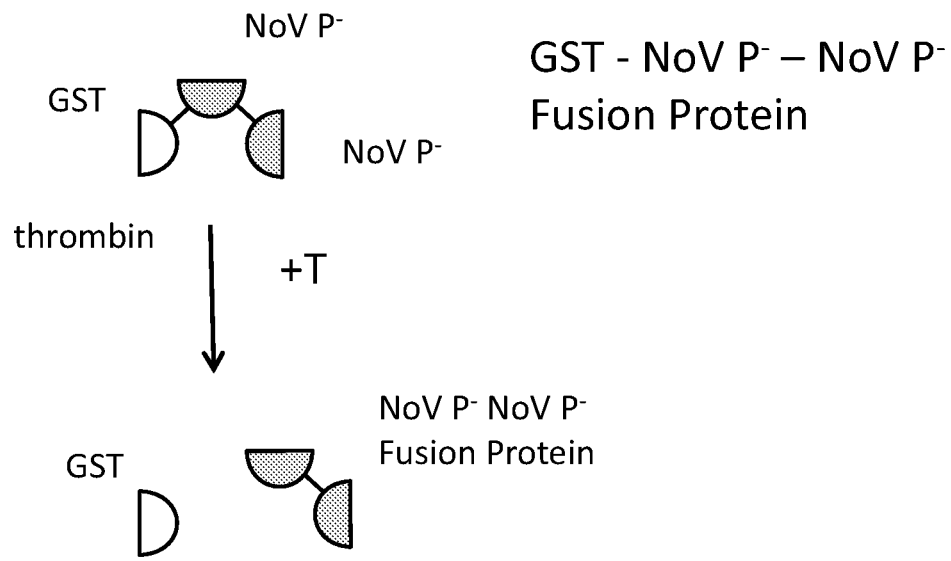
FIG. 12 is a schematic illustration of the GST-NoV P$^-$-NoV P$^-$ fusion protein (SEQ. ID. NOS:4 and 5) and its thrombin digestion (+T) into free GST (SEQ. ID. NO:20) and a tandem repeat of NoV P$^-$ (NoV P$^-$-NoV P$^-$) protein (SEQ. ID. NOS:6 and 7).

An agglomerate complex is formed from GST-NoV P⁺ fusion protein (SEQ. ID. NO:2) having a linker 56 that is digestible by thrombin, which has a structure illustrated by FIG. 4, wherein the GST monomer protein is the dimeric unit 52 and NoV P⁺ is the dimeric unit 54 that is capable of oligomerizing. FIG. 10 shows the digestion of the GST-NoV P⁺ fusion protein (SEQ. ID. NO:2) with thrombin (+T) to the GST and NoV P⁺ monomers. Fusion of GST with NoV P⁺ can be produced in *E. coli* and forms large complexes as shown by both gel filtration chromatography (FIG. 11 Panel A) and EM (FIG. 11 Panels C-F). FIG. 11 Panel A shows the elution curve of the gel filtration chromatography of the GST-NoV P⁺; The GST-NoV P⁺ protein (SEQ. ID. NO:2) formed major peaks in and near the void volume, while FIG.

11 Panel B shows the elution curve of the gel filtration chromatography of the digested NoV P+ proteins. Thrombin-released NoV P+ forms an anticipated major peak at ~830 kDa shown in FIG. 11 Panel B, corresponding to the 24mer P particles. The gel filtration chromatography was done through the size exclusion column Superdex 200 (10/300 GL, GE Healthcare Life Sciences), the columns were calibrated by the Gel Filtration Calibration Kit (GE Healthcare Life Sciences) and the recombinant P particle, small P particle and P dimer of Norovirus (VA387), and the elution positions of blue Dextran 2000 (~2000 kDa, void), the P particle (~830 kDa), the small P particle (420 kDa), P dimer (~69 kDa) and aprotinin (~6.5 kDa) were indicated.

FIG. 11 Panels C to H show electron micrographs (EM) of negatively stained GST-NoV P+ proteins (SEQ. ID. NO:2 FIG. 11 Panels C to F) and NoV P+ proteins (FIG. 11 Panels G and H). GST-NoV P+ fusion proteins form agglomerate complexes in variable large sizes (FIG. 11 Panels C and E), while the NoV P+ free proteins form the 24mer P particle at ~20 nm in size (FIG. 11 Panels G and H). The two largest complexes in FIG. 11 Panels C and E were enlarged in FIG. 11 Panels D and F, respectively, and the rectangular labeled region in FIG. 11 Panel G is enlarged in FIG. 11 Panel H.

EM revealed the GST-NoV P+ fusion protein (SEQ. ID. NO:2) as agglomerate complexes with different sizes, as shown in FIG. 11 Panels C to F. The larger complexes reached a diameter greater than 10 micrometers, likely containing over thousands of GST-NoV P+ fusion protein units. Enlargement of two large agglomerate complexes revealed large collections of many bended lines going to all directions (FIG. 11 Panels D and F), which can be formed by NoV P+ oligomers 54 linked to the GST dimers 52 (FIG. 4). FIG. 11 Panel B shows primarily 24-mer NoV P+, and a low portion (~5%) of P dimer, shown as a small peak just to the right of the 69 kDa marker. NoV P+ can also form 12mers, 18mers and 36mers at certain conditions.

3. Formation and Analysis of a Network Complex

Figure 13:
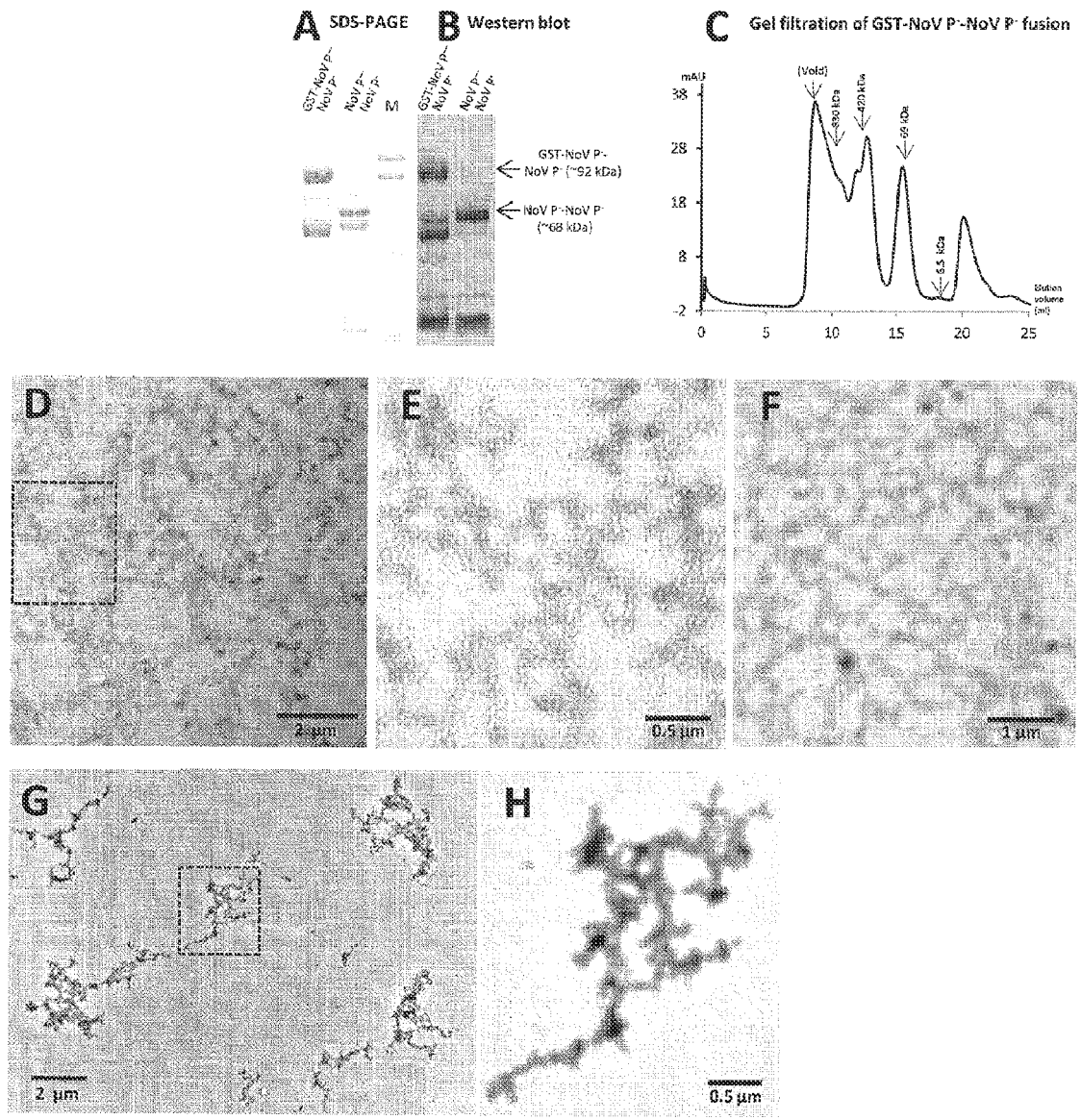
FIG. 13: Panel A shows expression and purification of the GST-NoV P$^-$-NoV P$^-$ dimeric fusion protein, and the NoV P$^-$-NoV P$^-$ dimer protein after thrombin digestion M represents a pre-stained protein marker (Bio-Rad, low range), with bands from top to bottom representing 113, 92, 52, and 34 kDa; Panel B shows bands of GST-NoV P$^-$-NoV P$^-$ tri-heterotypic fusion protein (SEQ. ID. NOS:4 and 5, ~92 kDa) and NoV P$^-$-NoV P$^-$ di-homotypic fusion protein ((SEQ. ID. NOS:6 and 7, ~68 kDa); Panel C shows elution curves of a gel filtration chromatography of GST-NoV P$^-$-NoV P$^-$ network complex; Panels D to H show EM's (electron micrographs) of negatively stained GST-NoV P$^-$-NoV P$^-$ (Panels D and E), NoV P$^-$-NoV P$^-$ (Panel F) and gel filtration-purified GST-NoV P$^-$-NoV P$^-$ protein network complexes from the void volume of the gel filtration (Panels G and H).

A. A branching, network complex is formed as a ~92 kDa GST-NoV P−-NoV P− fusion protein comprising GST and tandem NoV P−, having a linkers 37 and 38 in a structure illustrated by FIG. 2, wherein linker 37 between GST and the first NoV P− is digestible by thrombin, wherein the GST monomer protein is the dimeric unit 32, and the NoV P− monomer protein are the dimeric units 34 and 36. FIG. 13 Panels A-H show the production and characterization of these network complexes. The NoV P− protein domain is of virus species VA387 (GII.4) FIG. 13 Panel A shows expression and purification of the GST-NoV P−-NoV P− complex and of the NoV P−-NoV P− digested dimeric protein. FIG. 13 Panel B shows bands of GST-NoV P−-NoV P− (~92 kDa) complex (left) and of the NoV P−-NoV P− (~68 kDa) dimer (right). Lane M represents a pre-stained protein marker (Bio-Rad, low range), with bands from top to bottom representing 113, 92, 52, and 34 kDa. FIG. 13 Panel C shows elution curves of a gel filtration chromatography of GST-NoV P−-NoV P− complex. The majority of the protein was eluted in the void volume of the size-exclusion column Superdex 200 (10/300 GL, GE Healthcare Life Sciences), indicating complexes of significant, enormous, molecular weight and size. The gel filtration columns were calibrated by the Gel Filtration Calibration Kit (GE Healthcare Life Sciences) and the recombinant P particle, small P particle and P dimer of Norovirus (VA387). The elution positions of blue Dextran 2000 (~2000 kDa, void) the P particle (~830 kDa), the small P particle (420 kDa), the P dimer (~69 kDa) and aprotinin (~6.5 kDa) were indicated.

FIG. 13 Panels D to H show EM's (electron micrographs) of negatively stained GST-NoV P−-NoV P− complex (FIG. 13 Panels D and E), and of gel filtration-purified GST-NoV P−-NoV P− protein complexes from the void volume of the gel filtration (FIG. 13 Panels G and H). Enormous, complicated network complexes were seen in each micrograph. Even after removal of the GST in the network complex by a thrombin treatment, the resulting remaining NoV P−-NoV P− linear complex remained an enormous linear/network complexes (FIG. 13 Panel F).

B. Two other similar fusion proteins as in Example 3A immediately above, with P protein domains of different NoV strains, were made. One was the tri-heterotypic GST-NoV P− (GII.4 VA387)-NoV P− (GII.9 VA207) fusion protein [SEQ. ID. NO:4, designated as GST-NoV P− (387)-NoV P− (207)]. The other was and the tri-heterotypic GST-NoV P− (GII.4 VA387)-NoV P− (GI.3 VA115) fusion protein [SEQ. ID. NO:5, designated as GST-NoV (387)-NoV P− (115)]. These two fusion proteins were also tested and similar results to above were obtained, as shown in Table 1.

4. Complex Size Selection and Exclusion

In Example 3 above, the resulting dimerization of the fusion proteins, shown in FIG. 14 Panels F and G, are compared with the gel filtration product shown in FIG. 14 Panels D and E, from which smaller complexes have been separated and excluded from the large complexes shown. These results verify that the resulting complexes can be classified and separated based on size and molecular weight, and that gel filtration is one effective purification tool for separation of the enormous complexes from the smaller ones.

TABLE 1

Properties of variable linear/network complexes constructed and tested

| Names of complexes | Molecular weights (kDa) | Complex sizes (kDa) | Complexity | Yield (mg/liter culture) | Increased immuno-genicity | Increased neutral-ization |
|---|---|---|---|---|---|---|
| GST (SEQ. ID. NO: 20) | ~26 | ~52 | dimer | >20 | — | — |
| HEV P domain (HEV P) (SEQ. ID. NO: 16) | ~19 | ~38 | dimer | >20 | — | — |
| GST-HEV P domain (GST-HEV P, SEQ. ID. NO: 1) | ~45 | >400 | linear complexes | >20 | — | — |
| NoV P polypeptide (NoV P−) (SEQ. ID. NO: 19) | ~34.5 | ~69 | dimer | >20 | — | — |
| GST-NoV P polypeptide (GST-NoV P−, SEQ. ID. NO: 3) | ~60.5 | >800 | linear complexes | >20 | — | — |

TABLE 1-continued

Properties of variable linear/network complexes constructed and tested

| Names of complexes | Molecular weights (kDa) | Complex sizes (kDa) | Complexity | Yield (mg/liter culture) | Increased immuno-genicity | Increased neutral-ization |
|---|---|---|---|---|---|---|
| NoV P domain-RGDCFC (NoV P⁺) (SEQ. ID. NO: 18) | ~35 | ~70 | Dimer, 24mer | >15 | — | — |
| GST-NoVP-RGDCFC (GST-NoV P⁺, SEQ. ID. NO: 2) | ~61 | >800 | linear/agglomerate complexes | >20 | — | — |
| NoV P⁻-NoV P⁻ (SEQ. ID. NO: 6 and/or SEQ. ID. NO: 7) | ~68 | >800 | linear complexes | ~4 | yes | yes |
| GST-NoV P⁻-NoV P⁻(VA387, GII.4)(SEQ. ID. NO: 5) | ~94 | >800 | network complexes | ~5 | yes | yes |
| NoV P⁻(GII.4)-NoV P⁻(GII.9) (SEQ. ID. NO: 6) | ~68 | >800 | linear complexes | ~4 | yes | yes |
| GST-NoV P⁻(GII.4)-NoV P⁻(GII.9) (SEQ. ID. NO: 4) | ~94 | >800 | network complexes | ~4 | yes | yes |
| Rotavirus VP8* (SEQ. ID. NO: 21) | ~18 | — | monomer | >20 | — | — |
| GST-NoV P⁺-VP8* (loop 2) (SEQ. ID. NO: 8) | ~78.5 | >800 | linear complexes | >15 | yes | yes |
| GST-NoV P⁻-VP8* (C-end) (SEQ. ID. NO: 9) | ~78.5 | 400->800 | linear complexes | >15 | — | — |
| GST-NoV P⁻-M2e (loop 2) (SEQ. ID. NO: 10) | ~53 | >800 | linear/network complexes | >20 | yes | yes |
| GST-NoV P-GST (SEQ. ID. NO: 13) | ~87 | >800 | linear/network complexes | ~2 | — | — |

5. Antibody and T Cell Response to Complexes

Figures 1, 15:
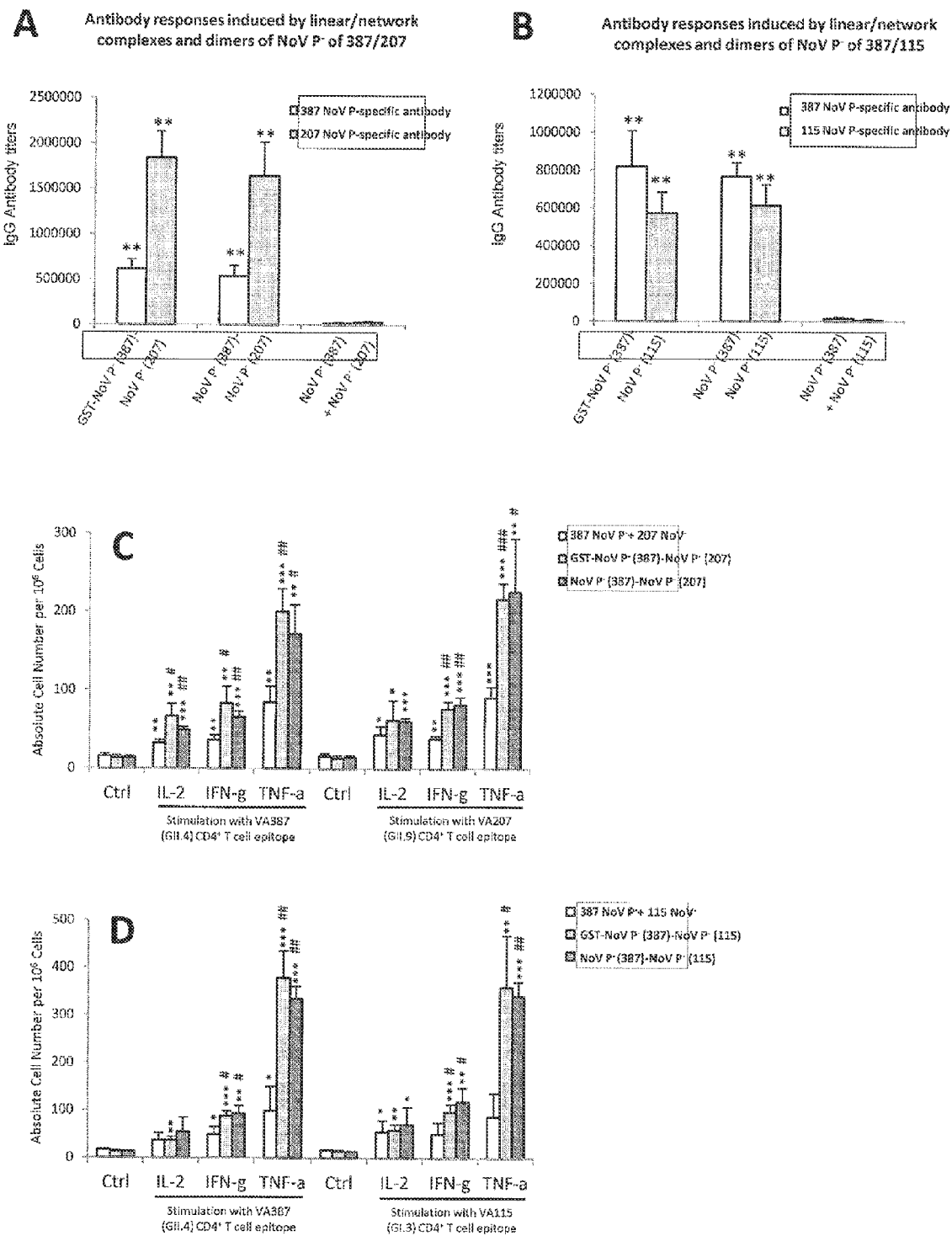
Figures 2, 15:
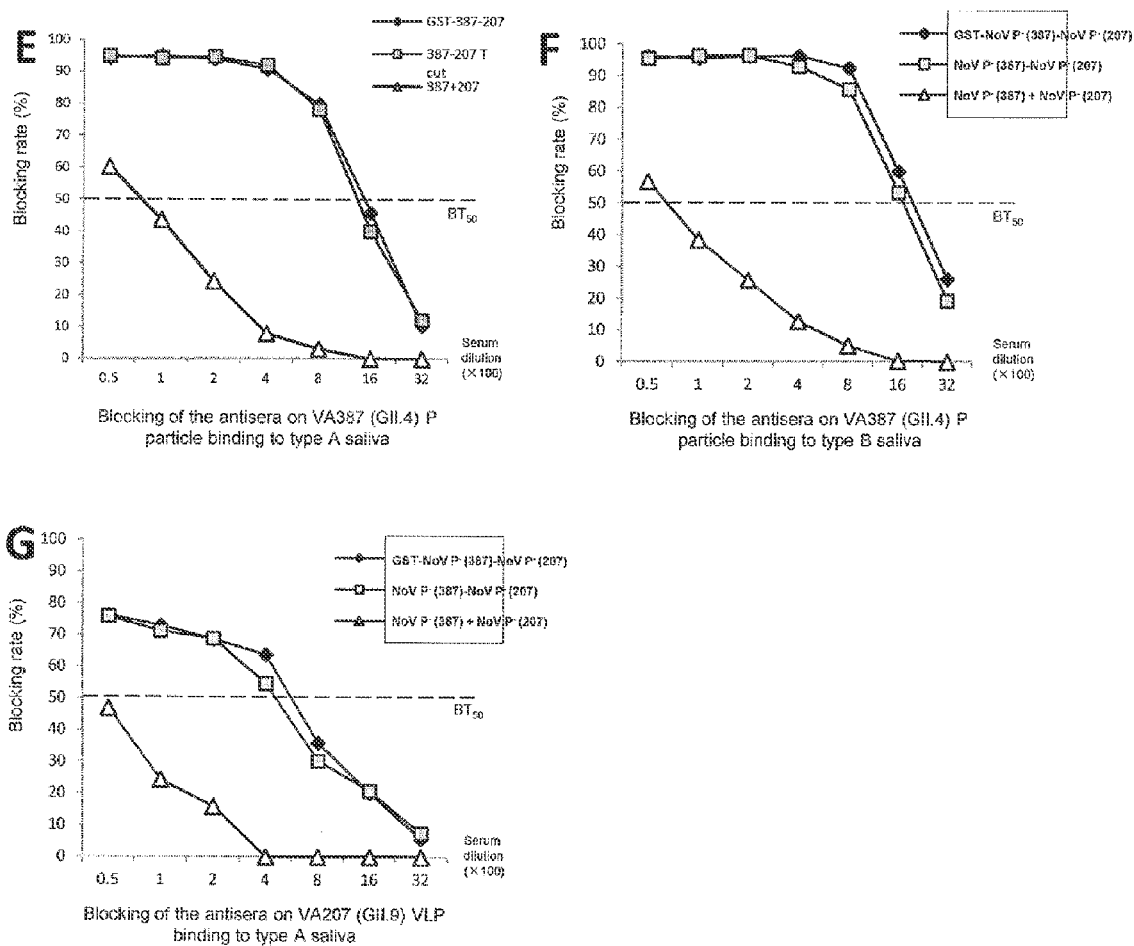

The complexes produced in the Examples increased antibody and T cell responses of the protein components. The linear/network complexes of the invention significantly increase the immunogenicity of the protein components. This is proven by preclinical mouse immunization trials using same molar amounts of the NoV P- proteins in forms of linear/network complexes [GST-NoV P- (387)-NoV P- (207) (SEQ. ID. NO:4), GST-NoV P- (387)-NoV P-(115) (SEQ. ID. NO:5), NoV- (387)-NoV P- (207) (SEQ. ID. NO:6) and NoV P- (387)-NoV P-(115) (SEQ. ID. NO:7)] and the corresponding free NoV P- dimers. Specifically, FIG. 15-1 Panel A shows that antibody titers of mouse sera against NoV P⁻ domains of VA387 (GII.4) and VA207 (GII.9) after immunization with GST-NoV P- (387)-NoV P- (207) (SEQ. ID. NO:4) and NoV P- (387)-NoV P- (207) (SEQ. ID. NO:6) complexes were significantly higher than those induced by the corresponding NoV P- dimers. FIG. 15-1 Panel B shows antibody titers of the mouse sera against NoV P⁻ domains of VA387 and VA115 (GI.3) after immunization with GST-NoV P- (387)-NoV P- (115) (SEQ. ID. NO:5) and NoV P- (387)-NoV P- (115) (SEQ. ID. NO:7) complexes were significantly higher than those induced by the corresponding NoV P- dimers. Equal molar amounts of GST-NoV P- (387)-NoV P- (VA207/115), NoV P- (387)-NoV P- (VA207/115) and a mixture NoV P- (387) and NoV P- (VA207/115) were immunized to mice (N=8 mice/group) intranasally without an adjuvant. Gel filtration-purified NoV P-s were used to measure the NoV P-specific antibody. The titers were determined via an end-dilution approach.

FIG. 15-1 Panel C shows NoV P domain-specific CD4+ T cell responses post immunization. VA387 and VA207-specific CD4+ T cell responses after immunization with GST-NoV P- (387)-NoV P- (207) (SEQ. ID. NO:4) and NoV P- (387)-NoV P- (207) (SEQ. ID. NO:6) complexes were significantly higher than those induced by the corresponding NoV P-dimers. FIG. 15-1 Panel D shows NoV P domain-specific CD4+ T cell responses post immunization. VA387 and VA115-specific CD4+ T cell responses after immunization with GST-NoV P- (387)-NoV P- (115) (SEQ. ID. NO:5) and NoV P- (387)-NoV P- (115) (SEQ. ID. NO:7) complexes were significantly higher than those induced by the corresponding NoV P-dimers. Equal molar amounts of GST-NoV P- (387)-NoV P- (VA207/115), NoV P- (387)-NoV P- (VA207/115) and a mixture NoV P- (387) and NoV P- (VA207/115) were immunized to mice (N=3 mice/group) intranasally without an adjuvant. After a stimulation of the splenocytes with a NoV P domain-specific CD4+ T cell epitope, the resulting CD4+ T cell cytokines IL-2, IFN-γ or TNF-α were measured by intracellular cytokine staining. Cytokines from the GST-NoV P- (387)-NoV P- (VA207/115)-immunized mice were shown in red, those from NoV P- (387)-NoV P- (VA207/115)-immunized mice in green, and those from the NoV P- dimer-immunized mice in blue. The cytokine levels from unimmunized mice were used as negative control (Ctrl). Data was presented as absolute cytokine-producing cell numbers per 106 cells. The statistical significances between the data of the immunized groups and unimmunized control are shown by start symbols (* P<0.05,  P<0.01, * P<0.001), while those between the data of linear/complex-immunized groups (red and green) and the NoV P- dimer control (blue) are shown by # (# P<0.05, ## P<0.01, ### P<0.001).

FIG. 15-2 Panels E, F and G illustrate blocking rates of the linear/network complex-induced antisera, which blocked binding of NoVs to histo-blood group antigens (HBGAs). Mouse antisera after immunization with GST-NoV P- (387)-NoV P- (207) (SEQ. ID. NO:4) and NoV P- (387)-NoV P- (207) (SEQ. ID. NO:6) showed strong blocking activity on binding of NoV P particles of VA387 (GII.4, Panels E and F) and VLP of VA207 (GII.9, Panel G) to type A saliva samples (Panels E and G) and type B saliva samples (Panel F). These blockades were significantly higher than those of the antisera after immunization with NoV P-dimer of VA387 and VA207. The levels of Blockade Titer 50% (BT50) titers were defined as the lowest percentage of sera tested that blocked 50% of binding compared to levels determined in the absence of antibody pretreatment. All data were averages of triplicate experiments.

Mice (N=8 mice/group) after immunization with the linear/network complexes revealed significantly higher antibody and T cell responses specific to the NoV P- proteins (SEQ. ID. NO:19) than those induced by the corresponding free NoV P- dimers. The antibody response to the GST component (SEQ. ID. NO:20) was also tested, revealing similar results (data not shown). In all cases, whether GST was removed from the linear/network immunogens did not change the immune responses significantly. These data support the notion that the polyvalent complexes increased the immunogenicity of the protein components significantly.

The resulting complexes serve as models of and structures for multivalent vaccine development. The above antisera were examined for their capabilities in blocking on binding of NoV VLPs or P particles, the two NoV surrogates, to their HBGA receptors. The results showed that antisera after immunization with both linear/network complexes of GST-NoV P- (387)-NoV P- (207) (SEQ. ID. NO:4) and NoV P- (387)-NoV P- (207) (SEQ. ID. NO:6) strongly blocked the attachment of two NoV surrogates, representing GII.4 VA387 and GII.9 VA207, to their carbohydrate receptors with BT50s of ~1:1600 for VA387 (FIG. 15-2 Panels E and F), or 1:400 for VA207 (FIG. 15-2 Panel G), respectively. These BT50s were significantly higher than those of the antisera induced by the free NoV P- dimer, which were ~1:50-100 for VA387 and <1:50 for VA207, respectively. These data indicated that the linear/network complexes serve as models for multivalent vaccine development.

Figure 16:
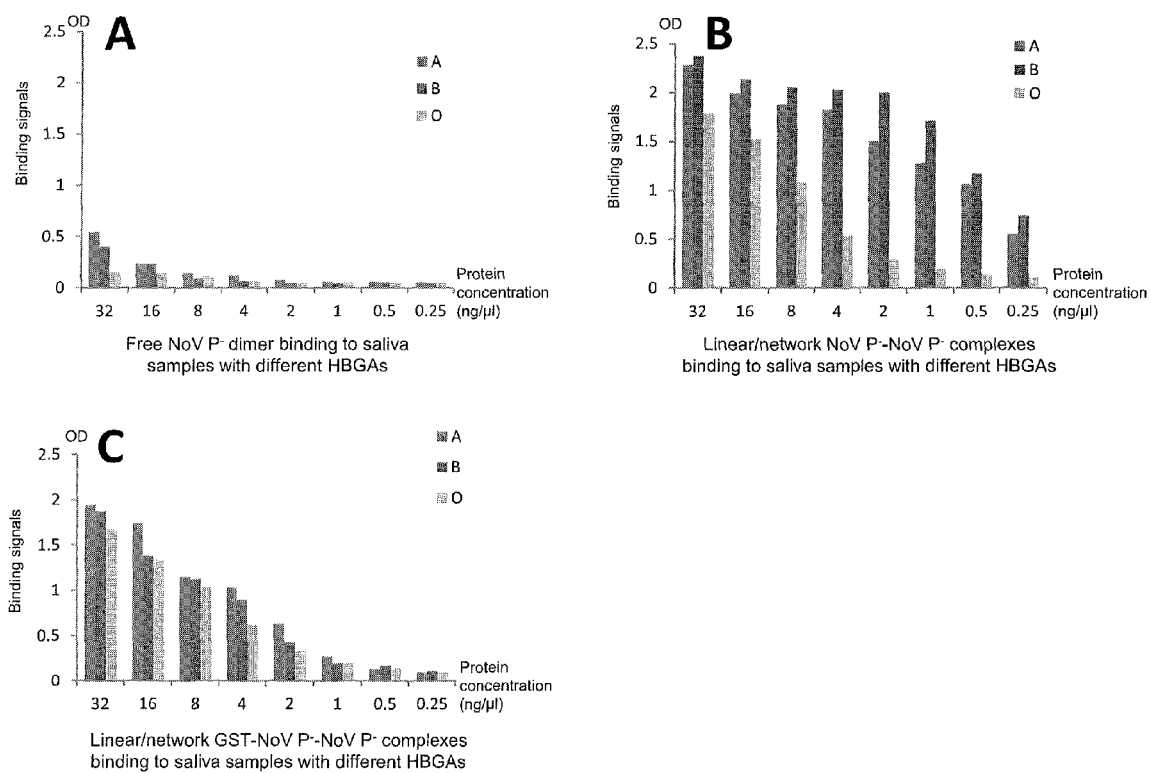
FIG. 16: Panel A illustrates that the free NoV P⁻ dimer showed only marginal binding activity to the saliva samples; Panels B and C illustrate that the linear/network P complexes NoV P⁻-NoV P⁻ (Panel B) and the GST-NoV P⁻-NoV P⁻ (Panel C) exhibit significantly increased binding activity to the same saliva samples, respectively.

6. Complexes Provide Increased Binding Activity Compared to Protein Domain Monomers As shown in FIG. 16 Panels A-C, linear/network complexes of NoV P domain (SEQ. ID. NO:17) exhibited increased binding activity to type A, B and O saliva samples that were defined to contain H, A and B antigens, respectively. In FIG. 16 Panel A, the free NoV P-dimer showed only marginal binding activity to the saliva samples, such that the NoV P- dimer itself possesses weak binding to the HBGA receptors. The linear/network P complexes NoV P--NoV P- (FIG. 16 Panel B) and the GST-NoV P--NoV P- (FIG. 16 Panel C) exhibited significantly increased binding activity to the same saliva samples, respectively. All data were averages of triplicate experiments. The linear/network complex of NoV P--NoV P- exhibited a radically increased binding activity than that of the NoV dimer in a saliva-based binding assay (FIG. 16 Panel B). The GST-NoV P--NoV P- complexes also showed increased binding activity (FIG. 16 Panel C), but lower than that of the NoV P--NoV P- complexes, suggesting a possible negative impact of the GST on the binding function of the complexes. Generally, formation of polyvalent complex can be an effective approach to increase the functionality of a protein.

7. A Monomeric Peptide or Protein can be Merged to the Complexes

A. A complex was formed from GST-NoV P- fusion protein (SEQ. ID. NO:3,) having a linker 16 that is digestible by thrombin, which has a structure illustrated by FIG. 5, wherein the GST monomer protein (SEQ. ID. NO:20) is the dimeric unit 12 and NoV P- (SEQ. ID. NO:19) is the dimeric unit 14 on which a monomeric peptide VP8* (159 aa, SEQ. ID. NO:21) is merged as protein unit 62. Two domain forms of the NoV P- protein with a merged VP8* protein were made: the first was the VP8* inserted into surface Loop 2 [GST-NoV P--VP8* (loop 2) (SEQ. ID. NO:8)), and the second was the VP8* fused at the C-terminus of NoV P- [GST-NoV P--VP8* (C-end) (SEQ. ID. NO:9)]. Both proteins can be produced well in *E. coli* (FIG. 17A, Table 1) and form linear complexes as shown by gel filtration (FIG. 17B Panels B and C) and EM (FIG. 17B Panel H).

Figure 17B:
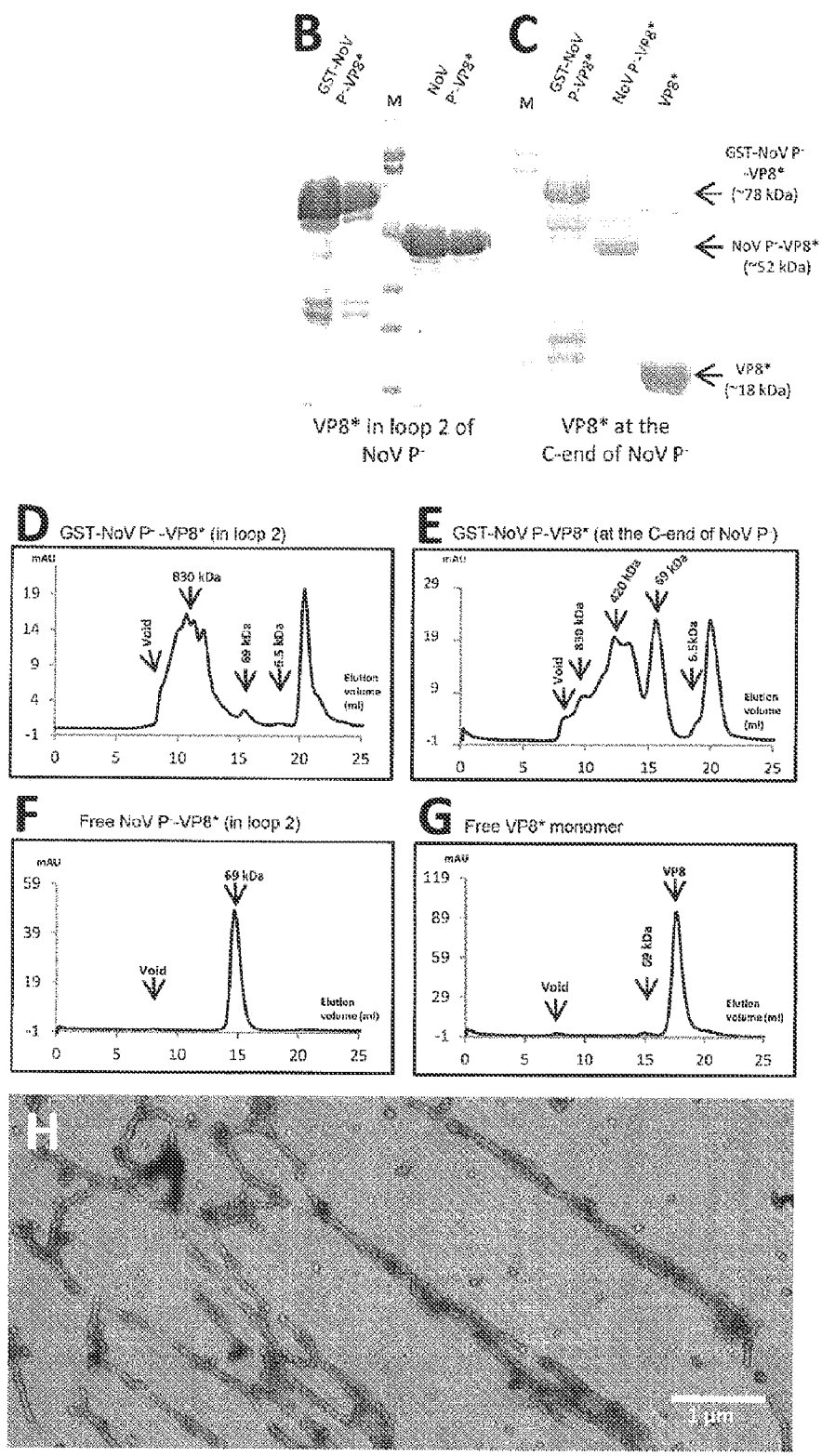
FIG. 17B: Panels B and show expression, purification and analysis of the GST-NoV P⁻-VP8* proteins (SEQ. ID. NOS:8 and 9) on SDS PAGE; Panels D and E show elution curves of gel filtration chromatography of the GST-NoV P⁻-VP8* (loop 2) (SEQ. ID. NO:8) and GST-NoV P⁻-VP8* (C-end) (SEQ. ID. NO:9), respectively; Panels F and G show the free NoV P⁻-VP8* (C-end) (SEQ. ID. NO:11) dimer and the free VP8* monomer protein (SEQ. ID. NO:21), respectively; Panel H shows an electron micrograph of negatively stained GST-NoV P⁻-VP8* (loop 2) (SEQ. ID. NO:8) protein revealing large linear molecules.
Figure 18:
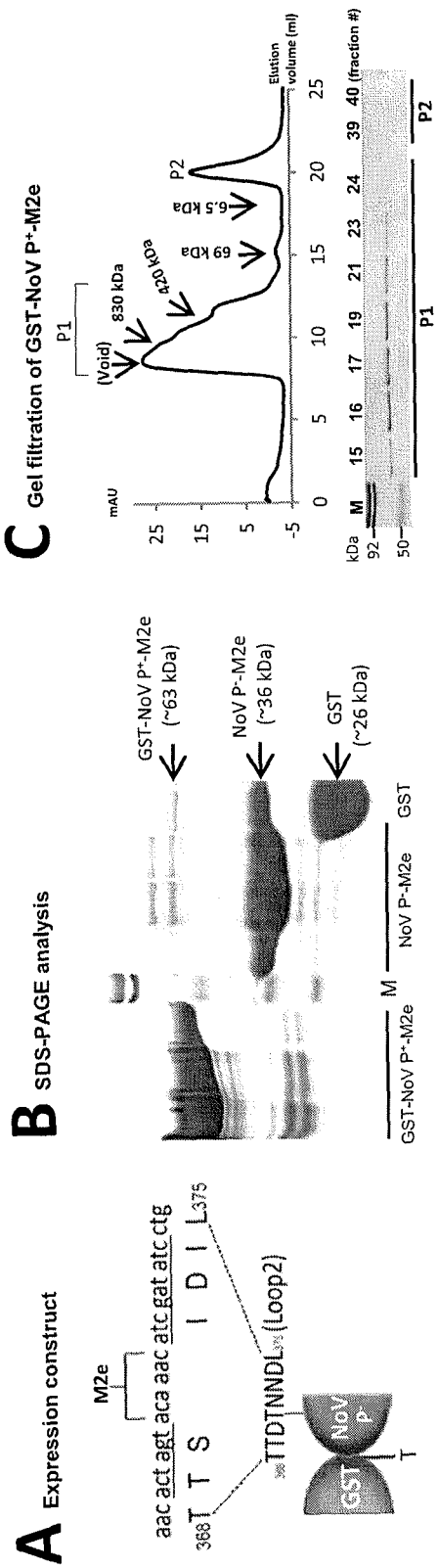
FIG. 18: Panel A is a schematic illustration of the GST-NoV P⁻-M2e fusion protein (SEQ. ID. NO:10); Panel B shows the expression, purification and analysis of the GST-NoV P⁻-M2e protein (SEQ. ID. NO:10) on SDS PAGE; Panel C shows the elution curves of gel filtration chromatography of the GST-NoV P⁻-M2e protein (SEQ. ID. NO:10).

FIG. 17B Panels B and C show expression, purification and analysis of the GST-NoV P--VP8* proteins on SDS PAGE. The GST-NoV P--VP8* proteins eluted from the GST-affinity column are shown on the left, while the NoV P--VP8* protein after a thrombin digestion of the GST-P fusion protein on the beads of the column on the right in FIG. 17B Panel B, and the middle in FIG. 17B Panel C. The free VP8* (SEQ. ID. NO:21) is shown on the far right column of FIG. 17B Panel C. Positions of the GST-NoV P--VP8* fusion protein (~78 kDa, SEQ. ID. NOS:8 and 9), NoV P--VP8* protein (~52 kDa, SEQ. ID. NO:11) and VP8* (~18 kDa, SEQ. ID. NO:21) are indicated. M represents a pre-stained protein marker (Bio-Rad, low range), with bands from top to bottom representing 113, 92, 52, 34, 29, and 21 kDa.

FIG. 17B Panels D and E both show elution curves of gel filtration chromatography of the GST-NoV P--VP8* (loop 2) (SEQ. ID. NO:8) and GST-NoV P--VP8* (C-end) (SEQ. ID. NO:9), respectively, while free NoV P--VP8* (C-end) (SEQ. ID. NO:11) dimer and the free VP8* monomer protein (SEQ. ID. NO:21) are shown in FIG. 17B Panels F and G, respectively. Both GST-NoV P--VP8* fusion proteins (SEQ. ID. NOS:8 and 9) formed a collection of large molecular complexes as shown by the peaks at high molecular weight regions in FIG. 17B Panels D and E, while the free NoV P--VP8* dimer and VP8* protein formed dimer (~100 kDa) and monomer (~18 kDa) in FIG. 17B Panels F and G, respectively. The gel filtration columns were calibrated by the Gel Filtration Calibration Kit (GE Healthcare Life Sciences) and the recombinant P particle, small P particle and P dimer of Norovirus (VA387). The elution positions of blue Dextran 2000 (~2000 kDa, void), the P particle (~830 kDa), the small P particle (420 kDa), P dimer (~69 kDa) and aprotinin (~6.5 kDa) were indicated. FIG. 17B Panel H shows an electron micrograph of negatively stained GST-NoV P--VP8* (loop 2) (SEQ. ID. NO:8) protein, revealing large linear molecules.

B. Another dimeric protein domain included a merged monomeric peptide or protein consisting of the small M2e epitope (23 aa, SEQ. ID. NO:57) of influenza virus. The small M2e epitope (23 aa) of influenza virus was inserted to the loop 2 of the GST-NoV P- and NoV P- (FIG. 18 Panel A), resulting in linear/network complex GST-NoV P--M2e (SEQ. ID. NO:10, see FIG. 18 Panels B and C) and NoV P--M2e dimer (SEQ. ID. NO:12, Table 1). Looking at the schematic illustration of the GST-NoV P--M2e fusion protein (SEQ. ID. NO:10) in Panel A, the sequence of loop 2 is shown with indication of the position where the sequence of the M2e epitope (SEQ. ID. NO:57) was inserted. The thrombin digestion site (T) between the GST and the NoV P- protein is indicated. Panel B shows the expression, purification and analysis of the GST-NoV P- -M2e protein on SDS PAGE. Positions of the GST-NoV P--M2e fusion protein (~63 kDa, (SEQ. ID. NO:10), NoV P--M2e (~36 kDa, SEQ. ID. NO:12) and GST (~26 kDa) proteins are indicated. M represents a pre-stained protein marker (Bio-Rad, low range), with bands from top to bottom representing 113, 92, 52, 34, and 29 kDa. Panel C shows the elution curves of gel filtration chromatography of the GST-NoV P⁻-M2e protein (SEQ. ID. NO:10). The protein formed a collection of large molecules as shown by the major peaks at and near the void volume of the size-exclusion column Superdex 200 (GE Healthcare Life Sciences). The proteins of the two major peaks (P1 and P2) in Panel C were analyzed by SDS PAGE below the elution curves of gel filtration chromatography. The gel filtration columns were calibrated by the Gel Filtration Calibration Kit (GE Healthcare Life Sciences) and the recombinant P particle, small P particle and P dimer of Norovirus (VA387). The elution positions of blue Dextran 2000 (~2000 kDa, void), the P particle (~830 kDa), the small P particle (420 kDa), P dimer (~69 kDa) and aprotinin (~6.5 kDa) were indicated.

8. Linear Complexes Increase the Immunogenicity of Merged Small Monomeric Proteins Immunization of the linear/network complexes with inserted peptide or protein to mice (N=8 mice/group) resulted in significantly higher titers of VP8*- or M2e-specific antibody than those induced by the free or NoV P⁻ dimer-presented VP8* or M2e (Ps<0.05) (see FIG. 19 Panels A and C). These results indicated a significantly improved immunogenicity of the inserted VP8*- or M2e after presentation by the linear/network complexes.

Figure 19:
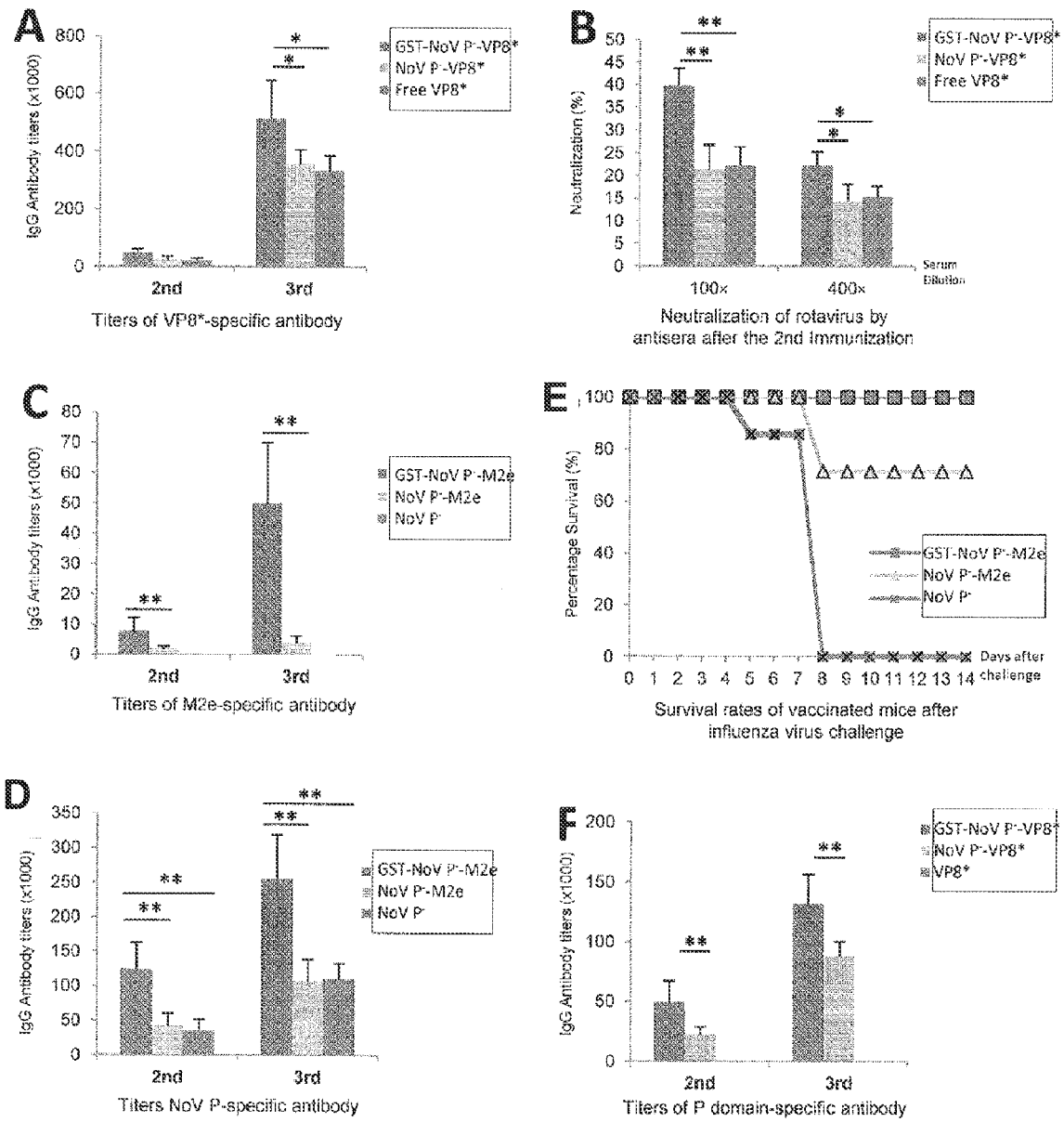
FIG. 19: Panel A shows the titers of rotavirus VP8*-specific antibody induced by linear complexes GST-NoV P⁻-VP8* (loop 2) (SEQ. ID. NO:8); Panel B shows mouse antisera after immunization with the linear complex GST-NoV P⁻-VP8*; Panel C shows the titers of influenza virus M2e-specific antibody induced by linear complexes GST-NoV P⁻-M2e (SEQ. ID. NO:10); Panel D shows the GST-NoV P⁻-M2e (SEQ. ID. NO:10) complexes also induced significantly higher titers of NoV P⁻-specific antibody than those induced by NoV P⁻ ⁻M2e (SEQ. ID. NO:12) or NoV P⁻ dimers; Panel E shows the survival rates of mice after vaccination with GST-NoV P⁻-M2e (SEQ. ID. NO:10), NoV P⁻-M2e (SEQ. ID. NO:12) or NoV P⁻ dimers followed by a challenge with lethal dose influenza virus. N=8 mice/group for all experiments; Panel F shows the titers of NOV P domain-specific antibody induced by linear complexes GST-NoV P⁻-M2e (SEQ. ID. NO:10).

In FIG. 19 Panels A-D, "2nd" means after the second immunization and "3rd" means after the third immunization. Statistical differences between data groups are indicated by start symbols (* P<0.05, ** P<0.01). FIG. 19A shows the titers of rotavirus VP8*-specific antibody induced by linear complexes GST-NoV P⁻ -VP8* (loop 2) (SEQ. ID. NO:8) were significantly higher than those induced by NoV P⁻-VP8* dimer or the free VP8* monomer. FIG. 19B shows mouse antisera after immunization with the linear complex GST-NoV P⁻ -VP8* exhibited significantly higher neutralizing activity on replication of rotavirus in a plaque reduction assay than those of sera after immunization with NoV P⁻-VP8* dimer or the free VP8* monomer. FIG. 19 Panel C shows the titers of influenza virus M2e-specific antibody induced by linear complexes GST-NoV P⁻-M2e (SEQ. ID. NO:10) were significantly higher than that induced by NoV P⁻-M2e (SEQ. ID. NO:12) dimer. Mouse sera after immunization with NoV P⁻ dimer were used as negative control. FIG. 19 Panel D shows the GST-NoV P⁻-M2e complexes also induced significantly higher titers of NoV P⁻-specific antibody than those induced by NoV P⁻-M2e (SEQ. ID. NO:12) or NoV P⁻ dimers. FIG. 19 Panel E shows the survival rates of mice after vaccination with GST-NoV P⁻-M2e (SEQ. ID. NO:10), NoV P⁻-M2e (SEQ. ID. NO:12) or NoV P⁻ dimers followed by a challenge with lethal dose influenza virus (N=8 mice/group for all experiments). Challenge experiments demonstrated that the GST-NoV P⁻-M2e (SEQ. ID. NO:10) chimeric vaccine fully protected mice (100% survival rate) against lethal challenge of the mouse adapted human influenza virus (PR8, H1N1), This protection was significantly higher than those provided by free M2e (12.5% survival rate) and the NoV P⁻-M2e chimeric vaccine (71% survival rate) (FIG. 19 Panel E) (Ps<0.05).

It is also noteworthy that both GST-NoV P⁻-VP8* and GST-NoV P⁻-M2e complexes also induced high titer of NoV-specific antibody that blocked binding of NoV to their HBGA receptors (FIG. 19 Panel F). Thus, the linear/network complexes of the present invention function as a useful vaccine platform for presentation of a monomeric peptide/protein for increased immunogenicity for vaccine development.

9. Linkers Having Cleavage Sites can Allow Breakdown or Complete Undoing of the Large Complex Structures Made of Fusion Proteins A linear complex, similar to one illustrated in FIG. 1, was formed by a GST-NoV P⁻ dimeric fusion protein (SEQ. ID. NO:3) having a cleavage site digestible by thrombin. NoV is a shortened P domain of Norovirus (NoV) as described herein. FIG. 14 Panels B-I show the characterization of the linear GST-NoV P⁻ complex. After expression of GST-NoV P⁻ in E. coli (SEQ. ID. NO:3, FIG. 14A, Table 1), the formation of the GST-NoV P⁻ complexes was confirmed via gel filtration (FIG. 14 Panel E) and EM (FIG. 14 Panels H and I). After treatment by thrombin digestion at the cleavage sites, the huge complexes disappeared completely, resulting in free dimers of NoV P⁻ (~69 kDa) and GST (~52 kDa), respectively (FIG. 14 Panels C, D, F and G).

FIG. 14 Panels B, C and D show the expression, purification and analysis of the GST-NoV P⁻ protein (SEQ. ID. NO:3) on SDS PAGE. More specifically, FIG. 14 Panel B shows the GST-affinity column-purified GST-NoV P⁻ protein, FIG. 14 Panel C shows the NoV P⁻ protein eluted from the GST-affinity column after a thrombin digestion of the GST-NoV P⁻ fusion protein on the beads of the column, and FIG. 14 Panel D shows the P protein from FIG. 14 Panel C after being further purified by a gel-filtration chromatography. Positions of the GST-NoV P⁻ fusion (SEQ. ID. NO:3, 56 kDa), NoV P⁻ (~34 kDa) and GST (~26 kDa) proteins are indicated. M represents a pre-stained protein marker (Bio-Rad, low range), with bands from top to bottom representing 113, 92, 52, 34, 29, and 21 kDa.

FIG. 14 Panel E shows the elution curve of gel filtration chromatography of the GST-NoV P⁻, FIG. 14 Panel F shows the free NoV P⁻ dimer, and FIG. 14 Panel G shows the elution curve of the GST proteins. GST-NoV P⁻ dimeric fusion protein (SEQ. ID. NO:3) formed a collection of large molecules as shown by the major peaks at and near the void volume of the size-exclusion column Superdex 200 in Panel E, while the free NoV P⁻ (Panel F) and GST (Panel G) proteins formed a defined single peak at ~69 kDa and ~56 kDa, representing the NoV P⁻ and GST dimer, respectively. Gel filtration was carried out using the size-exclusion column of Superdex 200 (10/300 GL, GE Healthcare Life Sciences), while chromatograph was performed using HiLoad 16/60 (GE Healthcare Life Sciences). The gel filtration columns were calibrated by the Gel Filtration Calibration Kit (GE Healthcare Life Sciences) and the recombinant P particle, small P particle and P dimer of Norovirus (VA387). The elution positions of blue Dextran 2000 (~2000 kDa, void), the P particle (~830 kDa), the small P particle (420 kDa), P dimer (~69 kDa) and aprotinin (~6.5 kDa) were indicated. Panel H shows an electron micrograph of negatively stained GST-NoV P⁻ protein (SEQ. ID. NO:3), revealing large linear molecules. The rectangular-labeled region in Panel H is enlarged in Panel I.

EXPERIMENTS, MATERIALS AND METHODS

Expression constructs. All expression constructs were generated with the help of glutathione S-transferase (GST)-gene fusion system using vector pGEX-4T-1 (GE Healthcare Life Sciences). The construct for expression of GST-HEV P fusion protein (SEQ. ID. NO:1) was generated by inserting the P2 domain encoding sequences (residue 452 to 617, AC # DQ079627, chemically synthesized by GenScript) of hepatitis E virus (HEV) to the vector pGEX-4T-1 between BamHI and NotI. Two modified forms of NoV P domain (SEQ. ID. NO:17) were used in this study, the P polypeptide and the P-RGDCFC that are herein designated as NoV P⁻ (SEQ. ID. NO:19) and NoV P⁺ (SEQ. ID. NO:18), respectively. The dimeric NoV P- is the NoV P domain with a deletion of the last four amino acids, while the oligomeric NoV P⁺ is the full-length NoV P domain with an extra cysteine-containing peptide (CDCRGDCFC) at its C-terminus. Both constructs of GST-NoV P⁻ (SEQ. ID. NO:3) and GST-NoV P⁺ (SEQ. ID. NO:2) of NoV strain VA387 (GII.4) were created previously. Throughout this disclosure, all NoV P domains were derived from GII.4 VA387 unless otherwise indicated.

The construct of GST-NoV P⁻-NoV P⁻ was made by constructing sequences to add one more NoV P⁻ (SEQ. ID. NO:19) to the end of the GST-NoV P⁻ protein (SEQ. ID. NO:3) through a linker of 12 glycines. The PCR-amplified NoV P⁻-encoding sequences using two primer pairs (P524 (SEQ. ID. NO:27)/P1617(SEQ. ID. NO:37) and P1618 (SEQ. ID. NO:38)/P561(SEQ. ID. NO:28)) with BsmBI sites (Table 2) were cloned to the end of the GST-NoV P⁻ (SEQ. ID. NO:3) after digestion with corresponding enzymes. NoV P⁻-NoV P⁻ (SEQ. ID. NOS:6 and 7) was a thrombin-cleaved product of the GST-NoV P⁻-NoV P⁻ (SEQ. ID. NOS:4 and 5). The constructs of GST-NoV P⁻ (387)-NoV P⁻ (207) (SEQ. ID. NO:4) and GST-NoV P⁻ (387)-NoV P⁻ (115) (SEQ. ID. NO:5), complexes containing NoV P⁻ of different strains, were made through similar approach using primer sets of P524(SEQ. ID. NO:27)/P1617 (SEQ. ID. NO:37) for VA387 (GII.4, SEQ. ID. NO:19), P1957(SEQ. ID. NO:46)/P1958(SEQ. ID. NO:47) for VA207 (GII.9, SEQ. ID. NO:25), and P1955(SEQ. ID. NO:45)/P846(SEQ. ID. NO:33) for VA115 (GI.3, SEQ. ID. NO:26, Table 2). The NoV P⁻ (387)-NoV P⁻ (207) (SEQ. ID. NO:6) and the NoV P⁻ (387)-NoV P⁻ (115) (SEQ. ID. NO:7) proteins were obtained by thrombin digestion of their GST-fusion proteins. The constructs of GST-NoV P⁻-VP8* (loop 2) (SEQ. ID. NO:8) and GST-NoV P⁻-M2e (SEQ. ID. NO:10), each with the VP8* (SEQ. ID. NO:21) or M2e (SEQ. ID. NO:57) at loop 2 of the P domain, were made by cloning the PCR-amplified sequences of NoV P⁻s with M2e/VP8* at loop 2 from previously made constructs using primers P524(SEQ. ID. NO:27) and P561(SEQ. ID. NO:28) in the vector pGEX-4T-1. cDNA sequences encoding individual NoV P⁻s of VA207 (SEQ. ID. NO:25) and VA115 (SEQ. ID. NO:26) were amplified by primer sets P821(SEQ. ID. NO:30)/P834(SEQ. ID. NO:31) and P843(SEQ. ID. NO:32)/P846(SEQ. ID. NO:33), respectively.

Expression and purification of recombinant proteins. Recombinant proteins were expressed in *E. coli* strain BL21 (DE3) with an induction of 0.5 mM isopropyl-β-D-thiogalactopyranoside (IPTG) at room temperature (22° C.) overnight as described previously. The GST fusion proteins were purified using resin of Glutathione Sepharose 4 Fast Flow medium (GE Healthcare Life Sciences) according to the manufacturer's instruction. GST was removed from the target proteins by thrombin (GE Healthcare Life Sciences) cleavage either on bead or in phosphate-buffered saline PBS, pH 7.4).

TABLE 2

Primers used to generate expression constructs of recombinant proteins

| Name | Sequence (5' to 3') | Sense | Enzyme | Locations/Constructs |
|------|---------------------|-------|--------|----------------------|
| P524 | GCACGGATCCTCAAGAACTAAACCATTCACC (SEQ. ID. NO: 27) | + | BamHI | N-end of the Norovirus VA 387 P domain |
| P561 | GCGTGCGGCCGCTTACCCCGCTCCATTTCCCATGGG (SEQ. ID. NO: 28) | − | NotI | C-end of the Norovirus VA 387 P domain with R cluster |
| P590 | GCATGCGGCCGCTTAGCAAAAGCAATCGCCACGGCAATCGCATAA TGCACGTCTGCGCCCCGC (SEQ. ID. NO: 29) | − | NotI | C-end of the Norovirus VA 387 P domain |
| P821 | GCACGGATCCTCAAAGACTAAGGCATTCAC (SEQ. ID. NO: 30) | + | BamHI | N-end of the Norovirus VA 207 P domain |
| P834 | AGTCGCGGCCGCTTAGCGCCCACTTCCAGTTCCCAC (SEQ. ID. NO: 31) | − | NotI | C-end of the Norovirus VA 207 P domain without R cluster |
| P843 | GCACGGATCCCAAAAGACTAAACCATTTAG (SEQ. ID. NO: 32) | + | BamHI | N-end of the Norovirus VA 115 P domain |
| P846 | GCATGCGGCCGCTTAACGAGCCGGGCCGGCTGTTC (SEQ. ID. NO: 33) | − | NotI | C-end of the Norovirus VA 115 P domain without R cluster |
| P1572 | ATATCGTCTCCCCCCGCTCCATTTCCCATG (SEQ. ID. NO: 34) | − | BsmBI | C-end of the Norovirus VA 387 P domain without R cluster |
| P1573 | TATTCGTCTCCGGGGGTGAGCAAGGGCGA (SEQ. ID. NO: 35) | + | BsmBI | N-end of GFP |
| P1574 | GCATGCGGCCGCTTACTTGTACAGCTCGTCC (SEQ. ID. N0: 36) | − | NotI | C-end of GFP |

TABLE 2 -continued

Primers used to generate expression constructs of recombinant proteins

| Name | Sequence (5' to 3') | Sense | Enzyme | Locations/Constructs |
|---|---|---|---|---|
| P1617 | ATATCGTCTCCCCTCCGCCTCCGCCTCCGCCCCCCGCTCCATTTCC (SEQ. ID. NO: 37) | – | BsmBI | Tandem repeat of the Norovirus VA 387 P polypeptide linked with 12 G |
| P1618 | TATTCGTCTCCGAGGCGGAGGCGGAGGCGGATCAAGAACTAAACC (SEQ. ID. NO: 38) | + | BsmBI | Tandem repeat of the Norovirus VA 387 P polypeptide linked with 12 G |
| P1656 | TATTCGTCTCCGGGGATCGAGGGAAGGATTTCAATGTCACCGATA CTA (SEQ. ID. NO: 39) | + | BsmBI | N-end of GST |
| P1657 | GCATGCGGCCGCTTAATCCGATTTTGGAGGATGGTCG (SEQ. ID. NO: 40) | – | NotI | C-end of GST |
| P1689 | ATACGCGGATCCTGCAACGGCCGTTGCTCAAGAACTAAACCATTC ACCGT (SEQ. ID. NO: 41) | + | BamHI | N-end of the Norovirus VA 387 P domain |
| P1734 | ATATCGTCTCCTAATGCACGTCTGCGCCCCGC (SEQ. ID. NO: 42) | – | BsmBI | C-end of the Norovirus VA 387 P domain with R cluster |
| P1735 | TATTCGTCTCCATTATTAGATGGTCCTTATCAACC (SEQ. ID. NO: 43) | + | BsmBI | N-end of humanVP8 |
| P1736 | GCATGCGGCCGCTTATAGACCGTTGTTAATATATTC (SEQ. ID. NO: 44) | – | NotI | C-end of humanVP8 |
| P1955 | TATTCGTCTCCGAGGCGGAGGCGGAGGCGGACAAAAGACTAAACC ATTTAG (SEQ. ID. NO: 45) | + | BsmBI | N-end of the Norovirus VA 115 P domain |
| P1957 | TATTCGTCTCCGAGGCGGAGGCGGAGGCGGATCAAAGACTAAGGC ATTCAC (SEQ. ID. NO: 46) | + | BsmBI | N-end of the Norovirus VA 207 P domain |
| P1958 | GCATGCGGCCGCTTACCCACTTCCAGTTCCCACAG (SEQ. ID. NO: 47) | – | NotI | C-end of the Norovirus VA 207 P domain |
| P1985 | ATATTATTGCACGGATCCCCGACCCCGTCTCCGGCTC (SEQ. ID. NO: 48) | + | BamHI | N-end of the HEV P domain |
| P1986 | GCATGCGGCCGCTTAGCAAAAGCAATCGCCACGGCAATCGCACGG GTAGTCAACGGTGTC (SEQ. ID. NO: 49) | – | NotI | C-end of the HEV P domain |

Gel Filtration Chromatography.

Gel filtration was performed through an Akta Fast Performance Liquid Chromatography (FPLC) system (model 920, GE Healthcare Life Sciences) using size exclusion columns (Superdex 200, GE Healthcare Life Sciences) as described previously. Two Superdex 200 columns were used: HiLoad 16/60 with 120 ml bed volume and 10/300 GL with 24 ml bed volume. The columns were calibrated by the gel filtration calibration kits (GE Healthcare Life Sciences) and the purified NoV P particle (~830 kDa, SEQ. ID. NO:17), small P particle and P dimer (~69 kDa) as described previously. The protein identities in the peaks of interest were further analyzed by sodium dodecyl sulfate-polyacrylamide gel electrophoresis (SDS-PAGE) followed by a western blot analysis using specific antibody described elsewhere.

SDS-PAGE and protein concentration determination.
Recombinant proteins were analyzed by SDS-PAGE using freshly prepared 10% separating gels. Protein concentrations were determined on SDS-PAGE using diluted bovine serum albumin (BSA, Bio-Rad) as standards.

Western blot analysis.
The identity of the NoV P protein (SEQ. ID. NO:17) was confirmed by Western blot analysis as described previously. Blotted membrane was incubated with homemade guinea pig hyperimmune sera against NoV VLPs (VA387, GII.4; 1:3,000). Then the secondary antibody-horseradish peroxidase (HRP) conjugates (1:5,000; ICN Pharmaceuticals, Costa Mesa, Calif.) were added. The HRP was detected by enhanced chemiluminescence (ECL) Eastern blotting detection reagents (GE Healthcare, Buckinghamshire, England).

Electron microscopy (EM).
Negative-stain EM was utilized to visualize the morphology of the complexes as described previously. A 7-μl drop of protein solution was applied on a parafilm sheet and an EM grid (Electron Microscopy Sciences, Inc) was set on the drop for 10 min in a humidified chamber. The grid was washed for a few seconds on a drop of water and then was stained with the 1% ammonium molybdate solution for 30s. The grid was examined in a Phillips CM10 electron microscope operating at 80 kV.

Enzyme immunoassay (EIA).
To measure immune reactivity and antibody titers of mouse antisera after immunization with different protein antigens an EIA was used as described elsewhere. Different purified recombinant antigens were used for different antisera: 1) gel-filtration purified NoV P⁻ proteins (SEQ. ID. NO:19) of different strains were used to determine the P domain specific antibody titers of the mouse sera after immunization with the different P domain complexes; 2) free VP8* (SEQ.

ID. NO:21) was used to determine the VP8* specific antibody titer of the mouse sera after immunization with different P complex-VP8 chimeras; and 3) synthesized free M2e peptide (SEQ. ID. NO:57) was used to determine the M2e specific antibody of the mouse sera induced by different P complex-M2e chimeras. Antigens (1 m/ml) were coated on 96-well microtiter plates (Dynex Immulon) at 4° C. overnight. Diluted sera were incubated with the coated antigens. The bound antibody was detected by the secondary antibody-HRP conjugate. Antigen-specific antibody titers were defined as the end-point dilutions with a cutoff signal intensity of 0.2. Sera from animals that were immunized with PBS were used as negative controls.

$CD4^+$ T cell responses.

Spleens were collected from immunized mice at four weeks after the last immunization. A suspension of splenocytes was prepared by lysing red blood cells with 1×RBC lysis buffer (eBioscience) followed by washing with FACS buffer (1×PBS with 1% FBS and 0.01% $NaN_3$). For intracellular cytokine staining, splenocytes were resuspended in RPMI-1640 medium with 1:1000 Brefeldin A (eBioscience) and stimulated with VA387 (HFYQEAAPAQSDVAL, SEQ. ID. NO:22), VA207 (ATARSEVALLRFVNP, (SEQ. ID. NO:23) or VA115 (TLTEAAQLAPPIYPP, SEQ. ID. NO:24) $CD4^+$ T cell epitopes (synthesized by GenScript) at 5 μg/ml for 6 hours in a 96-well plate at 37° C. The CD4 T epitope of VA387 was reported previously, while those of VA207 and VA115 were predicted by Immune Epitope Database Analysis Resource (IEDB) (http://tools.immuneepitope.org/main/). Cells were then washed with FACS buffer and surface makers CD3 and CD4 (Biolegend) were stained for 15 minutes at 4° C. Cells were washed and fixed with fixation buffer at 4° C. overnight. For cytokine staining, cells were washed with 1× permeabilization buffer and stained with fluorochrome-conjugated cytokine antibodies (anti-mouse IL-2, IFN-γ, TNF-α, Biolegend) for 30 minutes at 4° C. After washed with 1× permeabilization buffer and then FACS buffer, cells were resuspended in FACS buffer for acquisition. All samples were analyzed on a BD Accuri™ C6 flow cytometer and data was analyzed by Accuri™ C6 software.

Histo-blood group antigen (HBGA) binding and blocking assays.

The saliva-based binding assays were performed as described elsewhere. Briefly, boiled saliva samples with known HBGA phenotypes were coated on 96-well microtiter plates (Dynex Immulon). Protein complexes GST-NoV $P^-$-NoV $P^-$ (SEQ. ID. NOS:4 and 5) and NoV $P^-$-NoV $P^-$ (SEQ. ID. NOS:6 and 7) and free NoV $P^-$ dimer of VA387 (SEQ. ID. NO:19) were incubated with the coated saliva. The bound NoV $P^-$ proteins were detected using guinea pig anti-VA387 VLP antiserum (1:3300), followed by an addition of HRP-conjugated goat anti-guinea pig IgG (ICN Pharmaceuticals). In a blocking assay, the blocking effects of the mouse sera on the binding of the VLP or P particle to saliva were measured by a pre-incubation of the VLP/P particles with diluted sera for 1 h before the VLP/P particles were added to the coated saliva. The blocking rates were calculated as reduction rates by comparing the optical density (OD) with and without blocking by the mouse sera. The blocking titer 50 (BT50) was defined as the dilution of the antisera that produced a 50% reduction on the binding of NoV VLP/P particle to saliva.

Immunization of mice.

Female BALB/c mice (Harlan-Sprague-Dawley, Indianapolis, Ind.) at 3-4 weeks of age were immunized with different linear/network complexes: for example, 1) GST-NoV $P^-$ (387)-NoV $P^-$ (207) (SEQ. ID. NO:4), 2) GST-NoV $P^-$ (387)-NoV $P^-$ (115) (SEQ. ID. NO:5), 3) NoV $P^-$ (387)-NoV $P^-$ (207) (SEQ. ID. NO:6), and 4) NoV $P^-$ (387)-NoV $P^-$ (115) (SEQ. ID. NO:7). Two 1:1 mixtures of the corresponding free NoV $P^-$ dimers [NoV $P^-$ (387) (SEQ. ID. NO:19)+NoV $P^-$ (207) (SEQ. ID. NO:25) and NoV $P^-$ (387) (SEQ. ID. NO:19)+NoV $P^-$ (115) (SEQ. ID. NO:26)] were used as controls. Equal molar amounts (0.143 nanomole/mouse, e.g. equal to 10 μg/mouse for the NoV $P^-$-NoV P) of each immunogen were used to insurance the same amount of protein component. Mice (n=8 mice/group) were immunized three times intranasally without an adjuvant in a 2-week interval as described previously. Blood was collected by retro-orbital capillary plexus puncture before each immunization and four weeks after the final immunization. Sera were processed from blood via a standard protocol. Spleens were collected from mice to isolate splenocytes for cellular immune responses.

To determine the immune response induced by the complex-presented VP8*, equal molar amount (0.838 nanomole/mouse, e.g. equal to 15 μg/mouse for the free VP8*) of each immunogen (GST-NoV $P^-$-VP8* (SEQ. ID. NOS:8 and 9), NoV $P^-$-VP8* (SEQ. ID. NO:11), and the free VP8* (SEQ. ID. NO:21)) were used for the same molecular number of VP8*component. Mice (n=8 mice/group) were immunized intranasally without adjuvant three times in a 2-week interval. Mice were bled before and 2 weeks after each immunization.

Rotavirus plaque assay.

This was performed to determine the neutralizing activity of mouse sera after immunization with GST-NoV $P^-$-VP8*complexes on rotavirus replication as described elsewhere. Briefly, MA104 cells were cultivated in 6-well plates and tissue culture-adapted rotavirus Wa (G1P) at a titer of ~50 PFU/well was used as the inoculum. Trypsin-treated rotavirus was incubated with mouse sera for 1 h and then was added to the cells. The plates were overlaid with media with trypsin (Invitrogen) and 0.8% agarose. After 4-day incubation the plaques were stained and counted. The neutralization (%) of the sera was calculated by the reduction in plaque numbers in the wells treated with antisera relative to the number in untreated control wells.

Mouse influenza virus challenge model.

The model described in previous study was used to measure the protective efficacy of GST-NoV $P^-$-M2e complexes. BALB/c mice (n=8 mice/group) at 6 to 8 weeks of age (Harlan-Sprague-Dawley) were immunized intranasally three times at 2-week interval with GST-NoV $P^-$-M2e (SEQ. ID. NO:10), NoV $P^-$-M2e (SEQ. ID. NO:12), and NoV (SEQ. ID. NO:19) without an adjuvant. Equal molar amounts (0.556 nanomole/mouse, e.g. equal to 20 μg/mouse of NoV $P^-$-M2e) of each immunogen, GST-NoV $P^-$-M2e (SEQ. ID. NO:10) and NoV $P^-$-M2e (SEQ. ID. NO:12), were administered to mice. Same amount of NoV $P^-$ dimer were used as negative control. Animals were bled before and 2 weeks after each immunizations. Sera antibody titers specific to M2e peptide (SEQ. ID. NO:57) and NoV P domain (SEQ. ID. NO:17) were measured by EIA. Two weeks after the third immunization, mice were challenged with mouse adapted influenza virus PR8 strain (H1N1) at a dose of $2 \times 10^6$ fluorescent focus forming units (ffu) or approximately $1 \times LD_{50}$, in 40 μl of PBS per mouse. Mice were monitored daily for changes in body weight and mortality.

Statistical analysis.

Using software Minitab, version 15 (Minitab, Inc.), a non-parametric Mann-Whitney test was performed to determine statistically significant differences among data groups. P-values were set at 0.05 (P<0.05) for significant difference, and 0.01 (P<0.01) for highly significant difference.

While the present invention has been illustrated by the description of embodiments thereof, and while the embodiments have been described in considerable detail, it is not intended to restrict or in any way limit the scope of the appended claims to such detail. Additional advantages and modifications will be readily apparent to those skilled in the art. The invention in its broader aspects is therefore not limited to the specific details, representative system and method, and illustrated examples shown and described. Accordingly, departures can be made from such details without departing from the scope or spirit of the invention.

What is claimed is:

1. A vaccine or vaccine platform having a linear network structure comprising two dimeric proteins derived from different species,
   wherein said two dimeric proteins are connected by a linker peptide;
   wherein said two dimeric proteins dimerize to form a homo-dimer;
   wherein said linear network structure is formed via intermolecular interactions between said two dimeric proteins;
   wherein at least one of the dimeric proteins comprises a P domain of a virus selected from the group consisting of Norovirus (NoV), Hepatitis E virus (REV), and Astrovirus (AstV).

2. The vaccine or vaccine platform according to claim 1, wherein at least one dimeric protein is SEQ. ID. NO:17.

3. The vaccine or vaccine platform according to claim 1, wherein at least one of the two dimeric proteins further comprises SEQ. ID. NO:20.

4. The vaccine or vaccine platform according to claim 1, wherein the linker peptide comprises a length of amino acid units sufficient to allow the at least two dimeric proteins to fold into the proper structures without interference.

5. The vaccine or vaccine platform according to claim 1, wherein at least one of the at least two dimeric protein proteins includes a foreign antigen.

6. The vaccine or vaccine platform according to claim 5, wherein the foreign antigen comprises a foreign viral antigen.

7. The vaccine or vaccine platform according to claim 1, further comprising a monomer of a dimeric protein, which forms a dimer cap at the same dimeric protein exposed on a dimeric fusion protein.

8. A vaccine or vaccine platform having a network protein complex structure comprising three dimeric proteins,
   wherein said three dimeric proteins are derived from different species;
   wherein said three dimeric proteins are connected by a linker peptide;
   wherein said dimeric proteins form a homo-dimer;
   wherein said network protein complex structure is formed via intermolecular interactions between said three dimeric protein domains;
   wherein at least one of said three dimeric proteins are one or more of a virus P domain selected from Norovirus (NoV), Hepatitis E virus (REV), and Astrovirus (AstV).

9. The vaccine or vaccine platform according to claim 8, wherein at least one dimeric protein is SEQ. ID. NO:17.

10. The vaccine or vaccine platform according to claim 8, wherein at least one of the two dimeric proteins is SEQ. ID. NO:20.

11. The vaccine or vaccine platform according to claim 8, wherein the linker peptide comprises a length of amino acid units sufficient to allow the at least two dimeric proteins to fold into the proper structures without interference.

12. The vaccine or vaccine platform according to claim 8, wherein at least one of the at least two dimeric proteins includes a foreign antigen.

13. The vaccine or vaccine platform according to claim 8, wherein the foreign antigen comprises a foreign viral antigen.

14. The vaccine or vaccine platform according to claim 8, further comprising a monomer of a dimeric protein, which forms a dimer cap at the same dimeric protein domain exposed on a dimeric fusion protein.

* * * * *

UNITED STATES PATENT AND TRADEMARK OFFICE
CERTIFICATE OF CORRECTION

PATENT NO. : 9,562,077 B2  
APPLICATION NO. : 13/803057  
DATED : February 7, 2017  
INVENTOR(S) : Tan et al.

Page 1 of 1

It is certified that error appears in the above-identified patent and that said Letters Patent is hereby corrected as shown below:

In the Claims

Column 111, Claim 1, Line 35, delete "... Hepatitis E virus (REV), and ..." and insert --... Hepatitis E virus (HEV), and ...--

Column 112, Claim 8, Line 34, delete "... Hepatitis E virus (REV), and ..." and insert --... Hepatitis E virus (HEV), and ...--

Column 112, Claim 13, Line 48, delete "... according to claim 8, ..." and insert --... according to claim 12, ...--

Signed and Sealed this  
Twenty-eighth Day of March, 2017

Michelle K. Lee  
*Director of the United States Patent and Trademark Office*